US011136570B2

(12) United States Patent
Miller

(10) Patent No.: US 11,136,570 B2
(45) Date of Patent: *Oct. 5, 2021

(54) ANTIMICROBIAL FUSION PROTEINS COMPRISING AN ENDOLYSIN AND AN AMPHIPATHIC PEPTIDE SEGMENT

(71) Applicant: LYSANDO AG, Triesenberg (LI)

(72) Inventor: Stefan Miller, Regensburg (DE)

(73) Assignee: LYSANDO AG, Triesenberg (LI)

( * ) Notice: Subject to any disclaimer, the term of this patent is extended or adjusted under 35 U.S.C. 154(b) by 0 days.

This patent is subject to a terminal disclaimer.

(21) Appl. No.: 16/260,407

(22) Filed: Jan. 29, 2019

(65) Prior Publication Data

US 2019/0218538 A1    Jul. 18, 2019

Related U.S. Application Data

(63) Continuation of application No. 13/380,329, filed as application No. PCT/EP2010/059152 on Jun. 28, 2010, now abandoned.

(30) Foreign Application Priority Data

Jun. 26, 2009    (EP) .................................... 09163955

(51) Int. Cl.
| | | |
|---|---|---|
| *C12N 9/48* | (2006.01) | |
| *C12N 1/21* | (2006.01) | |
| *A61K 38/48* | (2006.01) | |
| *C12N 9/52* | (2006.01) | |
| *C07K 14/47* | (2006.01) | |
| *C12N 9/36* | (2006.01) | |
| *A61K 38/00* | (2006.01) | |

(52) U.S. Cl.
CPC ............ *C12N 9/52* (2013.01); *C07K 14/4723* (2013.01); *C12N 9/2462* (2013.01); *A61K 38/00* (2013.01); *C07K 2319/035* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 5,985,271 A | 11/1999 | Fischetti et al. | |
| 5,993,809 A | 11/1999 | Waever et al. | |
| 6,440,935 B1 | 8/2002 | Jaynes | |
| 6,503,881 B2 | 1/2003 | Krieger et al. | |
| 6,936,244 B2 | 8/2005 | Fiochetti et al. | |
| 7,572,602 B1 | 8/2009 | Donovan | |
| 8,383,102 B2 | 2/2013 | Donovan | |
| 9,388,400 B2* | 7/2016 | Miller .................. | C12N 9/2462 |
| 2002/0127220 A1 | 9/2002 | Grant et al. | |
| 2003/0113298 A1 | 6/2003 | Fischetti | |
| 2003/0167477 A1 | 9/2003 | Cottingham et al. | |
| 2006/0034820 A1 | 2/2006 | Lim et al. | |
| 2006/0147442 A1 | 7/2006 | Homan et al. | |
| 2009/0130185 A1 | 5/2009 | Coote et al. | |
| 2010/0092968 A1 | 4/2010 | Beissinger et al. | |

FOREIGN PATENT DOCUMENTS

| | | |
|---|---|---|
| DE | 10 2006 061002 | 6/2008 |
| EP | 0 510 907 | 10/1992 |
| JP | 2012/530510 | 12/2012 |
| WO | WO 1994/04688 | 3/1994 |
| WO | WO 1996/06532 | 3/1996 |
| WO | WO 2000/12528 | 3/2000 |
| WO | WO 2001/000855 | 1/2001 |
| WO | WO 2003/089455 | 10/2003 |
| WO | WO 2005/024002 | 3/2005 |
| WO | WO 2005/108563 | 11/2005 |
| WO | WO 2007/022768 | 3/2007 |
| WO | WO 2009/041830 | 4/2009 |
| WO | WO 2009/068858 | 6/2009 |

(Continued)

OTHER PUBLICATIONS

UniProt Database Accession No. Q6Y7T6, Oct. 2008, 1 page (Year: 2008).*
Loomans et al., J. Infect. Dis. 177:812-814, 1998 (Year: 1998).*
GenBank Database Accession No. X85010, May 1999, 2 pages (Year: 1999).*
GenBank Database Accession No. ABE68589, May 2007, 1 page (Year: 2007).*
Kweon et al., Biotechnol. Prog. 18:303-308, 2002 (Year: 2002).*
Hu et al., "Expression Tags for Protein Production", "Encyclopedia of Life Sciences", 7 pages, John Wiley and Sons, New York, 2007 (Year: 2007).*
"Amphipathic", English-Russian Thesaurus of Genetic Terms, 1995, cited in corresponding Eurasian Application No. 20100628.

(Continued)

*Primary Examiner* — David Steadman
(74) *Attorney, Agent, or Firm* — Parker Highlander PLLC

(57) ABSTRACT

The present invention relates to antimicrobial agents against Gram-positive bacteria, in particular to fusion proteins composed of an enzyme having the activity of degrading the cell wall of Gram-positive bacteria and an additional peptide stretch fused to the enzyme at the N- or C-terminus. Moreover, the present invention relates to nucleic acid molecules encoding said fusion protein, vectors comprising said nucleic acid molecules and host cells comprising either said nucleic acid molecules or said vectors. In addition, the present invention relates to said fusion protein for use as a medicament, in particular for the treatment or prevention of Gram-positive bacterial infections, as diagnostic means or as cosmetic substance. The present invention also relates to the treatment or prevention of Gram-positive bacterial contamination of foodstuff, of food processing equipment, of food processing plants, of surfaces coming into contact with foodstuff, of medical devices, of surfaces in hospitals and surgeries. Further, the present invention relates to a pharmaceutical composition comprising said fusion protein.

8 Claims, No Drawings

Specification includes a Sequence Listing.

(56) References Cited

FOREIGN PATENT DOCUMENTS

| WO | WO 2010/011960 | 1/2010 |
|---|---|---|
| WO | WO 2010/020657 | 2/2010 |
| WO | WO 2010/023207 | 3/2010 |
| WO | WO 2010/091294 | 8/2010 |
| WO | WO 2010/149792 | 12/2010 |
| WO | WO 2010/149795 | 12/2010 |
| WO | WO 2011/023702 | 3/2011 |
| WO | WO 2011/134998 | 11/2011 |

OTHER PUBLICATIONS

"Antimicrobial peptides", Cited in corresponding Eurasian Application No. 20100628, English translation shown on p. 2.
"Bacteriophages", Cited in corresponding Eurasian Application No. 20100628, English translation shown on p. 2.
"Chain A, Pleruocidin", Accession No. 1Z64_A, accessed from www.ncbi.nlm.nih.gov on Jan. 24, 2019.
"Infection", Great Soviet Encyclopedia, dated 1969-1978. English Translation.
"LYS_BPCP1", EBI accession No. UNITPROT:P15057, dated Apr. 1, 1990.
"Lysozyme," Wikipedia website located at http://en.wikipedia.org/wiki/Lysozyme; downloaded Jul. 31, 2014.
"PET-21-d(+) Vectors", Product Information Sheet, Novagen, 1998.
"PHIKZ144 [Pseudomonas phage phiKZ]", Genbank Accession No. AAL83045.1, downloaded from www.ncbi.nlm.nih.gov, 2002.
Amersham Pharmacia Biotech BioDirectory, p. 94, print 2000.
Amersham Pharmacia Biotech Catalogue, p. 332, print 1998.
Arima, Hideyuki, et al. "Bactericidal action of lysozymes attached with various sizes of hydrophobic peptides to the C-terminal using genetic modification." *FEBS letters* 415.1 (1997): 114-118.
Becker, Stephen C., Juli Foster-Frey, and David M. Donovan. "The phage K lytic enzyme LysK and lysostaphin act synergistically to kill MRSA." *FEMS microbiology letters* 287.2 (2008): 185-191.
Boehringer Mannheim Biochemicals Catalog, p. 13, print 1996.
Borysowski, Jan, Beata Weber-Dabrowska, and Andrzej Górski. "Bacteriophage endolysins as a novel class of antibacterial agents." *Experimental Biology and Medicine*231.4 (2006): 366-377.
Brandenburg, Klaus, Michel HJ Koch, and Ulrich Seydel. "Biophysical characterisation of lysozyme binding to LPS Re and lipid A." *European journal of biochemistry* 258.2 (1998): 686-695.
Briers, Yves, et al. "A standardized approach for accurate quantification of murein hydrolase activity in high-throughput assays." *Journal of biochemical and biophysical methods* 70.3 (2007): 531-533.
Briers, Yves, et al. "Muralytic activity and modular structure of the endolysins of Pseudomonas aeruginosa bacteriophages ɸKZ and EL." *Molecular microbiology* 65.5 (2007): 1334-1344.
Bülow, Leif, and Klaus Mosbach. "Multienzyme systems obtained by gene fusion." *Trends in biotechnology* 9.1 (1991): 226-231.
Callewaert, Lien, and Chris W. Michiels. "Lysozymes in the animal kingdom." *Journal of biosciences* 35.1 (2010): 127-160.
Cheng, Qi, et al. "Removal of group B streptococci colonizing the vagina and oropharynx of mice with a bacteriophage lytic enzyme." *Antimicrobial agents and chemotherapy* 49.1 (2005): 111-117.
Conlon, J. Michael, et al. "Peptidomic analysis of skin secretions supports separate species status for the tailed frogs, *Ascaphus truer* and *Ascaphus montanus*." *Comparative Biochemistry and Physiology Part D: Genomics and Proteomics* 2.2 (2007): 121-125.
Deacon, Ashley M., et al. "Protein crystallography using a multilayer monochromator." *Journal of synchrotron radiation*5.3 (1998): 494-496.
Diaz, Eduardo, Rubens Lopez, and Jose L. Garcia. "Chimeric phage-bacterial enzymes: a clue to the modular evolution of genes." *Proceedings of the National Academy of Sciences*87.20 (1990): 8125-8129.
Diaz, Eduardo, Rubens López, and Jose L. Garcia. "Chimeric pneumococcal cell wall lytic enzymes reveal important physiological and evolutionary traits." *Journal of Biological Chemistry* 266.9 (1991): 5464-5471.

Ding, J. L., P. Li, and B. Ho. "The Sushi peptides: structural characterization and mode of action against Gram-negative bacteria." *Cellular and Molecular Life Sciences* 65.7-8 (2008): 1202-1219.
Dmitriev, Boris A., et al. "Tertiary structure of *Staphylococcus aureus* cell wall murein." *Journal of bacteriology* 186.21 (2004): 7141-7148.
Donovan, David M., et al. "Peptidoglycan hydrolase fusions maintain their parental specificities." *Appl. Environ. Microbiol.*72.4 (2006): 2988-2996.
Düring, Klaus, et al. "The non-enzymatic microbicidal activity of lysozymes." *FEBS letters* 449.2-3 (1999): 93-100.
England, Patrick, et al. "Functional characterization of the somatic hypermutation process leading to antibody D1. 3, a high affinity antibody directed against lysozyme." *The Journal of Immunology* 162.4 (1999): 2129-2136.
Falla, Timothy J., D. Nedra Karunaratne, and Robert EW Hancock. "Mode of action of the antimicrobial peptide indolicidin." *Journal of Biological Chemistry* 271.32 (1996): 19298-19303.
Fokine, Andrei, et al. "Structure of the bacteriophage ɸKZ lytic transglycosylase gp144," *Journal of biological chemistry*283.11 (2008): 7242-7250.
Garcia, E. R. N. E. S. T. O., et al. "Molecular evolution of lytic enzymes of *Streptococcus pneumoniae* and its bacteriophages." *Proceedings of the National Academy of Sciences* 85.3 (1988): 914-918.
Garlitz, Jennifer A., et al. "Ethylammonium nitrate: a protein crystallization reagent," *Acta Crystallographica Section D: Biological Crystallography* 55.12 (1999): 2037-2038.
Hancock, Robert EW, and Hans-Georg Sahl. "Antimicrobial and host-defense peptides as new anti-infective therapeutic strategies." *Nature biotechnology* 24.12 (2006): 1551.
Ibrahim, Hisham Radwan, et al. "Enhanced bactericidal action of lysozyme to *Escherichia coli* by inserting a hydrophobic pentapeptide into its C terminus." *Journal of Biological Chemistry* 269.7(1994): 5059-5063.
ICN 2000-2001 catalogue for Cell Culture, p. 41, print 2000.
Ito, Yoshihiro, et al. "Bactericidal activity of human lysozymes carrying various lengths of polyproline chain at the C-terminus," *FEBS letters* 415.3 (1997): 285-288.
Jado, Isabel, et al. "Phage lytic enzymes as therapy for antibiotic-resistant *Streptococcus pneumoniae* infection in a murine sepsis model." *Journal of Antimicrobial Chemotherapy*52.6 (2003): 967-973.
JSCE Now, 109:26-28, 2003. [English sequence disclosure only].
Leitch, E. C., and M. D. P. Willcox. "Synergic antistaphylococcal properties of lactoferrin and lysozyme." *Journal of medical microbiology* 47.9 (1998): 837-842.
Li, Qingtian, et al. "Potential therapeutic efficacy of a bactericidal-immunomodulatory fusion peptide against methicillin-resistant *Staphylococcus aureus* skin infection." *Applied microbiology and biotechnology* 86.1 (2010): 305-309.
Loeffler, Jutta M., Daniel Nelson, and Vincent A. Fischetti. "Rapid killing of *Streptococcus pneumoniae* with a bacteriophage cell wall hydrolase." *Science* 294.5549 (2001), 2170-2172.
Loessner, Martin J. "Bacteriophage endolysins—current state of research and applications." *Current opinion in microbiology*8.4 (2005): 480-487.
López, Rubens, Ernesto Garcia, and Pedro Garcia. "Enzymes for anti-infective therapy: phage lysins." *Drug Discovery Today: Therapeutic Strategies* 1.4 (2004): 469-474.
Lu, Xue-mei, et al. "Expression of the antimicrobial peptide cecropin fused with human lysozyme in *Escherichia coli*." *Applied microbiology and biotechnology* 87.6 (2010): 2169-2176.
Manoharadas, Salim, Angela Witte, and Udo Bläsi. "Antimicrobial activity of a chimeric enzybiotic towards *Staphylococcus aureus*." *Journal of biotechnology* 139.1 (2009): 118-123.
Matthews, B. W., and S. J. Remington. "The three dimensional structure of the lysozyme from bacteriophage T4." *Proceedings of the National Academy of Sciences* 71.10 (1974): 4178-4182.

(56) References Cited

OTHER PUBLICATIONS

Melo, Manuel N., Rafael Ferre, and Miguel ARB Castanho. "Antimicrobial peptides: linking partition, activity and high membrane-bound concentrations." *Nature Reviews Microbiology* 7.3 (2009): 245.

Merck KGaA Catalogue, p. 819, print 1996.

Merk, Helmut, et al. "Cell-free expression of two single-chain monoclonal antibodies against lysozyme: effect of domain arrangement on the expression." *The Journal of Biochemistry* 125.2 (1999): 328-333.

Morita, Masatomo, et al. "Functional analysis of antibacterial activity of Bacillus amyloliquefaciens phage endolysin against Gram-negative bacteria." *FEBS letters* 500.1-2 (2001): 56-59.

Muyombwe, Anthony, Yasunori Tanji, and Hajime Unno. "Cloning and expression of a gene encoding the lytic functions of Bacillus amyloliquefaciens phage: evidence of an auxiliary lysis system." *Journal of bioscience and bioengineering* 88.2 (1999): 221-225.

Nakimbugwe, Dorothy, et al. "Cell wall substrate specificity of six different lysozymes and lysozyme inhibitory activity of bacterial extracts." *FEMS microbiology letters* 259.1 (2006): 41-46.

NCBI Blast of Chicken Lysozyme, AAA48943, against all proteins, Jun. 8, 2015.

NCBI Blast of Chicken Lysozyme, AAA48943, against phage proteins, Jun. 8, 2015.

NCBI Blast of Chicken Lysozyme, CAA43320, against all proteins, Jun. 8, 2015.

NCBI Blast of Chicken Lysozyme, CAA43320, against phage proteins, Jun. 8, 2015.

Nelson, Daniel, Lawrence Loomis, and Vincent A. Fischetti. "Prevention and elimination of upper respiratory colonization of mice by group A streptococci by using a bacteriophage lytic enzyme." *Proceedings of the National Academy of Sciences* 98.7 (2001): 4107-4112.

Niu, Mingfu, et al. "The molecular design of a recombinant antimicrobial peptide CP and its in vitro activity." *Protein expression and purification* 57.1 (2008): 95-100.

Office Communication for U.S. Appl. No. 13/380,329, dated Oct. 9, 2013.

Office Communication for U.S. Appl. No. 13/380,329, dated May 2, 2014.

Office Communication for U.S. Appl. No. 13/380,329, dated Dec. 12, 2014.

Office Communication for U.S. Appl. No. 13/380,329, dated Aug. 12, 2015.

Oncor Appligene 1996-1997 Catalogue, p. 201, print 1996.

Orito, Y., et al. "Bacillus amyloliquefaciens phage endolysin can enhance permeability of Pseudomonas aeruginosa outer membrane and induce cell lysis." *Applied microbiology and biotechnology* 65.1 (2004): 105-109.

Park, In Yup, et al. "Parasin I, an antimicrobial peptide derived from histone H2A in the catfish, Parasilurus asotus." *FEBS letters* 437.3 (1998): 258-262.

Park, Taehyun, et al. "Topological dynamics of holins in programmed bacterial lysis." *Proceedings of the National Academy of Sciences* 103.52 (2006): 19713-19718.

PCT International Preliminary Report on Patentability issued in International application No. PCT/EP2010/059152, dated Jan. 12, 2012.

PCT International Search Report and Written Opinion issued in International application No. PCT/EP2010/059152, dated Nov. 12, 2010.

Powers, Jon-Paul S., and Robert EW Hancock. "The relationship between peptide structure and antibacterial activity." *Peptides* 24.11 (2003): 1681-1691.

Rashel, Mohammad, et al. "Efficient elimination of multidrug-resistant Staphylococcus aureus by cloned lysin derived from bacteriophage ϕMR11." *The Journal of infectious diseases* 196.8 (2007): 1237-1247.

Reimann, C. T., et al. "Proteins in vacuo: a molecular dynamics study of the unfolding behavior of highly charged disulfide-bond-intact lysozyme subjected to a temperature pulse." *Physical Review E* 60.6 (1999): 7277.

Ruckenstein, Eli, and Xianfang Zeng. "Macroporous chitin affinity membranes for lysozyme separation." *Biotechnology and bioengineering* 56.6 (1997): 610-617.

Sanz, Jesús M., and José L. Garcia. "Structural studies of the lysozyme coded by the pneumococcal phage Cp-1: Conformational changes induced by choline." *European journal of biochemistry* 187.2 (1990): 409-416.

Schuch, Raymond, Daniel Nelson, and Vincent A. Fischetti. "A bacteriolytic agent that detects and kills Bacillus anthracis." *Nature* 418.6900 (2002): 884.

Tack, Brian F., et al. "SMAP-29 has two LPS-binding sites and a central hinge." *European journal of biochemistry* 269.4 (2002): 1181-1189.

Tan, Nguan Soon, et al. "Definition of endotoxin binding sites in horseshoe crab factor C recombinant sushi proteins and neutralization of endotoxin by sushi peptides." *The FASEB Journal* 14.12 (2000): 1801-1813.

Terpe, K. "Overview of tag protein fusions: from molecular and biochemical fundamentals to commercial systems." *Applied microbiology and biotechnology* 60.5 (2003): 523-533.

UniProt Database, "Lactotransferrin," P02788, 2014.

Van der Linden Danitsja S., et al. "Synergistic effects of ovine-derived cathelicidins and other antimicrobials against *Escherichia coli* O157: H7 and *Staphylococcus aureus* 1056 MRSA." *Biotechnology letters* 31.8 (2009): 1265-1267.

Vollmer, Waldemar, et al. "Bacterial peptidoglycan (murein) hydrolases." *FEMS microbiology reviews* 32.2 (2008): 259-286.

Wilcox, Sara. "The new antimicrobials: cationic peptides." *BioTeach Journal* 2 (2004): 88-91.

Yan, Lizhen, and Michael E. Adams. "Lycotoxins, antimicrobial peptides from venom of the wolf spider *Lycosa carolinensis.*" *Journal of biological chemistry* 273.4 (1998): 2059-2066.

Zasloff, Michael. "Antimicrobial peptides of multicellular organisms." *nature* 415.6870 (2002): 389.

Zhou, Liangfan, et al. "TrxA mediating fusion expression of antimicrobial peptide CM4 from multiple joined genes in *Escherichia coli.*" *Protein expression and purification* 64.2 (2009): 225-230.

Béven, L., and H. Wroblewski. "Effect of natural amphipathic peptides on viability, membrane potential, cell shape and motility of mollicutes." *Research in Microbiology* 148.2 (1997): 163-175. (Abstract).

Brändén, Carl-Ivar, and John Tooze. *Introduction to Protein Structure.* Taylor & Francis, 1999.

Briers, Yves, et al. "The high-affinity peptidoglycan binding domain of Pseudomonas phage endolysin KZ144." *Biochemical and Biophysical Research Communications* 383.2 (2009): 187-191.

Dawson, Raymond M., and Chun-Qiang Liu. "Cathelicidin peptide SMAP-29: comprehensive review of its properties and potential as a novel class of antibiotics." *Drug Development Research* 70.7 (2009): 481-498.

Feng, Xuan, Xiaoyan Yang, and Liujiao Bian. "Construction of the recombinant plasmid expressing a novel fusion protein cecropin B human lysozyme." *Biotechnology* 14.6 (2004): 3-5. (English Abstract).

Fischetti, Vincent A. "Bacteriophage endolysins: a novel anti-infective to control Gram-positive pathogens." *International Journal of Medical Microbiology* 300.6 (2010): 357-362.

Fischetti, Vincent A, "Bacteriophage lysins as effective antibacterials." *Current Opinion in Microbiology* 11.5 (2008): 393-400.

GenBank, Accession No. AAL83045.1, 2002, www.ncbi.nlm.nih.gov.

GenBank, Accession No. AY030242.1, 2001, www.ncbi.nlm.nih.gov.

Graham, Shirley, and Peter J. Coote. "Potent, synergistic inhibition of *Staphylococcus aureus* upon exposure to a combination of the endopeptidase lysostaphin and the cationic peptide ranalexin." *Journal of Antimicrobial Chemotherapy* 59.4 (2007): 759-762.

(56) References Cited

OTHER PUBLICATIONS

Ibrahim, Hisham R., Takayoshi Aoki, and Antonio Pellegrini. "Strategies for new antimicrobial proteins and peptides: lysozyme and aprotinin as model molecules." *Current Pharmaceutical Design* 8.9 (2002): 671-693.

Lowenberger, Carl, et al. "Antimicrobial activity spectrum, cDNA cloning, and mRNA expression of a newly isolated member of the cecropin family from the mosquito vector *Aedes aegypti*." *Journal of Biological Chemistry* 274.29 (1999): 20092-20097.

Maloy, W. Lee, and U. Prasad Kari. "Structure-activity studies on magainins and other host defense peptides," *Biopolymers: Original Research on Biomolecules* 37.2 (1995): 105-122.

Sadowski, M. I., and D. T. Jones. "The sequence-structure relationship and protein function prediction." *Current Opinion in Structural Biology* 19.3 (2009): 357-362.

Seffernick, Jennifer L., et al. "Melamine deaminase and atrazine chlorohydrolase: 98 percent identical but functionally different." *Journal of Bacteriology* 183.8 (2001): 2405-2410.

Steiner, H., et al. "Sequence and specificity of two antibacterial proteins involved in insect immunity." *Nature* 292.5820 (1981): 246.

Stojković, Emina A., and Lucia B. Rothman-Denes. "Coliphage N4 N-acetylmuramidase defines a new family of murein hydrolases." *Journal of Molecular Biology* 366.2 (2007): 406-419.

Tossi, Alessandro, Luca Sandri, and Anna Giangaspero. "Amphipathic, α-helical antimicrobial peptides." *Peptide Science* 55.1 (2000): 4-30.

Witkowski, Andrzej, et al. "Conversion of a β-ketoacyl synthase to a malonyl decarboxylase by replacement of the active-site cysteine with glutamine." *Biochemistry* 38.36 (1999): 11643-11650.

Yan, Hong, and Robert EW Hancock. "Synergistic interactions between mammalian antimicrobial defense peptides." *Antimicrobial agents and chemotherapy* 45.5 (2001): 1558-1560.

Conlon, J. Michael, Milena Mechkarska, and Jay D. King. "Host-defense peptides in skin secretions of African clawed frogs (Xenopodinae, Pipidae)." *General and comparative endocrinology* 176.3 (2012): 513-518.

Deslouches, Berthony, et al. "Activity of the de novo engineered antimicrobial peptide WLBU2 against Pseudomonas aeruginosa in human serum and whole blood: implications for systemic applications." *Antimicrobial agents and chemotherapy* 49.8 (2005): 3208-3216.

Kashani, Hamed Haddad, et al. "Recombinant endolysins as potential therapeutics against antibiotic-resistant *Staphylococcus aureus*: current status of research and novel delivery strategies." *Clinical microbiology reviews* 31.1 (2018): e00071-17.

Wakamatsu, Kaori, et al. "Dimer structure of magainin 2 bound to phospholipid vesicles." *Biopolymers: Original Research on Biomolecules* 64.6 (2002): 314-327.

Zanetti, Margherita, et al. "Cathelicidin peptides as candidates for a novel class of antimicrobials." *Current pharmaceutical design* 8.9 (2002): 779-793.

\* cited by examiner

SEQUENCE LISTING

<160> NUMBER OF SEQ ID NOS: 124

<210> SEQ ID NO 1
<211> LENGTH: 25
<212> TYPE: PRT
<213> ORGANISM: Unknown
<220> FEATURE:
<223> OTHER INFORMATION: amphipatic peptide Pleurocidin

<400> SEQUENCE: 1

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 2
<211> LENGTH: 31
<212> TYPE: PRT
<213> ORGANISM: Unknown
<220> FEATURE:
<223> OTHER INFORMATION: amphipatic peptide Cecropin P1

<400> SEQUENCE: 2

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 3
<211> LENGTH: 21
<212> TYPE: PRT
<213> ORGANISM: Unknown
<220> FEATURE:
<223> OTHER INFORMATION: amphipatic peptide Buforin II

<400> SEQUENCE: 3

Thr Arg Ser Ser Arg Ala Gly Leu Gln Phe Pro Val Gly Arg Val His
1               5                   10                  15

Arg Leu Leu Arg Lys
            20

<210> SEQ ID NO 4
<211> LENGTH: 23
<212> TYPE: PRT
<213> ORGANISM: Unknown
<220> FEATURE:
<223> OTHER INFORMATION: amphipatic peptide Magainin

<400> SEQUENCE: 4

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 5
<211> LENGTH: 37
<212> TYPE: PRT
<213> ORGANISM: Unknown
<220> FEATURE:
<223> OTHER INFORMATION: amphipatic peptides Cathelidicine LL-37

<400> SEQUENCE: 5

Leu Leu Gly Asp Phe Phe Arg Lys Ser Lys Glu Lys Ile Gly Lys Glu
1               5                   10                  15

```
Phe Lys Arg Ile Val Gln Arg Ile Lys Asp Phe Leu Arg Asn Leu Val
            20                  25                  30

Pro Arg Thr Glu Ser
        35

<210> SEQ ID NO 6
<211> LENGTH: 29
<212> TYPE: PRT
<213> ORGANISM: Unknown
<220> FEATURE:
<223> OTHER INFORMATION: SMAP-29

<400> SEQUENCE: 6

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 7
<211> LENGTH: 13
<212> TYPE: PRT
<213> ORGANISM: Unknown
<220> FEATURE:
<223> OTHER INFORMATION: Indolicidin

<400> SEQUENCE: 7

Ile Leu Pro Trp Lys Trp Pro Trp Trp Pro Trp Arg Arg
1               5                   10

<210> SEQ ID NO 8
<211> LENGTH: 18
<212> TYPE: PRT
<213> ORGANISM: Unknown
<220> FEATURE:
<223> OTHER INFORMATION: Protegrin

<400> SEQUENCE: 8

Arg Gly Gly Arg Leu Cys Tyr Cys Arg Arg Arg Phe Cys Val Cys Val
1               5                   10                  15

Gly Arg

<210> SEQ ID NO 9
<211> LENGTH: 36
<212> TYPE: PRT
<213> ORGANISM: Unknown
<220> FEATURE:
<223> OTHER INFORMATION: Cecropin A (A.aegypti)

<400> SEQUENCE: 9

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 10
<211> LENGTH: 40
<212> TYPE: PRT
<213> ORGANISM: Unknown
<220> FEATURE:
<223> OTHER INFORMATION: Cecropin A (D. melanogaster)

<400> SEQUENCE: 10
```

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40

<210> SEQ ID NO 11
<211> LENGTH: 39
<212> TYPE: PRT
<213> ORGANISM: Unknown
<220> FEATURE:
<223> OTHER INFORMATION: Sarcotoxin IA

<400> SEQUENCE: 11

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 12
<211> LENGTH: 5
<212> TYPE: PRT
<213> ORGANISM: Unknown
<220> FEATURE:
<223> OTHER INFORMATION: Synthetic Peptide

<400> SEQUENCE: 12

Phe Phe Val Ala Pro
1               5

<210> SEQ ID NO 13
<211> LENGTH: 9
<212> TYPE: PRT
<213> ORGANISM: Unknown
<220> FEATURE:
<223> OTHER INFORMATION: cationic peptides

<400> SEQUENCE: 13

Lys Arg Lys Lys Arg Lys Lys Arg Lys
1               5

<210> SEQ ID NO 14
<211> LENGTH: 31
<212> TYPE: PRT
<213> ORGANISM: Unknown
<220> FEATURE:
<223> OTHER INFORMATION: cationic peptides

<400> SEQUENCE: 14

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 15
<211> LENGTH: 506
<212> TYPE: PRT
<213> ORGANISM: Unknown
<220> FEATURE:
<223> OTHER INFORMATION: putative lysin [Staphylococcus phage K]

<400> SEQUENCE: 15

```
Met Gly Ser Lys Arg Lys Lys Arg Lys Ala Lys Thr Gln
1               5                   10              15

Ala Glu Ile Asn Lys Arg Leu Asp Ala Tyr Ala Lys Gly Thr Val Asp
                20              25              30

Ser Pro Tyr Arg Val Lys Lys Ala Thr Ser Tyr Asp Pro Ser Phe Gly
            35              40              45

Val Met Glu Ala Gly Ala Ile Asp Ala Asp Gly Tyr Tyr His Ala Gln
        50              55              60

Cys Gln Asp Leu Ile Thr Asp Tyr Val Leu Trp Leu Thr Asp Asn Lys
65              70              75              80

Val Arg Thr Trp Gly Asn Ala Lys Asp Gln Ile Lys Gln Ser Tyr Gly
                85              90              95

Thr Gly Phe Lys Ile His Glu Asn Lys Pro Ser Thr Val Pro Lys Lys
            100             105             110

Gly Trp Ile Ala Val Phe Thr Ser Gly Ser Tyr Glu Gln Trp Gly His
            115             120             125

Ile Gly Ile Val Tyr Asp Gly Gly Asn Thr Ser Thr Phe Thr Ile Leu
        130             135             140

Glu Gln Asn Trp Asn Gly Tyr Ala Asn Lys Lys Pro Thr Lys Arg Val
145             150             155             160

Asp Asn Tyr Tyr Gly Leu Thr His Phe Ile Glu Ile Pro Val Lys Ala
                165             170             175

Gly Thr Thr Val Lys Lys Glu Thr Ala Lys Lys Ser Ala Ser Lys Thr
            180             185             190

Pro Ala Pro Lys Lys Ala Thr Leu Lys Val Ser Lys Asn His Ile
            195             200             205

Asn Tyr Thr Met Asp Lys Arg Gly Lys Lys Pro Glu Gly Met Val Ile
        210             215             220

His Asn Asp Ala Gly Arg Ser Ser Gly Gln Gln Tyr Glu Asn Ser Leu
225             230             235             240

Ala Asn Ala Gly Tyr Ala Arg Tyr Ala Asn Gly Ile Ala His Tyr Tyr
                245             250             255

Gly Ser Glu Gly Tyr Val Trp Glu Ala Ile Asp Ala Lys Asn Gln Ile
            260             265             270

Ala Trp His Thr Gly Asp Gly Thr Gly Ala Asn Ser Gly Asn Phe Arg
        275             280             285

Phe Ala Gly Ile Glu Val Cys Gln Ser Met Ser Ala Ser Asp Ala Gln
290             295             300

Phe Leu Lys Asn Glu Gln Ala Val Phe Gln Phe Thr Ala Glu Lys Phe
305             310             315             320

Lys Glu Trp Gly Leu Thr Pro Asn Arg Lys Thr Val Arg Leu His Met
                325             330             335

Glu Phe Val Pro Thr Ala Cys Pro His Arg Ser Met Val Leu His Thr
            340             345             350

Gly Phe Asn Pro Val Thr Gln Gly Arg Pro Ser Gln Ala Ile Met Asn
        355             360             365

Lys Leu Lys Asp Tyr Phe Ile Lys Gln Ile Lys Asn Tyr Met Asp Lys
370             375             380

Gly Thr Ser Ser Ser Thr Val Val Lys Asp Gly Lys Thr Ser Ser Ala
385             390             395             400

Ser Thr Pro Ala Thr Arg Pro Val Thr Gly Ser Trp Lys Lys Asn Gln
            405             410             415
```

```
Tyr Gly Thr Trp Tyr Lys Pro Glu Asn Ala Thr Phe Val Asn Gly Asn
            420                 425                 430

Gln Pro Ile Val Thr Arg Ile Gly Ser Pro Phe Leu Asn Ala Pro Val
        435                 440                 445

Gly Gly Asn Leu Pro Ala Gly Ala Thr Ile Val Tyr Asp Glu Val Cys
    450                 455                 460

Ile Gln Ala Gly His Ile Trp Ile Gly Tyr Asn Ala Tyr Asn Gly Asn
465                 470                 475                 480

Arg Val Tyr Cys Pro Val Arg Thr Cys Gln Gly Val Pro Pro Asn Gln
                485                 490                 495

Ile Pro Gly Val Ala Trp Gly Val Phe Lys
            500                 505

<210> SEQ ID NO 16
<211> LENGTH: 528
<212> TYPE: PRT
<213> ORGANISM: Unknown
<220> FEATURE:
<223> OTHER INFORMATION: Putative Lysin Staphylococcus phage K

<400> SEQUENCE: 16

Met Gly Ser Lys Arg Lys Lys Arg Lys Lys Arg Lys Ser Lys Arg
1               5                   10                  15

Lys Lys Arg Lys Lys Arg Lys Arg Ser Lys Arg Lys Lys Arg Lys Lys
            20                  25                  30

Arg Lys Ala Lys Thr Gln Ala Glu Ile Asn Lys Arg Leu Asp Ala Tyr
        35                  40                  45

Ala Lys Gly Thr Val Asp Ser Pro Tyr Arg Val Lys Lys Ala Thr Ser
    50                  55                  60

Tyr Asp Pro Ser Phe Gly Val Met Glu Ala Gly Ala Ile Asp Ala Asp
65                  70                  75                  80

Gly Tyr Tyr His Ala Gln Cys Gln Asp Leu Ile Thr Asp Tyr Val Leu
                85                  90                  95

Trp Leu Thr Asp Asn Lys Val Arg Thr Trp Gly Asn Ala Lys Asp Gln
            100                 105                 110

Ile Lys Gln Ser Tyr Gly Thr Gly Phe Lys Ile His Glu Asn Lys Pro
        115                 120                 125

Ser Thr Val Pro Lys Lys Gly Trp Ile Ala Val Phe Thr Ser Gly Ser
    130                 135                 140

Tyr Glu Gln Trp Gly His Ile Gly Ile Val Tyr Asp Gly Gly Asn Thr
145                 150                 155                 160

Ser Thr Phe Thr Ile Leu Glu Gln Asn Trp Asn Gly Tyr Ala Asn Lys
                165                 170                 175

Lys Pro Thr Lys Arg Val Asp Asn Tyr Tyr Gly Leu Thr His Phe Ile
            180                 185                 190

Glu Ile Pro Val Lys Ala Gly Thr Thr Val Lys Lys Glu Thr Ala Lys
        195                 200                 205

Lys Ser Ala Ser Lys Thr Pro Ala Pro Lys Lys Ala Thr Leu Lys
    210                 215                 220

Val Ser Lys Asn His Ile Asn Tyr Thr Met Asp Lys Arg Gly Lys Lys
225                 230                 235                 240

Pro Glu Gly Met Val Ile His Asn Asp Ala Gly Arg Ser Ser Gly Gln
                245                 250                 255

Gln Tyr Glu Asn Ser Leu Ala Asn Ala Gly Tyr Ala Arg Tyr Ala Asn
            260                 265                 270
```

```
Gly Ile Ala His Tyr Tyr Gly Ser Glu Gly Tyr Val Trp Glu Ala Ile
            275                 280                 285

Asp Ala Lys Asn Gln Ile Ala Trp His Thr Gly Asp Gly Thr Gly Ala
        290                 295                 300

Asn Ser Gly Asn Phe Arg Phe Ala Gly Ile Glu Val Cys Gln Ser Met
305                 310                 315                 320

Ser Ala Ser Asp Ala Gln Phe Leu Lys Asn Glu Gln Ala Val Phe Gln
                325                 330                 335

Phe Thr Ala Glu Lys Phe Lys Glu Trp Gly Leu Thr Pro Asn Arg Lys
            340                 345                 350

Thr Val Arg Leu His Met Glu Phe Val Pro Thr Ala Cys Pro His Arg
        355                 360                 365

Ser Met Val Leu His Thr Gly Phe Asn Pro Val Thr Gln Gly Arg Pro
    370                 375                 380

Ser Gln Ala Ile Met Asn Lys Leu Lys Asp Tyr Phe Ile Lys Gln Ile
385                 390                 395                 400

Lys Asn Tyr Met Asp Lys Gly Thr Ser Ser Thr Val Val Lys Asp
                405                 410                 415

Gly Lys Thr Ser Ser Ala Ser Thr Pro Ala Thr Arg Pro Val Thr Gly
            420                 425                 430

Ser Trp Lys Lys Asn Gln Tyr Gly Thr Trp Tyr Lys Pro Glu Asn Ala
        435                 440                 445

Thr Phe Val Asn Gly Asn Gln Pro Ile Val Thr Arg Ile Gly Ser Pro
    450                 455                 460

Phe Leu Asn Ala Pro Val Gly Asn Leu Pro Ala Gly Ala Thr Ile
465                 470                 475                 480

Val Tyr Asp Glu Val Cys Ile Gln Ala Gly His Ile Trp Ile Gly Tyr
                485                 490                 495

Asn Ala Tyr Asn Gly Asn Arg Val Tyr Cys Pro Val Arg Thr Cys Gln
            500                 505                 510

Gly Val Pro Pro Asn Gln Ile Pro Gly Val Ala Trp Gly Val Phe Lys
        515                 520                 525

<210> SEQ ID NO 17
<211> LENGTH: 505
<212> TYPE: PRT
<213> ORGANISM: Unknown
<220> FEATURE:
<223> OTHER INFORMATION: Putative Lysin Staphylococcus phage K

<400> SEQUENCE: 17

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110
```

Glu Gln Trp Gly His Ile Gly Ile Val Tyr Asp Gly Asn Thr Ser
            115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
            195                 200                 205

Glu Gly Met Val Ile His Asn Asp Ala Gly Arg Ser Ser Gly Gln Gln
            210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
            275                 280                 285

Ala Ser Asp Ala Gln Phe Leu Lys Asn Glu Gln Ala Val Phe Gln Phe
            290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
            355                 360                 365

Asn Tyr Met Asp Lys Gly Thr Ser Ser Ser Thr Val Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys Ser
                485                 490                 495

Lys Arg Lys Lys Arg Lys Lys Arg Lys
            500                 505

<210> SEQ ID NO 18
<211> LENGTH: 527
<212> TYPE: PRT

<213> ORGANISM: Unknown
<220> FEATURE:
<223> OTHER INFORMATION: Putative Lysin Staphylococcus phage K

<400> SEQUENCE: 18

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Ala Asp Asp Gly
        35                  40                  45

Tyr Tyr His Ala Gln Cys Gln Asp Leu Ile Thr Asp Tyr Val Leu Trp
50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
            195                 200                 205

Glu Gly Met Val Ile His Asn Asp Ala Gly Arg Ser Ser Gly Gln Gln
        210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Val Lys Asp Gly
370                 375                 380

Lys Thr Ser Ser Ala Ser Thr Pro Ala Thr Arg Pro Val Thr Gly Ser
```

```
                385                 390                 395                 400
Trp Lys Lys Asn Gln Tyr Gly Thr Trp Tyr Lys Pro Glu Asn Ala Thr
                    405                 410                 415

Phe Val Asn Gly Asn Gln Pro Ile Val Thr Arg Ile Gly Ser Pro Phe
                420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
        450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys Ser
                485                 490                 495

Lys Arg Lys Lys Arg Lys Lys Arg Lys Ser Lys Arg Lys Lys Arg
                500                 505                 510

Lys Lys Arg Lys Arg Ser Lys Arg Lys Lys Arg Lys Lys Arg Lys
            515                 520                 525

<210> SEQ ID NO 19
<211> LENGTH: 255
<212> TYPE: PRT
<213> ORGANISM: Unknown
<220> FEATURE:
<223> OTHER INFORMATION: Lysostaphin

<400> SEQUENCE: 19

Met Gly Ser Lys Arg Lys Lys Arg Lys Lys His Glu His Ser
1               5                   10                  15

Ala Gln Trp Leu Asn Asn Tyr Lys Lys Gly Tyr Gly Tyr Gly Pro Tyr
                20                  25                  30

Pro Leu Gly Ile Asn Gly Gly Met His Tyr Gly Val Asp Phe Phe Met
            35                  40                  45

Asn Ile Gly Thr Pro Val Lys Ala Ile Ser Ser Gly Lys Ile Val Glu
        50                  55                  60

Ala Gly Trp Ser Asn Tyr Gly Gly Gly Asn Gln Ile Gly Leu Ile Glu
65                  70                  75                  80

Asn Asp Gly Val His Arg Gln Trp Tyr Met His Leu Ser Lys Tyr Asn
                85                  90                  95

Val Lys Val Gly Asp Tyr Val Lys Ala Gly Gln Ile Ile Gly Trp Ser
            100                 105                 110

Gly Ser Thr Gly Tyr Ser Thr Ala Pro His Leu His Phe Gln Arg Met
        115                 120                 125

Val Asn Ser Phe Ser Asn Ser Thr Ala Gln Asp Pro Met Pro Phe Leu
    130                 135                 140

Lys Ser Ala Gly Tyr Gly Lys Ala Gly Gly Thr Val Thr Pro Thr Pro
145                 150                 155                 160

Asn Thr Gly Trp Lys Thr Asn Lys Tyr Gly Thr Leu Tyr Lys Ser Glu
                165                 170                 175

Ser Ala Ser Phe Thr Pro Asn Thr Asp Ile Ile Thr Arg Thr Thr Gly
            180                 185                 190

Pro Phe Arg Ser Met Pro Gln Ser Gly Val Leu Lys Ala Gly Gln Thr
        195                 200                 205

Ile His Tyr Asp Glu Val Met Lys Gln Asp Gly His Val Trp Val Gly
    210                 215                 220

Tyr Thr Gly Asn Ser Gly Gln Arg Ile Tyr Leu Pro Val Arg Thr Trp
```

```
                225                 230                 235                 240

Asn Lys Ser Thr Asn Thr Leu Gly Val Leu Trp Gly Thr Ile Lys
                245                 250                 255

<210> SEQ ID NO 20
<211> LENGTH: 277
<212> TYPE: PRT
<213> ORGANISM: Unknown
<220> FEATURE:
<223> OTHER INFORMATION: Lysostaphin

<400> SEQUENCE: 20

Met Gly Ser Lys Arg Lys Arg Lys Lys Arg Lys Arg Ser Lys Arg
1               5                   10                  15

Lys Lys Arg Lys Lys Arg Lys Arg Ser Lys Arg Lys Lys Arg Lys Lys
                20                  25                  30

Arg Lys His Glu His Ser Ala Gln Trp Leu Asn Asn Tyr Lys Lys Gly
                35                  40                  45

Tyr Gly Tyr Gly Pro Tyr Pro Leu Gly Ile Asn Gly Gly Met His Tyr
50                  55                  60

Gly Val Asp Phe Phe Met Asn Ile Gly Thr Pro Val Lys Ala Ile Ser
65                  70                  75                  80

Ser Gly Lys Ile Val Glu Ala Gly Trp Ser Asn Tyr Gly Gly Gly Asn
                85                  90                  95

Gln Ile Gly Leu Ile Glu Asn Asp Gly Val His Arg Gln Trp Tyr Met
                100                 105                 110

His Leu Ser Lys Tyr Asn Val Lys Val Gly Asp Tyr Val Lys Ala Gly
                115                 120                 125

Gln Ile Ile Gly Trp Ser Gly Ser Thr Gly Tyr Ser Thr Ala Pro His
                130                 135                 140

Leu His Phe Gln Arg Met Val Asn Ser Phe Ser Asn Ser Thr Ala Gln
145                 150                 155                 160

Asp Pro Met Pro Phe Leu Lys Ser Ala Gly Tyr Gly Lys Ala Gly Gly
                165                 170                 175

Thr Val Thr Pro Thr Pro Asn Thr Gly Trp Lys Thr Asn Lys Tyr Gly
                180                 185                 190

Thr Leu Tyr Lys Ser Glu Ser Ala Ser Phe Thr Pro Asn Thr Asp Ile
                195                 200                 205

Ile Thr Arg Thr Thr Gly Pro Phe Arg Ser Met Pro Gln Ser Gly Val
                210                 215                 220

Leu Lys Ala Gly Gln Thr Ile His Tyr Asp Glu Val Met Lys Gln Asp
225                 230                 235                 240

Gly His Val Trp Val Gly Tyr Thr Gly Asn Ser Gly Gln Arg Ile Tyr
                245                 250                 255

Leu Pro Val Arg Thr Trp Asn Lys Ser Thr Asn Thr Leu Gly Val Leu
                260                 265                 270

Trp Gly Thr Ile Lys
        275

<210> SEQ ID NO 21
<211> LENGTH: 254
<212> TYPE: PRT
<213> ORGANISM: Unknown
<220> FEATURE:
<223> OTHER INFORMATION: Lysostaphin

<400> SEQUENCE: 21
```

```
Met His Glu His Ser Ala Gln Trp Leu Asn Asn Tyr Lys Lys Gly Tyr
1               5                   10                  15

Gly Tyr Gly Pro Tyr Pro Leu Gly Ile Asn Gly Gly Met His Tyr Gly
            20                  25                  30

Val Asp Phe Phe Met Asn Ile Gly Thr Pro Val Lys Ala Ile Ser Ser
        35                  40                  45

Gly Lys Ile Val Glu Ala Gly Trp Ser Asn Tyr Gly Gly Gly Asn Gln
50                  55                  60

Ile Gly Leu Ile Glu Asn Asp Gly Val His Arg Gln Trp Tyr Met His
65                  70                  75                  80

Leu Ser Lys Tyr Asn Val Lys Val Gly Asp Tyr Val Lys Ala Gly Gln
                85                  90                  95

Ile Ile Gly Trp Ser Gly Ser Thr Gly Tyr Ser Thr Ala Pro His Leu
                100                 105                 110

His Phe Gln Arg Met Val Asn Ser Phe Ser Asn Ser Thr Ala Gln Asp
            115                 120                 125

Pro Met Pro Phe Leu Lys Ser Ala Gly Tyr Gly Lys Ala Gly Gly Thr
    130                 135                 140

Val Thr Pro Thr Pro Asn Thr Gly Trp Lys Thr Asn Lys Tyr Gly Thr
145                 150                 155                 160

Leu Tyr Lys Ser Glu Ser Ala Ser Phe Thr Pro Asn Thr Asp Ile Ile
                165                 170                 175

Thr Arg Thr Thr Gly Pro Phe Arg Ser Met Pro Gln Ser Gly Val Leu
            180                 185                 190

Lys Ala Gly Gln Thr Ile His Tyr Asp Glu Val Met Lys Gln Asp Gly
        195                 200                 205

His Val Trp Val Gly Tyr Thr Gly Asn Ser Gly Gln Arg Ile Tyr Leu
    210                 215                 220

Pro Val Arg Thr Trp Asn Lys Ser Thr Asn Thr Leu Gly Val Leu Trp
225                 230                 235                 240

Gly Thr Ile Lys Ser Lys Arg Lys Lys Arg Lys
                245                 250

<210> SEQ ID NO 22
<211> LENGTH: 276
<212> TYPE: PRT
<213> ORGANISM: Unknown
<220> FEATURE:
<223> OTHER INFORMATION: Lysostaphin

<400> SEQUENCE: 22

Met His Glu His Ser Ala Gln Trp Leu Asn Asn Tyr Lys Lys Gly Tyr
1               5                   10                  15

Gly Tyr Gly Pro Tyr Pro Leu Gly Ile Asn Gly Gly Met His Tyr Gly
            20                  25                  30

Val Asp Phe Phe Met Asn Ile Gly Thr Pro Val Lys Ala Ile Ser Ser
        35                  40                  45

Gly Lys Ile Val Glu Ala Gly Trp Ser Asn Tyr Gly Gly Gly Asn Gln
50                  55                  60

Ile Gly Leu Ile Glu Asn Asp Gly Val His Arg Gln Trp Tyr Met His
65                  70                  75                  80

Leu Ser Lys Tyr Asn Val Lys Val Gly Asp Tyr Val Lys Ala Gly Gln
                85                  90                  95

Ile Ile Gly Trp Ser Gly Ser Thr Gly Tyr Ser Thr Ala Pro His Leu
                100                 105                 110
```

```
His Phe Gln Arg Met Val Asn Ser Phe Ser Asn Ser Thr Ala Gln Asp
            115                 120                 125
Pro Met Pro Phe Leu Lys Ser Ala Gly Tyr Gly Lys Ala Gly Gly Thr
        130                 135                 140
Val Thr Pro Thr Pro Asn Thr Gly Trp Lys Thr Asn Lys Tyr Gly Thr
145                 150                 155                 160
Leu Tyr Lys Ser Glu Ser Ala Ser Phe Thr Pro Asn Thr Asp Ile Ile
                165                 170                 175
Thr Arg Thr Thr Gly Pro Phe Arg Ser Met Pro Gln Ser Gly Val Leu
            180                 185                 190
Lys Ala Gly Gln Thr Ile His Tyr Asp Glu Val Met Lys Gln Asp Gly
        195                 200                 205
His Val Trp Val Gly Tyr Thr Gly Asn Ser Gly Gln Arg Ile Tyr Leu
    210                 215                 220
Pro Val Arg Thr Trp Asn Lys Ser Thr Asn Thr Leu Gly Val Leu Trp
225                 230                 235                 240
Gly Thr Ile Lys Ser Lys Arg Lys Lys Arg Lys Lys Arg Lys Arg Ser
                245                 250                 255
Lys Arg Lys Lys Arg Lys Arg Lys Arg Ser Lys Arg Lys Lys Lys Arg
            260                 265                 270
Lys Lys Arg Lys
        275

<210> SEQ ID NO 23
<211> LENGTH: 39
<212> TYPE: PRT
<213> ORGANISM: Unknown
<220> FEATURE:
<223> OTHER INFORMATION: Buforin I

<400> SEQUENCE: 23

Ala Gly Arg Gly Lys Gln Gly Gly Lys Val Arg Ala Lys Ala Lys Thr
1               5                   10                  15
Arg Ser Ser Arg Ala Gly Leu Gln Phe Pro Val Gly Arg Val His Arg
            20                  25                  30
Leu Leu Arg Lys Gly Asn Tyr
        35

<210> SEQ ID NO 24
<211> LENGTH: 6
<212> TYPE: PRT
<213> ORGANISM: Unknown
<220> FEATURE:
<223> OTHER INFORMATION: peptide stretch

<400> SEQUENCE: 24

Lys Arg Lys Lys Arg Lys
1               5

<210> SEQ ID NO 25
<211> LENGTH: 9
<212> TYPE: PRT
<213> ORGANISM: Unknown
<220> FEATURE:
<223> OTHER INFORMATION: peptide stretch

<400> SEQUENCE: 25

Arg Arg Arg Arg Arg Arg Arg Arg Arg
1               5
```

```
<210> SEQ ID NO 26
<211> LENGTH: 8
<212> TYPE: PRT
<213> ORGANISM: Unknown
<220> FEATURE:
<223> OTHER INFORMATION: peptide stretch

<400> SEQUENCE: 26

Lys Lys Lys Lys Lys Lys Lys Lys
1               5

<210> SEQ ID NO 27
<211> LENGTH: 10
<212> TYPE: PRT
<213> ORGANISM: Unknown
<220> FEATURE:
<223> OTHER INFORMATION: peptide stretch

<400> SEQUENCE: 27

Lys Arg Lys Lys Arg Lys Lys Arg Lys Lys
1               5                   10

<210> SEQ ID NO 28
<211> LENGTH: 12
<212> TYPE: PRT
<213> ORGANISM: Unknown
<220> FEATURE:
<223> OTHER INFORMATION: peptide stretch

<400> SEQUENCE: 28

Lys Arg Lys Lys Arg Lys Lys Arg Lys Lys Arg Lys
1               5                   10

<210> SEQ ID NO 29
<211> LENGTH: 14
<212> TYPE: PRT
<213> ORGANISM: Unknown
<220> FEATURE:
<223> OTHER INFORMATION: peptide stretch

<400> SEQUENCE: 29

Lys Arg Lys Lys Arg Lys Lys Arg Lys Lys Arg Lys Lys Arg
1               5                   10

<210> SEQ ID NO 30
<211> LENGTH: 16
<212> TYPE: PRT
<213> ORGANISM: Unknown
<220> FEATURE:
<223> OTHER INFORMATION: peptide stretch

<400> SEQUENCE: 30

Lys Lys Lys Lys Lys Lys Lys Lys Lys Lys Lys Lys Lys Lys Lys Lys
1               5                   10                  15

<210> SEQ ID NO 31
<211> LENGTH: 18
<212> TYPE: PRT
<213> ORGANISM: Unknown
<220> FEATURE:
<223> OTHER INFORMATION: peptide stretch

<400> SEQUENCE: 31

Lys Arg Lys Lys Arg Lys Lys Arg Lys Lys Arg Lys Lys Arg Lys Lys
1               5                   10                  15

Arg Lys
```

-continued

<210> SEQ ID NO 32
<211> LENGTH: 19
<212> TYPE: PRT
<213> ORGANISM: Unknown
<220> FEATURE:
<223> OTHER INFORMATION: peptide stretch

<400> SEQUENCE: 32

```
Lys Arg Lys Lys Arg Lys Lys Arg Lys Lys Arg Lys Lys Arg Lys Lys
1               5                   10                  15

Arg Lys Lys
```

<210> SEQ ID NO 33
<211> LENGTH: 19
<212> TYPE: PRT
<213> ORGANISM: Unknown
<220> FEATURE:
<223> OTHER INFORMATION: peptide stretch

<400> SEQUENCE: 33

```
Arg Arg Arg Arg Arg Arg Arg Arg Arg Arg Arg Arg Arg Arg Arg Arg
1               5                   10                  15

Arg Arg Arg
```

<210> SEQ ID NO 34
<211> LENGTH: 19
<212> TYPE: PRT
<213> ORGANISM: Unknown
<220> FEATURE:
<223> OTHER INFORMATION: peptide stretch

<400> SEQUENCE: 34

```
Lys Lys Lys Lys Lys Lys Lys Lys Lys Lys Lys Lys Lys Lys Lys Lys
1               5                   10                  15

Lys Lys Lys
```

<210> SEQ ID NO 35
<211> LENGTH: 20
<212> TYPE: PRT
<213> ORGANISM: Unknown
<220> FEATURE:
<223> OTHER INFORMATION: peptide stretch

<400> SEQUENCE: 35

```
Lys Arg Lys Lys Arg Lys Lys Arg Lys Arg Ser Lys Arg Lys Lys Arg
1               5                   10                  15

Lys Lys Arg Lys
            20
```

<210> SEQ ID NO 36
<211> LENGTH: 21
<212> TYPE: PRT
<213> ORGANISM: Unknown
<220> FEATURE:
<223> OTHER INFORMATION: peptide stretch

<400> SEQUENCE: 36

```
Lys Arg Lys Lys Arg Lys Lys Arg Lys Arg Ser Lys Arg Lys Lys Arg
1               5                   10                  15

Lys Lys Arg Lys Lys
            20
```

<210> SEQ ID NO 37

```
<211> LENGTH: 21
<212> TYPE: PRT
<213> ORGANISM: Unknown
<220> FEATURE:
<223> OTHER INFORMATION: peptide stretch

<400> SEQUENCE: 37

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 38
<211> LENGTH: 22
<212> TYPE: PRT
<213> ORGANISM: Unknown
<220> FEATURE:
<223> OTHER INFORMATION: peptide stretch

<400> SEQUENCE: 38

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 39
<211> LENGTH: 24
<212> TYPE: PRT
<213> ORGANISM: Unknown
<220> FEATURE:
<223> OTHER INFORMATION: peptide stretch

<400> SEQUENCE: 39

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 40
<211> LENGTH: 25
<212> TYPE: PRT
<213> ORGANISM: Unknown
<220> FEATURE:
<223> OTHER INFORMATION: peptide stretch

<400> SEQUENCE: 40

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 41
<211> LENGTH: 31
<212> TYPE: PRT
<213> ORGANISM: Unknown
<220> FEATURE:
<223> OTHER INFORMATION: peptide stretch

<400> SEQUENCE: 41

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30
```

```
<210> SEQ ID NO 42
<211> LENGTH: 38
<212> TYPE: PRT
<213> ORGANISM: Unknown
<220> FEATURE:
<223> OTHER INFORMATION: peptide stretch

<400> SEQUENCE: 42

Lys Arg Lys Lys Arg Lys Lys Arg Lys Arg Gly Ser Gly Ser Gly Lys
1               5                   10                  15
Arg Lys Lys Arg Lys Lys Arg Lys Gly Ser Gly Ser Gly Lys Arg Lys
            20                  25                  30
Lys Arg Lys Lys Arg Lys
        35

<210> SEQ ID NO 43
<211> LENGTH: 39
<212> TYPE: PRT
<213> ORGANISM: Unknown
<220> FEATURE:
<223> OTHER INFORMATION: peptide stretch

<400> SEQUENCE: 43

Lys Arg Lys Lys Arg Lys Lys Arg Lys Lys Arg Lys Lys Arg Lys Lys
1               5                   10                  15
Arg Lys Lys Arg Lys Lys Arg Lys Lys Arg Lys Lys Arg Lys Lys Arg
            20                  25                  30
Lys Lys Arg Lys Lys Arg Lys
        35

<210> SEQ ID NO 44
<211> LENGTH: 42
<212> TYPE: PRT
<213> ORGANISM: Unknown
<220> FEATURE:
<223> OTHER INFORMATION: peptide stretch

<400> SEQUENCE: 44

Lys Arg Lys Lys Arg Lys Lys Arg Lys Arg Ser Lys Arg Lys Lys Arg
1               5                   10                  15
Lys Lys Arg Lys Arg Ser Lys Arg Lys Lys Arg Lys Lys Arg Lys Arg
            20                  25                  30
Ser Lys Arg Lys Lys Arg Lys Lys Arg Lys
        35                  40

<210> SEQ ID NO 45
<211> LENGTH: 5
<212> TYPE: PRT
<213> ORGANISM: Unknown
<220> FEATURE:
<223> OTHER INFORMATION: motif for polypeptide stretches, wherein X is
      any other amino acid than lysine, arginine and histidine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 45

Lys Arg Xaa Lys Arg
1               5

<210> SEQ ID NO 46
<211> LENGTH: 5
<212> TYPE: PRT
<213> ORGANISM: Unknown
```

```
<220> FEATURE:
<223> OTHER INFORMATION: motif for polypeptide stretches

<400> SEQUENCE: 46

Lys Arg Ser Lys Arg
1               5

<210> SEQ ID NO 47
<211> LENGTH: 5
<212> TYPE: PRT
<213> ORGANISM: Unknown
<220> FEATURE:
<223> OTHER INFORMATION: motif for polypeptide stretches

<400> SEQUENCE: 47

Lys Arg Gly Ser Gly
1               5

<210> SEQ ID NO 48
<211> LENGTH: 22
<212> TYPE: PRT
<213> ORGANISM: Unknown
<220> FEATURE:
<223> OTHER INFORMATION: Nigrocine 2

<400> SEQUENCE: 48

Gly Leu Leu Ser Lys Val Leu Gly Val Gly Lys Lys Val Leu Cys Gly
1               5                   10                  15

Val Ser Gly Leu Val Cys
            20

<210> SEQ ID NO 49
<211> LENGTH: 24
<212> TYPE: PRT
<213> ORGANISM: Unknown
<220> FEATURE:
<223> OTHER INFORMATION: Ascaphine 5

<400> SEQUENCE: 49

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 50
<211> LENGTH: 17
<212> TYPE: PRT
<213> ORGANISM: Unknown
<220> FEATURE:
<223> OTHER INFORMATION: Apidaecine

<400> SEQUENCE: 50

Ala Asn Arg Pro Val Tyr Ile Pro Pro Pro Arg Pro Pro His Pro Arg
1               5                   10                  15

Leu

<210> SEQ ID NO 51
<211> LENGTH: 24
<212> TYPE: PRT
<213> ORGANISM: Unknown
<220> FEATURE:
<223> OTHER INFORMATION: Pseudin 1

<400> SEQUENCE: 51

Gly Leu Asn Thr Leu Lys Lys Val Phe Gln Gly Leu His Glu Ala Ile
```

```
1               5                   10                  15
Lys Leu Ile Asn Asn His Val Gln
            20

<210> SEQ ID NO 52
<211> LENGTH: 18
<212> TYPE: PRT
<213> ORGANISM: Unknown
<220> FEATURE:
<223> OTHER INFORMATION: Ranalexin

<400> SEQUENCE: 52

Phe Leu Gly Gly Leu Ile Val Pro Ala Met Ile Cys Ala Val Thr Lys
1               5                   10                  15

Lys Cys

<210> SEQ ID NO 53
<211> LENGTH: 26
<212> TYPE: PRT
<213> ORGANISM: Unknown
<220> FEATURE:
<223> OTHER INFORMATION: Melittin

<400> SEQUENCE: 53

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 54
<211> LENGTH: 34
<212> TYPE: PRT
<213> ORGANISM: Unknown
<220> FEATURE:
<223> OTHER INFORMATION: Sushi 1 peptide

<400> SEQUENCE: 54

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 55
<211> LENGTH: 27
<212> TYPE: PRT
<213> ORGANISM: Unknown
<220> FEATURE:
<223> OTHER INFORMATION: WLBU2-Variant

<400> SEQUENCE: 55

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 56
<211> LENGTH: 18
<212> TYPE: PRT
<213> ORGANISM: Unknown
<220> FEATURE:
<223> OTHER INFORMATION: Walmagh1

<400> SEQUENCE: 56
```

Gly Phe Phe Ile Pro Ala Val Ile Leu Pro Ser Ile Ala Phe Leu Ile
1               5                   10                  15

Val Pro

<210> SEQ ID NO 57
<211> LENGTH: 339
<212> TYPE: PRT
<213> ORGANISM: Unknown
<220> FEATURE:
<223> OTHER INFORMATION: Cpl-1

<400> SEQUENCE: 57

Met Val Lys Lys Asn Asp Leu Phe Val Asp Val Ser Ser His Asn Gly
1               5                   10                  15

Tyr Asp Ile Thr Gly Ile Leu Glu Gln Met Gly Thr Thr Asn Thr Ile
                20                  25                  30

Ile Lys Ile Ser Glu Ser Thr Thr Tyr Leu Asn Pro Cys Leu Ser Ala
            35                  40                  45

Gln Val Glu Gln Ser Asn Pro Ile Gly Phe Tyr His Phe Ala Arg Phe
    50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
    115                 120                 125

Pro Phe Thr His Asp Asn Val Asp Tyr Gln Gln Ile Leu Ala Gln Phe
130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
    195                 200                 205

Trp Trp Phe Arg Arg Asn Asn Gly Ser Phe Pro Tyr Asn Lys Trp Glu
210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
    275                 280                 285

Asn Asn Trp Tyr Tyr Met Thr Asn Glu Arg Gly Asn Met Val Ser Asn
290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

-continued

Thr Val Ala

<210> SEQ ID NO 58
<211> LENGTH: 341
<212> TYPE: PRT
<213> ORGANISM: Unknown
<220> FEATURE:
<223> OTHER INFORMATION: Ply511

<400> SEQUENCE: 58

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340

<210> SEQ ID NO 59
<211> LENGTH: 495
<212> TYPE: PRT
<213> ORGANISM: Unknown
<220> FEATURE:
<223> OTHER INFORMATION: LysK

<400> SEQUENCE: 59

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Val Lys Asp Gly
```

```
                    370                 375                 380
Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                    405                 410                 415

Phe Val Asn Gly Asn Gln Pro Ile Val Thr Arg Ile Gly Ser Pro Phe
                420                 425                 430

Leu Asn Ala Pro Val Gly Gly Asn Leu Pro Ala Gly Ala Thr Ile Val
            435                 440                 445

Tyr Asp Glu Val Cys Ile Gln Ala Gly His Ile Trp Ile Gly Tyr Asn
        450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495

<210> SEQ ID NO 60
<211> LENGTH: 245
<212> TYPE: PRT
<213> ORGANISM: Unknown
<220> FEATURE:
<223> OTHER INFORMATION: Lysostaphin

<400> SEQUENCE: 60

Met Ala His Glu His Ser Ala Gln Trp Leu Asn Asn Tyr Lys Lys Gly
1               5                   10                  15

Tyr Gly Tyr Gly Pro Tyr Pro Leu Gly Ile Asn Gly Gly Met His Tyr
            20                  25                  30

Gly Val Asp Phe Phe Met Asn Ile Gly Thr Pro Val Lys Ala Ile Ser
        35                  40                  45

Ser Gly Lys Ile Val Glu Ala Gly Trp Ser Asn Tyr Gly Gly Gly Asn
    50                  55                  60

Gln Ile Gly Leu Ile Glu Asn Asp Gly Val His Arg Gln Trp Tyr Met
65                  70                  75                  80

His Leu Ser Lys Tyr Asn Val Lys Val Gly Asp Tyr Val Lys Ala Gly
                85                  90                  95

Gln Ile Ile Gly Trp Ser Gly Ser Thr Gly Tyr Ser Thr Ala Pro His
            100                 105                 110

Leu His Phe Gln Arg Met Val Asn Ser Phe Ser Asn Ser Thr Ala Gln
        115                 120                 125

Asp Pro Met Pro Phe Leu Lys Ser Ala Gly Tyr Gly Lys Ala Gly Gly
    130                 135                 140

Thr Val Thr Pro Thr Pro Asn Thr Gly Trp Lys Thr Asn Lys Tyr Gly
145                 150                 155                 160

Thr Leu Tyr Lys Ser Glu Ser Ala Ser Phe Thr Pro Asn Thr Asp Ile
                165                 170                 175

Ile Thr Arg Thr Thr Gly Pro Phe Arg Ser Met Pro Gln Ser Gly Val
            180                 185                 190

Leu Lys Ala Gly Gln Thr Ile His Tyr Asp Glu Val Met Lys Gln Asp
        195                 200                 205

Gly His Val Trp Val Gly Tyr Thr Gly Asn Ser Gly Gln Arg Ile Tyr
    210                 215                 220

Leu Pro Val Arg Thr Trp Asn Lys Ser Thr Asn Thr Leu Gly Val Leu
225                 230                 235                 240

Trp Gly Thr Ile Lys
                245
```

<210> SEQ ID NO 61
<211> LENGTH: 286
<212> TYPE: PRT
<213> ORGANISM: Unknown
<220> FEATURE:
<223> OTHER INFORMATION: PA6-gp20

<400> SEQUENCE: 61

Met Val Arg Tyr Ile Pro Ala Ala His His Ser Ala Gly Ser Asn Asn
1               5                   10                  15

Pro Val Asn Arg Val Val Ile His Ala Thr Cys Pro Asp Val Gly Phe
            20                  25                  30

Pro Ser Ala Ser Arg Lys Gly Arg Ala Val Ser Thr Ala Asn Tyr Phe
        35                  40                  45

Ala Ser Pro Ser Ser Gly Gly Ser Ala His Tyr Val Cys Asp Ile Gly
    50                  55                  60

Glu Thr Val Gln Cys Leu Ser Glu Ser Thr Ile Gly Trp His Ala Pro
65                  70                  75                  80

Pro Asn Pro His Ser Leu Gly Ile Glu Ile Cys Ala Asp Gly Gly Ser
                85                  90                  95

His Ala Ser Phe Arg Val Pro Gly His Ala Tyr Thr Arg Glu Gln Trp
            100                 105                 110

Leu Asp Pro Gln Val Trp Pro Ala Val Glu Arg Ala Ala Val Leu Cys
        115                 120                 125

Arg Arg Leu Cys Asp Lys Tyr Asn Val Pro Lys Arg Lys Leu Ser Ala
    130                 135                 140

Ala Asp Leu Lys Ala Gly Arg Arg Gly Val Cys Gly His Val Asp Val
145                 150                 155                 160

Thr Asp Ala Trp His Gln Ser Asp His Asp Asp Pro Gly Pro Trp Phe
                165                 170                 175

Pro Trp Asp Lys Phe Met Ala Val Val Asn Gly Gly Ser Gly Asp Ser
            180                 185                 190

Gly Glu Leu Thr Val Ala Asp Val Lys Ala Leu His Asp Gln Ile Lys
        195                 200                 205

Gln Leu Ser Ala Gln Leu Thr Gly Ser Val Asn Lys Leu His His Asp
    210                 215                 220

Val Gly Val Val Gln Val Gln Asn Gly Asp Leu Gly Lys Arg Val Asp
225                 230                 235                 240

Ala Leu Ser Trp Val Lys Asn Pro Val Thr Gly Lys Leu Trp Arg Thr
                245                 250                 255

Lys Asp Ala Leu Trp Ser Val Trp Tyr Tyr Val Leu Glu Cys Arg Ser
            260                 265                 270

Arg Leu Asp Arg Leu Glu Ser Ala Val Asn Asp Leu Lys Lys
        275                 280                 285

<210> SEQ ID NO 62
<211> LENGTH: 6
<212> TYPE: PRT
<213> ORGANISM: Unknown
<220> FEATURE:
<223> OTHER INFORMATION: cationic peptide

<400> SEQUENCE: 62

Lys Arg Lys Lys Arg Lys
1               5

<210> SEQ ID NO 63
<211> LENGTH: 362
<212> TYPE: PRT
<213> ORGANISM: Unknown
<220> FEATURE:
<223> OTHER INFORMATION: Ascaphine5-Cpl1

<400> SEQUENCE: 63

```
Gly Ile Lys Asp Trp Ile Lys Gly Ala Ala Lys Lys Leu Ile Lys Thr
1               5                   10                  15

Val Ala Ser His Ile Ala Asn Gln Val Lys Lys Asn Asp Leu Phe Val
            20                  25                  30

Asp Val Ser Ser His Asn Gly Tyr Asp Ile Thr Gly Ile Leu Glu Gln
        35                  40                  45

Met Gly Thr Thr Asn Thr Ile Ile Lys Ile Ser Glu Ser Thr Thr Tyr
    50                  55                  60

Leu Asn Pro Cys Leu Ser Ala Gln Val Glu Gln Ser Asn Pro Ile Gly
65                  70                  75                  80

Phe Tyr His Phe Ala Arg Phe Gly Gly Asp Val Ala Glu Ala Glu Arg
                85                  90                  95

Glu Ala Gln Phe Phe Leu Asp Asn Val Pro Met Gln Val Lys Tyr Leu
            100                 105                 110

Val Leu Asp Tyr Glu Asp Asp Pro Ser Gly Asp Ala Gln Ala Asn Thr
        115                 120                 125

Asn Ala Cys Leu Arg Phe Met Gln Met Ile Ala Asp Ala Gly Tyr Lys
130                 135                 140

Pro Ile Tyr Tyr Ser Tyr Lys Pro Phe Thr His Asp Asn Val Asp Tyr
145                 150                 155                 160

Gln Gln Ile Leu Ala Gln Phe Pro Asn Ser Leu Trp Ile Ala Gly Tyr
                165                 170                 175

Gly Leu Asn Asp Gly Thr Ala Asn Phe Glu Tyr Phe Pro Ser Met Asp
            180                 185                 190

Gly Ile Arg Trp Trp Gln Tyr Ser Ser Asn Pro Phe Asp Lys Asn Ile
        195                 200                 205

Val Leu Leu Asp Asp Glu Asp Asp Lys Pro Lys Thr Ala Gly Thr
    210                 215                 220

Trp Lys Gln Asp Ser Lys Gly Trp Trp Phe Arg Arg Asn Asn Gly Ser
225                 230                 235                 240

Phe Pro Tyr Asn Lys Trp Glu Lys Ile Gly Gly Val Trp Tyr Tyr Phe
                245                 250                 255

Asp Ser Lys Gly Tyr Cys Leu Thr Ser Glu Trp Leu Lys Asp Asn Glu
            260                 265                 270

Lys Trp Tyr Tyr Leu Lys Asp Asn Gly Ala Met Ala Thr Gly Trp Val
        275                 280                 285

Leu Val Gly Ser Glu Trp Tyr Tyr Met Asp Asp Ser Gly Ala Met Val
    290                 295                 300

Thr Gly Trp Val Lys Tyr Lys Asn Asn Trp Tyr Tyr Met Thr Asn Glu
305                 310                 315                 320

Arg Gly Asn Met Val Ser Asn Glu Phe Ile Lys Ser Gly Lys Gly Trp
                325                 330                 335

Tyr Phe Met Asn Thr Asn Gly Glu Leu Ala Asp Asn Pro Ser Phe Thr
            340                 345                 350

Lys Glu Pro Asp Gly Leu Ile Thr Val Ala
        355                 360
```

<210> SEQ ID NO 64
<211> LENGTH: 355
<212> TYPE: PRT
<213> ORGANISM: Unknown
<220> FEATURE:
<223> OTHER INFORMATION: Apidaecine-Cpl1

<400> SEQUENCE: 64

```
Ala Asn Arg Pro Val Tyr Ile Pro Pro Arg Pro Pro His Pro Arg
1               5                   10                  15

Leu Val Lys Lys Asn Asp Leu Phe Val Asp Val Ser Ser His Asn Gly
                20                  25                  30

Tyr Asp Ile Thr Gly Ile Leu Glu Gln Met Gly Thr Thr Asn Thr Ile
                35                  40                  45

Ile Lys Ile Ser Glu Ser Thr Thr Tyr Leu Asn Pro Cys Leu Ser Ala
50                  55                  60

Gln Val Glu Gln Ser Asn Pro Ile Gly Phe Tyr His Phe Ala Arg Phe
65                  70                  75                  80

Gly Gly Asp Val Ala Glu Ala Glu Arg Glu Ala Gln Phe Phe Leu Asp
                85                  90                  95

Asn Val Pro Met Gln Val Lys Tyr Leu Val Leu Asp Tyr Glu Asp Asp
                100                 105                 110

Pro Ser Gly Asp Ala Gln Ala Asn Thr Asn Ala Cys Leu Arg Phe Met
                115                 120                 125

Gln Met Ile Ala Asp Ala Gly Tyr Lys Pro Ile Tyr Tyr Ser Tyr Lys
130                 135                 140

Pro Phe Thr His Asp Asn Val Asp Tyr Gln Gln Ile Leu Ala Gln Phe
145                 150                 155                 160

Pro Asn Ser Leu Trp Ile Ala Gly Tyr Gly Leu Asn Asp Gly Thr Ala
                165                 170                 175

Asn Phe Glu Tyr Phe Pro Ser Met Asp Gly Ile Arg Trp Trp Gln Tyr
                180                 185                 190

Ser Ser Asn Pro Phe Asp Lys Asn Ile Val Leu Leu Asp Asp Glu Glu
                195                 200                 205

Asp Asp Lys Pro Lys Thr Ala Gly Thr Trp Lys Gln Asp Ser Lys Gly
                210                 215                 220

Trp Trp Phe Arg Arg Asn Asn Gly Ser Phe Pro Tyr Asn Lys Trp Glu
225                 230                 235                 240

Lys Ile Gly Gly Val Trp Tyr Tyr Phe Asp Ser Lys Gly Tyr Cys Leu
                245                 250                 255

Thr Ser Glu Trp Leu Lys Asp Asn Glu Lys Trp Tyr Tyr Leu Lys Asp
                260                 265                 270

Asn Gly Ala Met Ala Thr Gly Trp Val Leu Val Gly Ser Glu Trp Tyr
                275                 280                 285

Tyr Met Asp Asp Ser Gly Ala Met Val Thr Gly Trp Val Lys Tyr Lys
290                 295                 300

Asn Asn Trp Tyr Tyr Met Thr Asn Glu Arg Gly Asn Met Val Ser Asn
305                 310                 315                 320

Glu Phe Ile Lys Ser Gly Lys Gly Trp Tyr Phe Met Asn Thr Asn Gly
                325                 330                 335

Glu Leu Ala Asp Asn Pro Ser Phe Thr Lys Glu Pro Asp Gly Leu Ile
                340                 345                 350

Thr Val Ala
        355
```

<210> SEQ ID NO 65
<211> LENGTH: 360
<212> TYPE: PRT
<213> ORGANISM: Unknown
<220> FEATURE:
<223> OTHER INFORMATION: Nigrocine2-Cpl1

<400> SEQUENCE: 65

Gly Leu Leu Ser Lys Val Leu Gly Val Gly Lys Lys Val Leu Cys Gly
1               5                   10                  15

Val Ser Gly Leu Val Cys Val Lys Lys Asn Asp Leu Phe Val Asp Val
            20                  25                  30

Ser Ser His Asn Gly Tyr Asp Ile Thr Gly Ile Leu Glu Gln Met Gly
        35                  40                  45

Thr Thr Asn Thr Ile Ile Lys Ile Ser Glu Ser Thr Thr Tyr Leu Asn
    50                  55                  60

Pro Cys Leu Ser Ala Gln Val Glu Gln Ser Asn Pro Ile Gly Phe Tyr
65                  70                  75                  80

His Phe Ala Arg Phe Gly Gly Asp Val Ala Glu Ala Glu Arg Glu Ala
                85                  90                  95

Gln Phe Phe Leu Asp Asn Val Pro Met Gln Val Lys Tyr Leu Val Leu
            100                 105                 110

Asp Tyr Glu Asp Asp Pro Ser Gly Asp Ala Gln Ala Asn Thr Asn Ala
        115                 120                 125

Cys Leu Arg Phe Met Gln Met Ile Ala Asp Ala Gly Tyr Lys Pro Ile
    130                 135                 140

Tyr Tyr Ser Tyr Lys Pro Phe Thr His Asp Asn Val Asp Tyr Gln Gln
145                 150                 155                 160

Ile Leu Ala Gln Phe Pro Asn Ser Leu Trp Ile Ala Gly Tyr Gly Leu
                165                 170                 175

Asn Asp Gly Thr Ala Asn Phe Glu Tyr Phe Pro Ser Met Asp Gly Ile
            180                 185                 190

Arg Trp Trp Gln Tyr Ser Ser Asn Pro Phe Asp Lys Asn Ile Val Leu
        195                 200                 205

Leu Asp Asp Glu Glu Asp Lys Pro Lys Thr Ala Gly Thr Trp Lys
    210                 215                 220

Gln Asp Ser Lys Gly Trp Trp Phe Arg Arg Asn Asn Gly Ser Phe Pro
225                 230                 235                 240

Tyr Asn Lys Trp Glu Lys Ile Gly Gly Val Trp Tyr Tyr Phe Asp Ser
                245                 250                 255

Lys Gly Tyr Cys Leu Thr Ser Glu Trp Leu Lys Asp Asn Glu Lys Trp
            260                 265                 270

Tyr Tyr Leu Lys Asp Asn Gly Ala Met Ala Thr Gly Trp Val Leu Val
        275                 280                 285

Gly Ser Glu Trp Tyr Tyr Met Asp Asp Ser Gly Ala Met Val Thr Gly
    290                 295                 300

Trp Val Lys Tyr Lys Asn Asn Trp Tyr Tyr Met Thr Asn Glu Arg Gly
305                 310                 315                 320

Asn Met Val Ser Asn Glu Phe Ile Lys Ser Gly Lys Gly Trp Tyr Phe
                325                 330                 335

Met Asn Thr Asn Gly Glu Leu Ala Asp Asn Pro Ser Phe Thr Lys Glu
            340                 345                 350

Pro Asp Gly Leu Ile Thr Val Ala
        355                 360

<210> SEQ ID NO 66
<211> LENGTH: 362
<212> TYPE: PRT
<213> ORGANISM: Unknown
<220> FEATURE:
<223> OTHER INFORMATION: Pseudin1-Cpl1

<400> SEQUENCE: 66

Gly Leu Asn Thr Leu Lys Lys Val Phe Gln Gly Leu His Glu Ala Ile
1               5                   10                  15

Lys Leu Ile Asn Asn His Val Gln Val Lys Lys Asn Asp Leu Phe Val
            20                  25                  30

Asp Val Ser Ser His Asn Gly Tyr Asp Ile Thr Gly Ile Leu Glu Gln
        35                  40                  45

Met Gly Thr Thr Asn Thr Ile Ile Lys Ile Ser Glu Ser Thr Thr Tyr
    50                  55                  60

Leu Asn Pro Cys Leu Ser Ala Gln Val Glu Gln Ser Asn Pro Ile Gly
65                  70                  75                  80

Phe Tyr His Phe Ala Arg Phe Gly Gly Asp Val Ala Glu Ala Glu Arg
                85                  90                  95

Glu Ala Gln Phe Phe Leu Asp Asn Val Pro Met Gln Val Lys Tyr Leu
            100                 105                 110

Val Leu Asp Tyr Glu Asp Asp Pro Ser Gly Asp Ala Gln Ala Asn Thr
        115                 120                 125

Asn Ala Cys Leu Arg Phe Met Gln Met Ile Ala Asp Ala Gly Tyr Lys
130                 135                 140

Pro Ile Tyr Tyr Ser Tyr Lys Pro Phe Thr His Asp Asn Val Asp Tyr
145                 150                 155                 160

Gln Gln Ile Leu Ala Gln Phe Pro Asn Ser Leu Trp Ile Ala Gly Tyr
                165                 170                 175

Gly Leu Asn Asp Gly Thr Ala Asn Phe Glu Tyr Phe Pro Ser Met Asp
            180                 185                 190

Gly Ile Arg Trp Trp Gln Tyr Ser Ser Asn Pro Phe Asp Lys Asn Ile
        195                 200                 205

Val Leu Leu Asp Asp Glu Asp Asp Lys Pro Lys Thr Ala Gly Thr
210                 215                 220

Trp Lys Gln Asp Ser Lys Gly Trp Trp Phe Arg Arg Asn Asn Gly Ser
225                 230                 235                 240

Phe Pro Tyr Asn Lys Trp Glu Lys Ile Gly Gly Val Trp Tyr Tyr Phe
                245                 250                 255

Asp Ser Lys Gly Tyr Cys Leu Thr Ser Glu Trp Leu Lys Asp Asn Glu
            260                 265                 270

Lys Trp Tyr Tyr Leu Lys Asp Asn Gly Ala Met Ala Thr Gly Trp Val
        275                 280                 285

Leu Val Gly Ser Glu Trp Tyr Tyr Met Asp Asp Ser Gly Ala Met Val
    290                 295                 300

Thr Gly Trp Val Lys Tyr Lys Asn Asn Trp Tyr Tyr Met Thr Asn Glu
305                 310                 315                 320

Arg Gly Asn Met Val Ser Asn Glu Phe Ile Lys Ser Gly Lys Gly Trp
                325                 330                 335

Tyr Phe Met Asn Thr Asn Gly Glu Leu Ala Asp Asn Pro Ser Phe Thr
            340                 345                 350

Lys Glu Pro Asp Gly Leu Ile Thr Val Ala
        355                 360

<210> SEQ ID NO 67
<211> LENGTH: 356
<212> TYPE: PRT
<213> ORGANISM: Unknown
<220> FEATURE:
<223> OTHER INFORMATION: Ranalexin-Cpl1

<400> SEQUENCE: 67

Phe Leu Gly Gly Leu Ile Val Pro Ala Met Ile Cys Ala Val Thr Lys
1               5                   10                  15

Lys Cys Val Lys Lys Asn Asp Leu Phe Val Asp Val Ser Ser His Asn
            20                  25                  30

Gly Tyr Asp Ile Thr Gly Ile Leu Glu Gln Met Gly Thr Thr Asn Thr
        35                  40                  45

Ile Ile Lys Ile Ser Glu Ser Thr Thr Tyr Leu Asn Pro Cys Leu Ser
    50                  55                  60

Ala Gln Val Glu Gln Ser Asn Pro Ile Gly Phe Tyr His Phe Ala Arg
65                  70                  75                  80

Phe Gly Gly Asp Val Ala Glu Ala Glu Arg Glu Ala Gln Phe Phe Leu
                85                  90                  95

Asp Asn Val Pro Met Gln Val Lys Tyr Leu Val Leu Asp Tyr Glu Asp
            100                 105                 110

Asp Pro Ser Gly Asp Ala Gln Ala Asn Thr Asn Ala Cys Leu Arg Phe
        115                 120                 125

Met Gln Met Ile Ala Asp Ala Gly Tyr Lys Pro Ile Tyr Tyr Ser Tyr
    130                 135                 140

Lys Pro Phe Thr His Asp Asn Val Asp Tyr Gln Gln Ile Leu Ala Gln
145                 150                 155                 160

Phe Pro Asn Ser Leu Trp Ile Ala Gly Tyr Gly Leu Asn Asp Gly Thr
                165                 170                 175

Ala Asn Phe Glu Tyr Phe Pro Ser Met Asp Gly Ile Arg Trp Trp Gln
            180                 185                 190

Tyr Ser Ser Asn Pro Phe Asp Lys Asn Ile Val Leu Leu Asp Asp Glu
        195                 200                 205

Glu Asp Asp Lys Pro Lys Thr Ala Gly Thr Trp Lys Gln Asp Ser Lys
    210                 215                 220

Gly Trp Trp Phe Arg Arg Asn Asn Gly Ser Phe Pro Tyr Asn Lys Trp
225                 230                 235                 240

Glu Lys Ile Gly Gly Val Trp Tyr Tyr Phe Asp Ser Lys Gly Tyr Cys
                245                 250                 255

Leu Thr Ser Glu Trp Leu Lys Asp Asn Glu Lys Trp Tyr Tyr Leu Lys
            260                 265                 270

Asp Asn Gly Ala Met Ala Thr Gly Trp Val Leu Val Gly Ser Glu Trp
        275                 280                 285

Tyr Tyr Met Asp Asp Ser Gly Ala Met Val Thr Gly Trp Val Lys Tyr
    290                 295                 300

Lys Asn Asn Trp Tyr Tyr Met Thr Asn Glu Arg Gly Asn Met Val Ser
305                 310                 315                 320

Asn Glu Phe Ile Lys Ser Gly Lys Gly Trp Tyr Phe Met Asn Thr Asn
                325                 330                 335

Gly Glu Leu Ala Asp Asn Pro Ser Phe Thr Lys Glu Pro Asp Gly Leu
            340                 345                 350

Ile Thr Val Ala
        355

<210> SEQ ID NO 68
<211> LENGTH: 365
<212> TYPE: PRT
<213> ORGANISM: Unknown
<220> FEATURE:
<223> OTHER INFORMATION: WLBU2-Variant-Cpl1

<400> SEQUENCE: 68

```
Lys Arg Trp Val Lys Arg Val Lys Arg Val Lys Arg Trp Val Lys Arg
1               5                   10                  15

Val Val Arg Val Val Lys Arg Trp Val Lys Arg Val Lys Lys Asn Asp
                20                  25                  30

Leu Phe Val Asp Val Ser Ser His Asn Gly Tyr Asp Ile Thr Gly Ile
            35                  40                  45

Leu Glu Gln Met Gly Thr Thr Asn Thr Ile Ile Lys Ile Ser Glu Ser
        50                  55                  60

Thr Thr Tyr Leu Asn Pro Cys Leu Ser Ala Gln Val Glu Gln Ser Asn
65                  70                  75                  80

Pro Ile Gly Phe Tyr His Phe Ala Arg Phe Gly Gly Asp Val Ala Glu
                85                  90                  95

Ala Glu Arg Glu Ala Gln Phe Phe Leu Asp Asn Val Pro Met Gln Val
            100                 105                 110

Lys Tyr Leu Val Leu Asp Tyr Glu Asp Asp Pro Ser Gly Asp Ala Gln
        115                 120                 125

Ala Asn Thr Asn Ala Cys Leu Arg Phe Met Gln Met Ile Ala Asp Ala
130                 135                 140

Gly Tyr Lys Pro Ile Tyr Tyr Ser Tyr Lys Pro Phe Thr His Asp Asn
145                 150                 155                 160

Val Asp Tyr Gln Gln Ile Leu Ala Gln Phe Pro Asn Ser Leu Trp Ile
                165                 170                 175

Ala Gly Tyr Gly Leu Asn Asp Gly Thr Ala Asn Phe Glu Tyr Phe Pro
            180                 185                 190

Ser Met Asp Gly Ile Arg Trp Trp Gln Tyr Ser Ser Asn Pro Phe Asp
        195                 200                 205

Lys Asn Ile Val Leu Leu Asp Asp Glu Asp Lys Pro Lys Thr
210                 215                 220

Ala Gly Thr Trp Lys Gln Asp Ser Lys Gly Trp Trp Phe Arg Arg Asn
225                 230                 235                 240

Asn Gly Ser Phe Pro Tyr Asn Lys Trp Glu Lys Ile Gly Gly Val Trp
                245                 250                 255

Tyr Tyr Phe Asp Ser Lys Gly Tyr Cys Leu Thr Ser Glu Trp Leu Lys
            260                 265                 270

Asp Asn Glu Lys Trp Tyr Tyr Leu Lys Asp Asn Gly Ala Met Ala Thr
        275                 280                 285

Gly Trp Val Leu Val Gly Ser Glu Trp Tyr Tyr Met Asp Asp Ser Gly
    290                 295                 300

Ala Met Val Thr Gly Trp Val Lys Tyr Lys Asn Asn Trp Tyr Tyr Met
305                 310                 315                 320

Thr Asn Glu Arg Gly Asn Met Val Ser Asn Glu Phe Ile Lys Ser Gly
                325                 330                 335

Lys Gly Trp Tyr Phe Met Asn Thr Asn Gly Glu Leu Ala Asp Asn Pro
            340                 345                 350

Ser Phe Thr Lys Glu Pro Asp Gly Leu Ile Thr Val Ala
        355                 360                 365
```

<210> SEQ ID NO 69
<211> LENGTH: 372
<212> TYPE: PRT
<213> ORGANISM: Unknown
<220> FEATURE:
<223> OTHER INFORMATION: Sushi1-Cpl1

<400> SEQUENCE: 69

```
Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser Val Lys Lys Asn Asp Leu Phe Val Asp Val Ser His Asn
        35                  40                  45

Gly Tyr Asp Ile Thr Gly Ile Leu Glu Gln Met Gly Thr Thr Asn Thr
    50                  55                  60

Ile Ile Lys Ile Ser Glu Ser Thr Thr Tyr Leu Asn Pro Cys Leu Ser
65                  70                  75                  80

Ala Gln Val Glu Gln Ser Asn Pro Ile Gly Phe Tyr His Phe Ala Arg
                85                  90                  95

Phe Gly Gly Asp Val Ala Glu Ala Glu Arg Glu Ala Gln Phe Phe Leu
            100                 105                 110

Asp Asn Val Pro Met Gln Val Lys Tyr Leu Val Leu Asp Tyr Glu Asp
        115                 120                 125

Asp Pro Ser Gly Asp Ala Gln Ala Asn Thr Asn Ala Cys Leu Arg Phe
    130                 135                 140

Met Gln Met Ile Ala Asp Ala Gly Tyr Lys Pro Ile Tyr Tyr Ser Tyr
145                 150                 155                 160

Lys Pro Phe Thr His Asp Asn Val Asp Tyr Gln Gln Ile Leu Ala Gln
                165                 170                 175

Phe Pro Asn Ser Leu Trp Ile Ala Gly Tyr Gly Leu Asn Asp Gly Thr
            180                 185                 190

Ala Asn Phe Glu Tyr Phe Pro Ser Met Asp Gly Ile Arg Trp Trp Gln
        195                 200                 205

Tyr Ser Ser Asn Pro Phe Asp Lys Asn Ile Val Leu Leu Asp Asp Glu
    210                 215                 220

Glu Asp Asp Lys Pro Lys Thr Ala Gly Thr Trp Lys Gln Asp Ser Lys
225                 230                 235                 240

Gly Trp Trp Phe Arg Arg Asn Asn Gly Ser Phe Pro Tyr Asn Lys Trp
                245                 250                 255

Glu Lys Ile Gly Gly Val Trp Tyr Tyr Phe Asp Ser Lys Gly Tyr Cys
            260                 265                 270

Leu Thr Ser Glu Trp Leu Lys Asp Asn Glu Lys Trp Tyr Tyr Leu Lys
        275                 280                 285

Asp Asn Gly Ala Met Ala Thr Gly Trp Val Leu Val Gly Ser Glu Trp
    290                 295                 300

Tyr Tyr Met Asp Asp Ser Gly Ala Met Val Thr Gly Trp Val Lys Tyr
305                 310                 315                 320

Lys Asn Asn Trp Tyr Tyr Met Thr Asn Glu Arg Gly Asn Met Val Ser
                325                 330                 335

Asn Glu Phe Ile Lys Ser Gly Lys Gly Trp Tyr Phe Met Asn Thr Asn
            340                 345                 350

Gly Glu Leu Ala Asp Asn Pro Ser Phe Thr Lys Glu Pro Asp Gly Leu
        355                 360                 365
```

Ile Thr Val Ala
    370

<210> SEQ ID NO 70
<211> LENGTH: 364
<212> TYPE: PRT
<213> ORGANISM: Unknown
<220> FEATURE:
<223> OTHER INFORMATION: Melttin-Cpl1

<400> SEQUENCE: 70

Gly Ile Gly Ala Val Leu Lys Val Leu Thr Thr Gly Leu Pro Ala Leu
1               5                   10                  15

Ile Ser Trp Ile Lys Arg Lys Arg Gln Gln Val Lys Lys Asn Asp Leu
            20                  25                  30

Phe Val Asp Val Ser Ser His Asn Gly Tyr Asp Ile Thr Gly Ile Leu
        35                  40                  45

Glu Gln Met Gly Thr Thr Asn Thr Ile Ile Lys Ile Ser Glu Ser Thr
    50                  55                  60

Thr Tyr Leu Asn Pro Cys Leu Ser Ala Gln Val Glu Gln Ser Asn Pro
65                  70                  75                  80

Ile Gly Phe Tyr His Phe Ala Arg Phe Gly Gly Asp Val Ala Glu Ala
                85                  90                  95

Glu Arg Glu Ala Gln Phe Phe Leu Asp Asn Val Pro Met Gln Val Lys
            100                 105                 110

Tyr Leu Val Leu Asp Tyr Glu Asp Asp Pro Ser Gly Asp Ala Gln Ala
        115                 120                 125

Asn Thr Asn Ala Cys Leu Arg Phe Met Gln Met Ile Ala Asp Ala Gly
    130                 135                 140

Tyr Lys Pro Ile Tyr Tyr Ser Tyr Lys Pro Phe Thr His Asp Asn Val
145                 150                 155                 160

Asp Tyr Gln Gln Ile Leu Ala Gln Phe Pro Asn Ser Leu Trp Ile Ala
                165                 170                 175

Gly Tyr Gly Leu Asn Asp Gly Thr Ala Asn Phe Glu Tyr Phe Pro Ser
            180                 185                 190

Met Asp Gly Ile Arg Trp Trp Gln Tyr Ser Ser Asn Pro Phe Asp Lys
        195                 200                 205

Asn Ile Val Leu Leu Asp Asp Glu Asp Asp Lys Pro Lys Thr Ala
    210                 215                 220

Gly Thr Trp Lys Gln Asp Ser Lys Gly Trp Trp Phe Arg Arg Asn Asn
225                 230                 235                 240

Gly Ser Phe Pro Tyr Asn Lys Trp Glu Lys Ile Gly Gly Val Trp Tyr
                245                 250                 255

Tyr Phe Asp Ser Lys Gly Tyr Cys Leu Thr Ser Glu Trp Leu Lys Asp
            260                 265                 270

Asn Glu Lys Trp Tyr Tyr Leu Lys Asp Asn Gly Ala Met Ala Thr Gly
        275                 280                 285

Trp Val Leu Val Gly Ser Glu Trp Tyr Tyr Met Asp Asp Ser Gly Ala
    290                 295                 300

Met Val Thr Gly Trp Val Lys Tyr Lys Asn Asn Trp Tyr Tyr Met Thr
305                 310                 315                 320

Asn Glu Arg Gly Asn Met Val Ser Asn Glu Phe Ile Lys Ser Gly Lys
                325                 330                 335

Gly Trp Tyr Phe Met Asn Thr Asn Gly Glu Leu Ala Asp Asn Pro Ser
            340                 345                 350

```
Phe Thr Lys Glu Pro Asp Gly Leu Ile Thr Val Ala
        355                 360
```

<210> SEQ ID NO 71
<211> LENGTH: 375
<212> TYPE: PRT
<213> ORGANISM: Unknown
<220> FEATURE:
<223> OTHER INFORMATION: LL-37-Cpl1

<400> SEQUENCE: 71

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Val Lys Lys Asn Asp Leu Phe Val Asp Val Ser
        35                  40                  45

Ser His Asn Gly Tyr Asp Ile Thr Gly Ile Leu Glu Gln Met Gly Thr
    50                  55                  60

Thr Asn Thr Ile Ile Lys Ile Ser Glu Ser Thr Thr Tyr Leu Asn Pro
65                  70                  75                  80

Cys Leu Ser Ala Gln Val Glu Gln Ser Asn Pro Ile Gly Phe Tyr His
                85                  90                  95

Phe Ala Arg Phe Gly Gly Asp Val Ala Glu Ala Glu Arg Glu Ala Gln
            100                 105                 110

Phe Phe Leu Asp Asn Val Pro Met Gln Val Lys Tyr Leu Val Leu Asp
        115                 120                 125

Tyr Glu Asp Asp Pro Ser Gly Asp Ala Gln Ala Asn Thr Asn Ala Cys
    130                 135                 140

Leu Arg Phe Met Gln Met Ile Ala Asp Ala Gly Tyr Lys Pro Ile Tyr
145                 150                 155                 160

Tyr Ser Tyr Lys Pro Phe Thr His Asp Asn Val Asp Tyr Gln Gln Ile
                165                 170                 175

Leu Ala Gln Phe Pro Asn Ser Leu Trp Ile Ala Gly Tyr Gly Leu Asn
            180                 185                 190

Asp Gly Thr Ala Asn Phe Glu Tyr Phe Pro Ser Met Asp Gly Ile Arg
        195                 200                 205

Trp Trp Gln Tyr Ser Ser Asn Pro Phe Asp Lys Asn Ile Val Leu Leu
    210                 215                 220

Asp Asp Glu Glu Asp Lys Pro Lys Thr Ala Gly Thr Trp Lys Gln
225                 230                 235                 240

Asp Ser Lys Gly Trp Trp Phe Arg Arg Asn Asn Gly Ser Phe Pro Tyr
                245                 250                 255

Asn Lys Trp Glu Lys Ile Gly Val Trp Tyr Tyr Phe Asp Ser Lys
            260                 265                 270

Gly Tyr Cys Leu Thr Ser Glu Trp Leu Lys Asp Asn Glu Lys Trp Tyr
        275                 280                 285

Tyr Leu Lys Asp Asn Gly Ala Met Ala Thr Gly Trp Val Leu Val Gly
    290                 295                 300

Ser Glu Trp Tyr Tyr Met Asp Asp Ser Gly Ala Met Val Thr Gly Trp
305                 310                 315                 320

Val Lys Tyr Lys Asn Asn Trp Tyr Tyr Met Thr Asn Glu Arg Gly Asn
                325                 330                 335

Met Val Ser Asn Glu Phe Ile Lys Ser Gly Lys Gly Trp Tyr Phe Met
            340                 345                 350
```

-continued

Asn Thr Asn Gly Glu Leu Ala Asp Asn Pro Ser Phe Thr Lys Glu Pro
            355                 360                 365

Asp Gly Leu Ile Thr Val Ala
    370             375

<210> SEQ ID NO 72
<211> LENGTH: 351
<212> TYPE: PRT
<213> ORGANISM: Unknown
<220> FEATURE:
<223> OTHER INFORMATION: Indolicidin-Cpl1

<400> SEQUENCE: 72

Ile Leu Pro Trp Lys Trp Pro Trp Trp Pro Trp Arg Arg Val Lys Lys
1               5                   10                  15

Asn Asp Leu Phe Val Asp Val Ser Ser His Asn Gly Tyr Asp Ile Thr
                20                  25                  30

Gly Ile Leu Glu Gln Met Gly Thr Thr Asn Thr Ile Ile Lys Ile Ser
            35                  40                  45

Glu Ser Thr Thr Tyr Leu Asn Pro Cys Leu Ser Ala Gln Val Glu Gln
    50                  55                  60

Ser Asn Pro Ile Gly Phe Tyr His Phe Ala Arg Phe Gly Gly Asp Val
65                  70                  75                  80

Ala Glu Ala Glu Arg Glu Ala Gln Phe Phe Leu Asp Asn Val Pro Met
                85                  90                  95

Gln Val Lys Tyr Leu Val Leu Asp Tyr Glu Asp Asp Pro Ser Gly Asp
            100                 105                 110

Ala Gln Ala Asn Thr Asn Ala Cys Leu Arg Phe Met Gln Met Ile Ala
        115                 120                 125

Asp Ala Gly Tyr Lys Pro Ile Tyr Tyr Ser Tyr Lys Pro Phe Thr His
    130                 135                 140

Asp Asn Val Asp Tyr Gln Gln Ile Leu Ala Gln Phe Pro Asn Ser Leu
145                 150                 155                 160

Trp Ile Ala Gly Tyr Gly Leu Asn Asp Gly Thr Ala Asn Phe Glu Tyr
                165                 170                 175

Phe Pro Ser Met Asp Gly Ile Arg Trp Trp Gln Tyr Ser Ser Asn Pro
            180                 185                 190

Phe Asp Lys Asn Ile Val Leu Leu Asp Asp Glu Glu Asp Asp Lys Pro
        195                 200                 205

Lys Thr Ala Gly Thr Trp Lys Gln Asp Ser Lys Gly Trp Trp Phe Arg
    210                 215                 220

Arg Asn Asn Gly Ser Phe Pro Tyr Asn Lys Trp Glu Lys Ile Gly Gly
225                 230                 235                 240

Val Trp Tyr Tyr Phe Asp Ser Lys Gly Tyr Cys Leu Thr Ser Glu Trp
                245                 250                 255

Leu Lys Asp Asn Glu Lys Trp Tyr Tyr Leu Lys Asp Asn Gly Ala Met
            260                 265                 270

Ala Thr Gly Trp Val Leu Val Gly Ser Glu Trp Tyr Tyr Met Asp Asp
        275                 280                 285

Ser Gly Ala Met Val Thr Gly Trp Val Lys Tyr Lys Asn Asn Trp Tyr
    290                 295                 300

Tyr Met Thr Asn Glu Arg Gly Asn Met Val Ser Asn Glu Phe Ile Lys
305                 310                 315                 320

Ser Gly Lys Gly Trp Tyr Phe Met Asn Thr Asn Gly Glu Leu Ala Asp
                325                 330                 335

Asn Pro Ser Phe Thr Lys Glu Pro Asp Gly Leu Ile Thr Val Ala
            340                 345                 350

<210> SEQ ID NO 73
<211> LENGTH: 367
<212> TYPE: PRT
<213> ORGANISM: Unknown
<220> FEATURE:
<223> OTHER INFORMATION: SMAP-29-Cpl1

<400> SEQUENCE: 73

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Val Lys Lys
                20                  25                  30

Asn Asp Leu Phe Val Asp Val Ser Ser His Asn Gly Tyr Asp Ile Thr
            35                  40                  45

Gly Ile Leu Glu Gln Met Gly Thr Thr Asn Thr Ile Ile Lys Ile Ser
50                  55                  60

Glu Ser Thr Thr Tyr Leu Asn Pro Cys Leu Ser Ala Gln Val Glu Gln
65                  70                  75                  80

Ser Asn Pro Ile Gly Phe Tyr His Phe Ala Arg Phe Gly Gly Asp Val
                85                  90                  95

Ala Glu Ala Glu Arg Glu Ala Gln Phe Phe Leu Asp Asn Val Pro Met
            100                 105                 110

Gln Val Lys Tyr Leu Val Leu Asp Tyr Glu Asp Asp Pro Ser Gly Asp
        115                 120                 125

Ala Gln Ala Asn Thr Asn Ala Cys Leu Arg Phe Met Gln Met Ile Ala
    130                 135                 140

Asp Ala Gly Tyr Lys Pro Ile Tyr Tyr Ser Tyr Lys Pro Phe Thr His
145                 150                 155                 160

Asp Asn Val Asp Tyr Gln Gln Ile Leu Ala Gln Phe Pro Asn Ser Leu
                165                 170                 175

Trp Ile Ala Gly Tyr Gly Leu Asn Asp Gly Thr Ala Asn Phe Glu Tyr
            180                 185                 190

Phe Pro Ser Met Asp Gly Ile Arg Trp Trp Gln Tyr Ser Ser Asn Pro
        195                 200                 205

Phe Asp Lys Asn Ile Val Leu Leu Asp Asp Glu Glu Asp Asp Lys Pro
    210                 215                 220

Lys Thr Ala Gly Thr Trp Lys Gln Asp Ser Lys Gly Trp Trp Phe Arg
225                 230                 235                 240

Arg Asn Asn Gly Ser Phe Pro Tyr Asn Lys Trp Glu Lys Ile Gly Gly
                245                 250                 255

Val Trp Tyr Tyr Phe Asp Ser Lys Gly Tyr Cys Leu Thr Ser Glu Trp
            260                 265                 270

Leu Lys Asp Asn Glu Lys Trp Tyr Tyr Leu Lys Asp Asn Gly Ala Met
        275                 280                 285

Ala Thr Gly Trp Val Leu Val Gly Ser Glu Trp Tyr Tyr Met Asp Asp
    290                 295                 300

Ser Gly Ala Met Val Thr Gly Trp Val Lys Tyr Lys Asn Asn Trp Tyr
305                 310                 315                 320

Tyr Met Thr Asn Glu Arg Gly Asn Met Val Ser Asn Glu Phe Ile Lys
                325                 330                 335

Ser Gly Lys Gly Trp Tyr Phe Met Asn Thr Asn Gly Gly Leu Ala Asp
            340                 345                 350

Asn Pro Ser Phe Thr Lys Glu Pro Asp Gly Leu Ile Thr Val Ala
            355                 360                 365

<210> SEQ ID NO 74
<211> LENGTH: 356
<212> TYPE: PRT
<213> ORGANISM: Unknown
<220> FEATURE:
<223> OTHER INFORMATION: Protegrin-Cpl1

<400> SEQUENCE: 74

Arg Gly Gly Arg Leu Cys Tyr Cys Arg Arg Phe Cys Val Cys Val
1               5                   10                  15

Gly Arg Val Lys Lys Asn Asp Leu Phe Val Asp Val Ser Ser His Asn
            20                  25                  30

Gly Tyr Asp Ile Thr Gly Ile Leu Glu Gln Met Gly Thr Thr Asn Thr
            35                  40                  45

Ile Ile Lys Ile Ser Glu Ser Thr Thr Tyr Leu Asn Pro Cys Leu Ser
50                  55                  60

Ala Gln Val Glu Gln Ser Asn Pro Ile Gly Phe Tyr His Phe Ala Arg
65                  70                  75                  80

Phe Gly Gly Asp Val Ala Glu Ala Glu Arg Glu Ala Gln Phe Phe Leu
                85                  90                  95

Asp Asn Val Pro Met Gln Val Lys Tyr Leu Val Leu Asp Tyr Glu Asp
            100                 105                 110

Asp Pro Ser Gly Asp Ala Gln Ala Asn Thr Asn Ala Cys Leu Arg Phe
            115                 120                 125

Met Gln Met Ile Ala Asp Ala Gly Tyr Lys Pro Ile Tyr Tyr Ser Tyr
130                 135                 140

Lys Pro Phe Thr His Asp Asn Val Asp Tyr Gln Gln Ile Leu Ala Gln
145                 150                 155                 160

Phe Pro Asn Ser Leu Trp Ile Ala Gly Tyr Gly Leu Asn Asp Gly Thr
                165                 170                 175

Ala Asn Phe Glu Tyr Phe Pro Ser Met Asp Gly Ile Arg Trp Trp Gln
            180                 185                 190

Tyr Ser Ser Asn Pro Phe Asp Lys Asn Ile Val Leu Leu Asp Asp Glu
            195                 200                 205

Glu Asp Asp Lys Pro Lys Thr Ala Gly Thr Trp Lys Gln Asp Ser Lys
210                 215                 220

Gly Trp Trp Phe Arg Arg Asn Asn Gly Ser Phe Pro Tyr Asn Lys Trp
225                 230                 235                 240

Glu Lys Ile Gly Gly Val Trp Tyr Tyr Phe Asp Ser Lys Gly Tyr Cys
                245                 250                 255

Leu Thr Ser Glu Trp Leu Lys Asp Asn Glu Lys Trp Tyr Tyr Leu Lys
            260                 265                 270

Asp Asn Gly Ala Met Ala Thr Gly Trp Val Leu Val Gly Ser Glu Trp
275                 280                 285

Tyr Tyr Met Asp Asp Ser Gly Ala Met Val Thr Gly Trp Val Lys Tyr
                290                 295                 300

Lys Asn Asn Trp Tyr Tyr Met Thr Asn Glu Arg Gly Asn Met Val Ser
305                 310                 315                 320

Asn Glu Phe Ile Lys Ser Gly Lys Gly Trp Tyr Phe Met Asn Thr Asn
                325                 330                 335

Gly Glu Leu Ala Asp Asn Pro Ser Phe Thr Lys Glu Pro Asp Gly Leu
            340                 345                 350

Ile Thr Val Ala
        355

<210> SEQ ID NO 75
<211> LENGTH: 369
<212> TYPE: PRT
<213> ORGANISM: Unknown
<220> FEATURE:
<223> OTHER INFORMATION: Cecropin P1-Cpl1

<400> SEQUENCE: 75

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg Val
            20                  25                  30

Lys Lys Asn Asp Leu Phe Val Asp Val Ser Ser His Asn Gly Tyr Asp
        35                  40                  45

Ile Thr Gly Ile Leu Glu Gln Met Gly Thr Thr Asn Thr Ile Ile Lys
    50                  55                  60

Ile Ser Glu Ser Thr Thr Tyr Leu Asn Pro Cys Leu Ser Ala Gln Val
65                  70                  75                  80

Glu Gln Ser Asn Pro Ile Gly Phe Tyr His Phe Ala Arg Phe Gly Gly
                85                  90                  95

Asp Val Ala Glu Ala Glu Arg Glu Ala Gln Phe Phe Leu Asp Asn Val
            100                 105                 110

Pro Met Gln Val Lys Tyr Leu Val Leu Asp Tyr Glu Asp Asp Pro Ser
        115                 120                 125

Gly Asp Ala Gln Ala Asn Thr Asn Ala Cys Leu Arg Phe Met Gln Met
    130                 135                 140

Ile Ala Asp Ala Gly Tyr Lys Pro Ile Tyr Tyr Ser Tyr Lys Pro Phe
145                 150                 155                 160

Thr His Asp Asn Val Asp Tyr Gln Gln Ile Leu Ala Gln Phe Pro Asn
                165                 170                 175

Ser Leu Trp Ile Ala Gly Tyr Gly Leu Asn Asp Gly Thr Ala Asn Phe
            180                 185                 190

Glu Tyr Phe Pro Ser Met Asp Gly Ile Arg Trp Trp Gln Tyr Ser Ser
        195                 200                 205

Asn Pro Phe Asp Lys Asn Ile Val Leu Leu Asp Asp Glu Glu Asp Asp
    210                 215                 220

Lys Pro Lys Thr Ala Gly Thr Trp Lys Gln Asp Ser Lys Gly Trp Trp
225                 230                 235                 240

Phe Arg Arg Asn Asn Gly Ser Phe Pro Tyr Asn Lys Trp Glu Lys Ile
                245                 250                 255

Gly Gly Val Trp Tyr Tyr Phe Asp Ser Lys Gly Tyr Cys Leu Thr Ser
            260                 265                 270

Glu Trp Leu Lys Asp Asn Glu Lys Trp Tyr Tyr Leu Lys Asp Asn Gly
        275                 280                 285

Ala Met Ala Thr Gly Trp Val Leu Val Gly Ser Glu Trp Tyr Tyr Met
    290                 295                 300

Asp Asp Ser Gly Ala Met Val Thr Gly Trp Val Lys Tyr Lys Asn Asn
305                 310                 315                 320

Trp Tyr Tyr Met Thr Asn Glu Arg Gly Asn Met Val Ser Asn Glu Phe
                325                 330                 335

Ile Lys Ser Gly Lys Gly Trp Tyr Phe Met Asn Thr Asn Gly Glu Leu
            340                 345                 350

```
Ala Asp Asn Pro Ser Phe Thr Lys Glu Pro Asp Gly Leu Ile Thr Val
        355                 360                 365
Ala
```

<210> SEQ ID NO 76
<211> LENGTH: 361
<212> TYPE: PRT
<213> ORGANISM: Unknown
<220> FEATURE:
<223> OTHER INFORMATION: Magainin-Cpl1

<400> SEQUENCE: 76

```
Gly Ile Gly Lys Phe Leu His Ser Ala Lys Lys Phe Gly Lys Ala Phe
1               5                   10                  15

Val Gly Glu Ile Met Asn Ser Val Lys Lys Asn Asp Leu Phe Val Asp
            20                  25                  30

Val Ser Ser His Asn Gly Tyr Asp Ile Thr Gly Ile Leu Glu Gln Met
        35                  40                  45

Gly Thr Thr Asn Thr Ile Ile Lys Ile Ser Glu Ser Thr Thr Tyr Leu
    50                  55                  60

Asn Pro Cys Leu Ser Ala Gln Val Glu Gln Ser Asn Pro Ile Gly Phe
65                  70                  75                  80

Tyr His Phe Ala Arg Phe Gly Gly Asp Val Ala Glu Ala Glu Arg Glu
                85                  90                  95

Ala Gln Phe Phe Leu Asp Asn Val Pro Met Gln Val Lys Tyr Leu Val
            100                 105                 110

Leu Asp Tyr Glu Asp Asp Pro Ser Gly Asp Ala Gln Ala Asn Thr Asn
        115                 120                 125

Ala Cys Leu Arg Phe Met Gln Met Ile Ala Asp Ala Gly Tyr Lys Pro
    130                 135                 140

Ile Tyr Tyr Ser Tyr Lys Pro Phe Thr His Asp Asn Val Asp Tyr Gln
145                 150                 155                 160

Gln Ile Leu Ala Gln Phe Pro Asn Ser Leu Trp Ile Ala Gly Tyr Gly
                165                 170                 175

Leu Asn Asp Gly Thr Ala Asn Phe Glu Tyr Phe Pro Ser Met Asp Gly
            180                 185                 190

Ile Arg Trp Trp Gln Tyr Ser Ser Asn Pro Phe Asp Lys Asn Ile Val
        195                 200                 205

Leu Leu Asp Asp Glu Glu Asp Asp Lys Pro Lys Thr Ala Gly Thr Trp
    210                 215                 220

Lys Gln Asp Ser Lys Gly Trp Trp Phe Arg Arg Asn Asn Gly Ser Phe
225                 230                 235                 240

Pro Tyr Asn Lys Trp Glu Lys Ile Gly Gly Val Trp Tyr Tyr Phe Asp
                245                 250                 255

Ser Lys Gly Tyr Cys Leu Thr Ser Glu Trp Leu Lys Asp Asn Glu Lys
            260                 265                 270

Trp Tyr Tyr Leu Lys Asp Asn Gly Ala Met Ala Thr Gly Trp Val Leu
        275                 280                 285

Val Gly Ser Glu Trp Tyr Tyr Met Asp Asp Ser Gly Ala Met Val Thr
    290                 295                 300

Gly Trp Val Lys Tyr Lys Asn Asn Trp Tyr Tyr Met Thr Asn Glu Arg
305                 310                 315                 320

Gly Asn Met Val Ser Asn Glu Phe Ile Lys Ser Gly Lys Gly Trp Tyr
                325                 330                 335

Phe Met Asn Thr Asn Gly Glu Leu Ala Asp Asn Pro Ser Phe Thr Lys
```

```
                340              345              350
Glu Pro Asp Gly Leu Ile Thr Val Ala
            355              360

<210> SEQ ID NO 77
<211> LENGTH: 363
<212> TYPE: PRT
<213> ORGANISM: Unknown
<220> FEATURE:
<223> OTHER INFORMATION: Pleurocidin-Cpl1

<400> SEQUENCE: 77

Gly Trp Gly Ser Phe Phe Lys Lys Ala Ala His Val Gly Lys His Val
1               5                   10                  15

Gly Lys Ala Ala Leu Thr His Tyr Leu Val Lys Lys Asn Asp Leu Phe
            20                  25                  30

Val Asp Val Ser Ser His Asn Gly Tyr Asp Ile Thr Gly Ile Leu Glu
        35                  40                  45

Gln Met Gly Thr Thr Asn Thr Ile Ile Lys Ile Ser Glu Ser Thr Thr
    50                  55                  60

Tyr Leu Asn Pro Cys Leu Ser Ala Gln Val Glu Gln Ser Asn Pro Ile
65                  70                  75                  80

Gly Phe Tyr His Phe Ala Arg Phe Gly Gly Asp Val Ala Glu Ala Glu
                85                  90                  95

Arg Glu Ala Gln Phe Phe Leu Asp Asn Val Pro Met Gln Val Lys Tyr
            100                 105                 110

Leu Val Leu Asp Tyr Glu Asp Asp Pro Ser Gly Asp Ala Gln Ala Asn
        115                 120                 125

Thr Asn Ala Cys Leu Arg Phe Met Gln Met Ile Ala Asp Ala Gly Tyr
    130                 135                 140

Lys Pro Ile Tyr Tyr Ser Tyr Lys Pro Phe Thr His Asp Asn Val Asp
145                 150                 155                 160

Tyr Gln Gln Ile Leu Ala Gln Phe Pro Asn Ser Leu Trp Ile Ala Gly
                165                 170                 175

Tyr Gly Leu Asn Asp Gly Thr Ala Asn Phe Glu Tyr Phe Pro Ser Met
            180                 185                 190

Asp Gly Ile Arg Trp Trp Gln Tyr Ser Ser Asn Pro Phe Asp Lys Asn
        195                 200                 205

Ile Val Leu Leu Asp Asp Glu Glu Asp Asp Lys Pro Lys Thr Ala Gly
    210                 215                 220

Thr Trp Lys Gln Asp Ser Lys Gly Trp Phe Arg Arg Asn Asn Gly
225                 230                 235                 240

Ser Phe Pro Tyr Asn Lys Trp Glu Lys Ile Gly Gly Val Trp Tyr Tyr
                245                 250                 255

Phe Asp Ser Lys Gly Tyr Cys Leu Thr Ser Glu Trp Leu Lys Asp Asn
            260                 265                 270

Glu Lys Trp Tyr Tyr Leu Lys Asp Asn Gly Ala Met Ala Thr Gly Trp
        275                 280                 285

Val Leu Val Gly Ser Glu Trp Tyr Tyr Met Asp Asp Ser Gly Ala Met
    290                 295                 300

Val Thr Gly Trp Val Lys Tyr Lys Asn Asn Trp Tyr Tyr Met Thr Asn
305                 310                 315                 320

Glu Arg Gly Asn Met Val Ser Asn Glu Phe Ile Lys Ser Gly Lys Gly
                325                 330                 335

Trp Tyr Phe Met Asn Thr Asn Gly Glu Leu Ala Asp Asn Pro Ser Phe
```

```
                340              345              350
Thr Lys Glu Pro Asp Gly Leu Ile Thr Val Ala
            355              360

<210> SEQ ID NO 78
<211> LENGTH: 374
<212> TYPE: PRT
<213> ORGANISM: Unknown
<220> FEATURE:
<223> OTHER INFORMATION: Cecropin A (A.aegypti)-Cpl1

<400> SEQUENCE: 78

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys Val Lys Lys Asn Asp Leu Phe Val Asp Val Ser Ser
        35                  40                  45

His Asn Gly Tyr Asp Ile Thr Gly Ile Leu Glu Gln Met Gly Thr Thr
    50                  55                  60

Asn Thr Ile Ile Lys Ile Ser Glu Ser Thr Thr Tyr Leu Asn Pro Cys
65                  70                  75                  80

Leu Ser Ala Gln Val Glu Gln Ser Asn Pro Ile Gly Phe Tyr His Phe
                85                  90                  95

Ala Arg Phe Gly Gly Asp Val Ala Glu Ala Arg Glu Ala Gln Phe
            100                 105                 110

Phe Leu Asp Asn Val Pro Met Gln Val Lys Tyr Leu Val Leu Asp Tyr
        115                 120                 125

Glu Asp Asp Pro Ser Gly Asp Ala Gln Ala Asn Thr Asn Ala Cys Leu
    130                 135                 140

Arg Phe Met Gln Met Ile Ala Asp Ala Gly Tyr Lys Pro Ile Tyr Tyr
145                 150                 155                 160

Ser Tyr Lys Pro Phe Thr His Asp Asn Val Asp Tyr Gln Gln Ile Leu
                165                 170                 175

Ala Gln Phe Pro Asn Ser Leu Trp Ile Ala Gly Tyr Gly Leu Asn Asp
            180                 185                 190

Gly Thr Ala Asn Phe Glu Tyr Phe Pro Ser Met Asp Gly Ile Arg Trp
        195                 200                 205

Trp Gln Tyr Ser Ser Asn Pro Phe Asp Lys Asn Ile Val Leu Leu Asp
    210                 215                 220

Asp Glu Glu Asp Asp Lys Pro Lys Thr Ala Gly Thr Trp Lys Gln Asp
225                 230                 235                 240

Ser Lys Gly Trp Trp Phe Arg Arg Asn Asn Gly Ser Phe Pro Tyr Asn
                245                 250                 255

Lys Trp Glu Lys Ile Gly Gly Val Trp Tyr Tyr Phe Asp Ser Lys Gly
            260                 265                 270

Tyr Cys Leu Thr Ser Glu Trp Leu Lys Asp Asn Glu Lys Trp Tyr Tyr
        275                 280                 285

Leu Lys Asp Asn Gly Ala Met Ala Thr Gly Trp Val Leu Val Gly Ser
    290                 295                 300

Glu Trp Tyr Tyr Met Asp Asp Ser Gly Ala Met Val Thr Gly Trp Val
305                 310                 315                 320

Lys Tyr Lys Asn Asn Trp Tyr Tyr Met Thr Asn Glu Arg Gly Asn Met
                325                 330                 335

Val Ser Asn Glu Phe Ile Lys Ser Gly Lys Gly Trp Tyr Phe Met Asn
```

-continued

```
                340                 345                 350
Thr Asn Gly Glu Leu Ala Asp Asn Pro Ser Phe Thr Lys Glu Pro Asp
            355                 360                 365
Gly Leu Ile Thr Val Ala
        370

<210> SEQ ID NO 79
<211> LENGTH: 378
<212> TYPE: PRT
<213> ORGANISM: Unknown
<220> FEATURE:
<223> OTHER INFORMATION: Cecropin A (D.melanogaster)-Cp11

<400> SEQUENCE: 79

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly Val Lys Lys Asn Asp Leu Phe Val
        35                  40                  45

Asp Val Ser Ser His Asn Gly Tyr Asp Ile Thr Gly Ile Leu Glu Gln
    50                  55                  60

Met Gly Thr Thr Asn Thr Ile Ile Lys Ile Ser Glu Ser Thr Thr Tyr
65                  70                  75                  80

Leu Asn Pro Cys Leu Ser Ala Gln Val Glu Gln Ser Asn Pro Ile Gly
                85                  90                  95

Phe Tyr His Phe Ala Arg Phe Gly Gly Asp Val Ala Glu Ala Glu Arg
            100                 105                 110

Glu Ala Gln Phe Phe Leu Asp Asn Val Pro Met Gln Val Lys Tyr Leu
        115                 120                 125

Val Leu Asp Tyr Glu Asp Asp Pro Ser Gly Asp Ala Gln Ala Asn Thr
    130                 135                 140

Asn Ala Cys Leu Arg Phe Met Gln Met Ile Ala Asp Ala Gly Tyr Lys
145                 150                 155                 160

Pro Ile Tyr Tyr Ser Tyr Lys Pro Phe Thr His Asp Asn Val Asp Tyr
                165                 170                 175

Gln Gln Ile Leu Ala Gln Phe Pro Asn Ser Leu Trp Ile Ala Gly Tyr
            180                 185                 190

Gly Leu Asn Asp Gly Thr Ala Asn Phe Glu Tyr Phe Pro Ser Met Asp
        195                 200                 205

Gly Ile Arg Trp Trp Gln Tyr Ser Ser Asn Pro Phe Asp Lys Asn Ile
    210                 215                 220

Val Leu Leu Asp Asp Glu Glu Asp Asp Lys Pro Lys Thr Ala Gly Thr
225                 230                 235                 240

Trp Lys Gln Asp Ser Lys Gly Trp Trp Phe Arg Arg Asn Asn Gly Ser
                245                 250                 255

Phe Pro Tyr Asn Lys Trp Glu Lys Ile Gly Gly Val Trp Tyr Tyr Phe
            260                 265                 270

Asp Ser Lys Gly Tyr Cys Leu Thr Ser Glu Trp Leu Lys Asp Asn Glu
        275                 280                 285

Lys Trp Tyr Tyr Leu Lys Asp Asn Gly Ala Met Ala Thr Gly Trp Val
    290                 295                 300

Leu Val Gly Ser Glu Trp Tyr Tyr Met Asp Asp Ser Gly Ala Met Val
305                 310                 315                 320

Thr Gly Trp Val Lys Tyr Lys Asn Asn Trp Tyr Tyr Met Thr Asn Glu
```

```
                    325                 330                 335
Arg Gly Asn Met Val Ser Asn Glu Phe Ile Lys Ser Gly Lys Gly Trp
                340                 345                 350

Tyr Phe Met Asn Thr Asn Gly Glu Leu Ala Asp Asn Pro Ser Phe Thr
                355                 360                 365

Lys Glu Pro Asp Gly Leu Ile Thr Val Ala
            370                 375

<210> SEQ ID NO 80
<211> LENGTH: 359
<212> TYPE: PRT
<213> ORGANISM: Unknown
<220> FEATURE:
<223> OTHER INFORMATION: BuforinII-Cpl1

<400> SEQUENCE: 80

Thr Arg Ser Ser Arg Ala Gly Leu Gln Phe Pro Val Gly Arg Val His
1               5                   10                  15

Arg Leu Leu Arg Lys Val Lys Lys Asn Asp Leu Phe Val Asp Val Ser
                20                  25                  30

Ser His Asn Gly Tyr Asp Ile Thr Gly Ile Leu Glu Gln Met Gly Thr
            35                  40                  45

Thr Asn Thr Ile Ile Lys Ile Ser Glu Ser Thr Thr Tyr Leu Asn Pro
    50                  55                  60

Cys Leu Ser Ala Gln Val Glu Gln Ser Asn Pro Ile Gly Phe Tyr His
65                  70                  75                  80

Phe Ala Arg Phe Gly Gly Asp Val Ala Glu Ala Glu Arg Glu Ala Gln
                85                  90                  95

Phe Phe Leu Asp Asn Val Pro Met Gln Val Lys Tyr Leu Val Leu Asp
                100                 105                 110

Tyr Glu Asp Asp Pro Ser Gly Asp Ala Gln Ala Asn Thr Asn Ala Cys
            115                 120                 125

Leu Arg Phe Met Gln Met Ile Ala Asp Ala Gly Tyr Lys Pro Ile Tyr
    130                 135                 140

Tyr Ser Tyr Lys Pro Phe Thr His Asp Asn Val Asp Tyr Gln Gln Ile
145                 150                 155                 160

Leu Ala Gln Phe Pro Asn Ser Leu Trp Ile Ala Gly Tyr Gly Leu Asn
                165                 170                 175

Asp Gly Thr Ala Asn Phe Glu Tyr Phe Pro Ser Met Asp Gly Ile Arg
            180                 185                 190

Trp Trp Gln Tyr Ser Ser Asn Pro Phe Asp Lys Asn Ile Val Leu Leu
    195                 200                 205

Asp Asp Glu Glu Asp Lys Pro Lys Thr Ala Gly Thr Trp Lys Gln
210                 215                 220

Asp Ser Lys Gly Trp Trp Phe Arg Arg Asn Asn Gly Ser Phe Pro Tyr
225                 230                 235                 240

Asn Lys Trp Glu Lys Ile Gly Gly Val Trp Tyr Tyr Phe Asp Ser Lys
                245                 250                 255

Gly Tyr Cys Leu Thr Ser Glu Trp Leu Lys Asp Asn Glu Lys Trp Tyr
            260                 265                 270

Tyr Leu Lys Asp Asn Gly Ala Met Ala Thr Gly Trp Val Leu Val Gly
    275                 280                 285

Ser Glu Trp Tyr Tyr Met Asp Asp Ser Gly Ala Met Val Thr Gly Trp
    290                 295                 300

Val Lys Tyr Lys Asn Asn Trp Tyr Tyr Met Thr Asn Glu Arg Gly Asn
```

```
               305                 310                 315                 320
Met Val Ser Asn Glu Phe Ile Lys Ser Gly Lys Gly Trp Tyr Phe Met
                    325                 330                 335

Asn Thr Asn Gly Glu Leu Ala Asp Asn Pro Ser Phe Thr Lys Glu Pro
                    340                 345                 350

Asp Gly Leu Ile Thr Val Ala
            355

<210> SEQ ID NO 81
<211> LENGTH: 377
<212> TYPE: PRT
<213> ORGANISM: Unknown
<220> FEATURE:
<223> OTHER INFORMATION: Sarcotoxin IA-Cp11

<400> SEQUENCE: 81

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Val Lys Lys Asn Asp Leu Phe Val Asp
        35                  40                  45

Val Ser Ser His Asn Gly Tyr Asp Ile Thr Gly Ile Leu Glu Gln Met
    50                  55                  60

Gly Thr Thr Asn Thr Ile Ile Lys Ile Ser Glu Ser Thr Thr Tyr Leu
65                  70                  75                  80

Asn Pro Cys Leu Ser Ala Gln Val Glu Gln Ser Asn Pro Ile Gly Phe
                85                  90                  95

Tyr His Phe Ala Arg Phe Gly Gly Asp Val Ala Glu Ala Glu Arg Glu
            100                 105                 110

Ala Gln Phe Phe Leu Asp Asn Val Pro Met Gln Val Lys Tyr Leu Val
        115                 120                 125

Leu Asp Tyr Glu Asp Asp Pro Ser Gly Asp Ala Gln Ala Asn Thr Asn
    130                 135                 140

Ala Cys Leu Arg Phe Met Gln Met Ile Ala Asp Ala Gly Tyr Lys Pro
145                 150                 155                 160

Ile Tyr Tyr Ser Tyr Lys Pro Phe Thr His Asp Asn Val Asp Tyr Gln
                165                 170                 175

Gln Ile Leu Ala Gln Phe Pro Asn Ser Leu Trp Ile Ala Gly Tyr Gly
            180                 185                 190

Leu Asn Asp Gly Thr Ala Asn Phe Glu Tyr Phe Pro Ser Met Asp Gly
        195                 200                 205

Ile Arg Trp Trp Gln Tyr Ser Ser Asn Pro Phe Asp Lys Asn Ile Val
    210                 215                 220

Leu Leu Asp Asp Glu Glu Asp Asp Lys Pro Lys Thr Ala Gly Thr Trp
225                 230                 235                 240

Lys Gln Asp Ser Lys Gly Trp Trp Phe Arg Arg Asn Asn Gly Ser Phe
                245                 250                 255

Pro Tyr Asn Lys Trp Glu Lys Ile Gly Gly Val Trp Tyr Tyr Phe Asp
            260                 265                 270

Ser Lys Gly Tyr Cys Leu Thr Ser Glu Trp Leu Lys Asp Asn Glu Lys
        275                 280                 285

Trp Tyr Tyr Leu Lys Asp Asn Gly Ala Met Ala Thr Gly Trp Val Leu
    290                 295                 300

Val Gly Ser Glu Trp Tyr Tyr Met Asp Asp Ser Gly Ala Met Val Thr
```

```
            305                 310                 315                 320
Gly Trp Val Lys Tyr Lys Asn Asn Trp Tyr Tyr Met Thr Asn Glu Arg
                    325                 330                 335

Gly Asn Met Val Ser Asn Glu Phe Ile Lys Ser Gly Lys Gly Trp Tyr
                340                 345                 350

Phe Met Asn Thr Asn Gly Glu Leu Ala Asp Asn Pro Ser Phe Thr Lys
            355                 360                 365

Glu Pro Asp Gly Leu Ile Thr Val Ala
        370                 375
```

<210> SEQ ID NO 82
<211> LENGTH: 347
<212> TYPE: PRT
<213> ORGANISM: Unknown
<220> FEATURE:
<223> OTHER INFORMATION: PK-Cpl1

<400> SEQUENCE: 82

```
Lys Arg Lys Lys Arg Lys Lys Arg Lys Val Lys Lys Asn Asp Leu Phe
1               5                   10                  15

Val Asp Val Ser Ser His Asn Gly Tyr Asp Ile Thr Gly Ile Leu Glu
            20                  25                  30

Gln Met Gly Thr Thr Asn Thr Ile Ile Lys Ile Ser Glu Ser Thr Thr
        35                  40                  45

Tyr Leu Asn Pro Cys Leu Ser Ala Gln Val Glu Gln Ser Asn Pro Ile
50                  55                  60

Gly Phe Tyr His Phe Ala Arg Phe Gly Gly Asp Val Ala Glu Ala Glu
65                  70                  75                  80

Arg Glu Ala Gln Phe Phe Leu Asp Asn Val Pro Met Gln Val Lys Tyr
                85                  90                  95

Leu Val Leu Asp Tyr Glu Asp Pro Ser Gly Asp Ala Gln Ala Asn
            100                 105                 110

Thr Asn Ala Cys Leu Arg Phe Met Gln Met Ile Ala Asp Ala Gly Tyr
        115                 120                 125

Lys Pro Ile Tyr Tyr Ser Tyr Lys Pro Phe Thr His Asp Asn Val Asp
130                 135                 140

Tyr Gln Gln Ile Leu Ala Gln Phe Pro Asn Ser Leu Trp Ile Ala Gly
145                 150                 155                 160

Tyr Gly Leu Asn Asp Gly Thr Ala Asn Phe Glu Tyr Phe Pro Ser Met
                165                 170                 175

Asp Gly Ile Arg Trp Trp Gln Tyr Ser Ser Asn Pro Phe Asp Lys Asn
            180                 185                 190

Ile Val Leu Leu Asp Asp Glu Asp Lys Pro Lys Thr Ala Gly
        195                 200                 205

Thr Trp Lys Gln Asp Ser Lys Gly Trp Trp Phe Arg Arg Asn Asn Gly
210                 215                 220

Ser Phe Pro Tyr Asn Lys Trp Glu Lys Ile Gly Gly Val Trp Tyr Tyr
225                 230                 235                 240

Phe Asp Ser Lys Gly Tyr Cys Leu Thr Ser Glu Trp Leu Lys Asp Asn
                245                 250                 255

Glu Lys Trp Tyr Tyr Leu Lys Asp Asn Gly Ala Met Ala Thr Gly Trp
            260                 265                 270

Val Leu Val Gly Ser Glu Trp Tyr Met Asp Asp Ser Gly Ala Met
        275                 280                 285

Val Thr Gly Trp Val Lys Tyr Lys Asn Asn Trp Tyr Tyr Met Thr Asn
```

```
                290                 295                 300
Glu Arg Gly Asn Met Val Ser Asn Glu Phe Ile Lys Ser Gly Lys Gly
305                 310                 315                 320

Trp Tyr Phe Met Asn Thr Asn Gly Glu Leu Ala Asp Asn Pro Ser Phe
                325                 330                 335

Thr Lys Glu Pro Asp Gly Leu Ile Thr Val Ala
            340                 345

<210> SEQ ID NO 83
<211> LENGTH: 345
<212> TYPE: PRT
<213> ORGANISM: Unknown
<220> FEATURE:
<223> OTHER INFORMATION: Synthetic peptide-Ply511

<400> SEQUENCE: 83

Phe Phe Val Ala Pro Val Lys Tyr Thr Val Glu Asn Lys Ile Ile Ala
1               5                   10                  15

Gly Leu Pro Lys Gly Lys Leu Lys Gly Ala Asn Phe Val Ile Ala His
                20                  25                  30

Glu Thr Ala Asn Ser Lys Ser Thr Ile Asp Asn Glu Val Ser Tyr Met
            35                  40                  45

Thr Arg Asn Trp Lys Asn Ala Phe Val Thr His Phe Val Gly Gly Gly
        50                  55                  60

Gly Arg Val Val Gln Val Ala Asn Val Asn Tyr Val Ser Trp Gly Ala
65                  70                  75                  80

Gly Gln Tyr Ala Asn Ser Tyr Ser Tyr Ala Gln Val Glu Leu Cys Arg
                85                  90                  95

Thr Ser Asn Ala Thr Thr Phe Lys Lys Asp Tyr Glu Val Tyr Cys Gln
                100                 105                 110

Leu Leu Val Asp Leu Ala Lys Lys Ala Gly Ile Pro Ile Thr Leu Asp
            115                 120                 125

Ser Gly Ser Lys Thr Ser Asp Lys Gly Ile Lys Ser His Lys Trp Val
        130                 135                 140

Ala Asp Lys Leu Gly Gly Thr Thr His Gln Asp Pro Tyr Ala Tyr Leu
145                 150                 155                 160

Ser Ser Trp Gly Ile Ser Lys Ala Gln Phe Ala Ser Asp Leu Ala Lys
                165                 170                 175

Val Ser Gly Gly Gly Asn Thr Gly Thr Ala Pro Ala Lys Pro Ser Thr
                180                 185                 190

Pro Ala Pro Lys Pro Ser Thr Pro Ser Thr Asn Leu Asp Lys Leu Gly
            195                 200                 205

Leu Val Asp Tyr Met Asn Ala Lys Lys Met Asp Ser Ser Tyr Ser Asn
210                 215                 220

Arg Asp Lys Leu Ala Lys Gln Tyr Gly Ile Ala Asn Tyr Ser Gly Thr
225                 230                 235                 240

Ala Ser Gln Asn Thr Thr Leu Leu Ser Lys Ile Lys Gly Gly Ala Pro
                245                 250                 255

Lys Pro Ser Thr Pro Ala Pro Lys Pro Ser Thr Ser Thr Ala Lys Lys
            260                 265                 270

Ile Tyr Phe Pro Pro Asn Lys Gly Asn Trp Ser Val Tyr Pro Thr Asn
        275                 280                 285

Lys Ala Pro Val Lys Ala Asn Ala Ile Gly Ala Ile Asn Pro Thr Lys
290                 295                 300

Phe Gly Gly Leu Thr Tyr Thr Ile Gln Lys Asp Arg Gly Asn Gly Val
```

```
            305                 310                 315                 320
Tyr Glu Ile Gln Thr Asp Gln Phe Gly Arg Val Gln Val Tyr Gly Ala
                    325                 330                 335
Pro Ser Thr Gly Ala Val Ile Lys Lys
                340                 345

<210> SEQ ID NO 84
<211> LENGTH: 503
<212> TYPE: PRT
<213> ORGANISM: Unknown
<220> FEATURE:
<223> OTHER INFORMATION: PK-LysK (PK N-terminal)

<400> SEQUENCE: 84

Lys Arg Lys Lys Arg Lys Lys Arg Lys Ala Lys Thr Gln Ala Glu Ile
1               5                   10                  15
Asn Lys Arg Leu Asp Ala Tyr Ala Lys Gly Thr Val Asp Ser Pro Tyr
                20                  25                  30
Arg Val Lys Lys Ala Thr Ser Tyr Asp Pro Ser Phe Gly Val Met Glu
            35                  40                  45
Ala Gly Ala Ile Asp Ala Asp Gly Tyr Tyr His Ala Gln Cys Gln Asp
        50                  55                  60
Leu Ile Thr Asp Tyr Val Leu Trp Leu Thr Asp Asn Lys Val Arg Thr
65                  70                  75                  80
Trp Gly Asn Ala Lys Asp Gln Ile Lys Gln Ser Tyr Gly Thr Gly Phe
                85                  90                  95
Lys Ile His Glu Asn Lys Pro Ser Thr Val Pro Lys Lys Gly Trp Ile
            100                 105                 110
Ala Val Phe Thr Ser Gly Ser Tyr Glu Gln Trp Gly His Ile Gly Ile
        115                 120                 125
Val Tyr Asp Gly Gly Asn Thr Ser Thr Phe Thr Ile Leu Glu Gln Asn
130                 135                 140
Trp Asn Gly Tyr Ala Asn Lys Lys Pro Thr Lys Arg Val Asp Asn Tyr
145                 150                 155                 160
Tyr Gly Leu Thr His Phe Ile Glu Ile Pro Val Lys Ala Gly Thr Thr
                165                 170                 175
Val Lys Lys Glu Thr Ala Lys Lys Ser Ala Ser Lys Thr Pro Ala Pro
            180                 185                 190
Lys Lys Lys Ala Thr Leu Lys Val Ser Lys Asn His Ile Asn Tyr Thr
        195                 200                 205
Met Asp Lys Arg Gly Lys Lys Pro Glu Gly Met Val Ile His Asn Asp
    210                 215                 220
Ala Gly Arg Ser Ser Gly Gln Gln Tyr Glu Asn Ser Leu Ala Asn Ala
225                 230                 235                 240
Gly Tyr Ala Arg Tyr Ala Asn Gly Ile Ala His Tyr Tyr Gly Ser Glu
                245                 250                 255
Gly Tyr Val Trp Glu Ala Ile Asp Ala Lys Asn Gln Ile Ala Trp His
            260                 265                 270
Thr Gly Asp Gly Thr Gly Ala Asn Ser Gly Asn Phe Arg Phe Ala Gly
        275                 280                 285
Ile Glu Val Cys Gln Ser Met Ser Ala Ser Asp Ala Gln Phe Leu Lys
    290                 295                 300
Asn Glu Gln Ala Val Phe Gln Phe Thr Ala Glu Lys Phe Lys Glu Trp
305                 310                 315                 320
Gly Leu Thr Pro Asn Arg Lys Thr Val Arg Leu His Met Glu Phe Val
```

```
                    325                 330                 335
Pro Thr Ala Cys Pro His Arg Ser Met Val Leu His Thr Gly Phe Asn
            340                 345                 350

Pro Val Thr Gln Gly Arg Pro Ser Gln Ala Ile Met Asn Lys Leu Lys
            355                 360                 365

Asp Tyr Phe Ile Lys Gln Ile Lys Asn Tyr Met Asp Lys Gly Thr Ser
            370                 375                 380

Ser Ser Thr Val Val Lys Asp Gly Lys Thr Ser Ser Ala Ser Thr Pro
385                 390                 395                 400

Ala Thr Arg Pro Val Thr Gly Ser Trp Lys Lys Asn Gln Tyr Gly Thr
            405                 410                 415

Trp Tyr Lys Pro Glu Asn Ala Thr Phe Val Asn Gly Asn Gln Pro Ile
            420                 425                 430

Val Thr Arg Ile Gly Ser Pro Phe Leu Asn Ala Pro Val Gly Gly Asn
            435                 440                 445

Leu Pro Ala Gly Ala Thr Ile Val Tyr Asp Glu Val Cys Ile Gln Ala
            450                 455                 460

Gly His Ile Trp Ile Gly Tyr Asn Ala Tyr Asn Gly Asn Arg Val Tyr
465                 470                 475                 480

Cys Pro Val Arg Thr Cys Gln Gly Val Pro Pro Asn Gln Ile Pro Gly
            485                 490                 495

Val Ala Trp Gly Val Phe Lys
            500

<210> SEQ ID NO 85
<211> LENGTH: 512
<212> TYPE: PRT
<213> ORGANISM: Unknown
<220> FEATURE:
<223> OTHER INFORMATION: PK2-LysK

<400> SEQUENCE: 85

Lys Arg Lys Lys Arg Lys Lys Arg Lys Lys Arg Lys Lys Arg Lys Lys
1               5                   10                  15

Arg Lys Ala Lys Thr Gln Ala Glu Ile Asn Lys Arg Leu Asp Ala Tyr
            20                  25                  30

Ala Lys Gly Thr Val Asp Ser Pro Tyr Arg Val Lys Lys Ala Thr Ser
            35                  40                  45

Tyr Asp Pro Ser Phe Gly Val Met Glu Ala Gly Ala Ile Asp Ala Asp
            50                  55                  60

Gly Tyr Tyr His Ala Gln Cys Gln Asp Leu Ile Thr Asp Tyr Val Leu
65                  70                  75                  80

Trp Leu Thr Asp Asn Lys Val Arg Thr Trp Gly Asn Ala Lys Asp Gln
            85                  90                  95

Ile Lys Gln Ser Tyr Gly Thr Gly Phe Lys Ile His Glu Asn Lys Pro
            100                 105                 110

Ser Thr Val Pro Lys Lys Gly Trp Ile Ala Val Phe Thr Ser Gly Ser
            115                 120                 125

Tyr Glu Gln Trp Gly His Ile Gly Ile Val Tyr Asp Gly Gly Asn Thr
            130                 135                 140

Ser Thr Phe Thr Ile Leu Glu Gln Asn Trp Asn Gly Tyr Ala Asn Lys
145                 150                 155                 160

Lys Pro Thr Lys Arg Val Asp Asn Tyr Tyr Gly Leu Thr His Phe Ile
            165                 170                 175

Glu Ile Pro Val Lys Ala Gly Thr Thr Val Lys Lys Glu Thr Ala Lys
```

```
                180             185             190
Lys Ser Ala Ser Lys Thr Pro Ala Pro Lys Lys Ala Thr Leu Lys
            195             200             205

Val Ser Lys Asn His Ile Asn Tyr Thr Met Asp Lys Arg Gly Lys Lys
        210             215             220

Pro Glu Gly Met Val Ile His Asn Asp Ala Gly Arg Ser Ser Gly Gln
225             230             235             240

Gln Tyr Glu Asn Ser Leu Ala Asn Ala Gly Tyr Ala Arg Tyr Ala Asn
            245             250             255

Gly Ile Ala His Tyr Tyr Gly Ser Glu Gly Tyr Val Trp Glu Ala Ile
            260             265             270

Asp Ala Lys Asn Gln Ile Ala Trp His Thr Gly Asp Gly Thr Gly Ala
        275             280             285

Asn Ser Gly Asn Phe Arg Phe Ala Gly Ile Glu Val Cys Gln Ser Met
        290             295             300

Ser Ala Ser Asp Ala Gln Phe Leu Lys Asn Glu Gln Ala Val Phe Gln
305             310             315             320

Phe Thr Ala Glu Lys Phe Lys Glu Trp Gly Leu Thr Pro Asn Arg Lys
            325             330             335

Thr Val Arg Leu His Met Glu Phe Val Pro Thr Ala Cys Pro His Arg
            340             345             350

Ser Met Val Leu His Thr Gly Phe Asn Pro Val Thr Gln Gly Arg Pro
            355             360             365

Ser Gln Ala Ile Met Asn Lys Leu Lys Asp Tyr Phe Ile Lys Gln Ile
        370             375             380

Lys Asn Tyr Met Asp Lys Gly Thr Ser Ser Ser Thr Val Val Lys Asp
385             390             395             400

Gly Lys Thr Ser Ser Ala Ser Thr Pro Ala Thr Arg Pro Val Thr Gly
            405             410             415

Ser Trp Lys Lys Asn Gln Tyr Gly Thr Trp Tyr Lys Pro Glu Asn Ala
            420             425             430

Thr Phe Val Asn Gly Asn Gln Pro Ile Val Thr Arg Ile Gly Ser Pro
        435             440             445

Phe Leu Asn Ala Pro Val Gly Gly Asn Leu Pro Ala Gly Ala Thr Ile
        450             455             460

Val Tyr Asp Glu Val Cys Ile Gln Ala Gly His Ile Trp Ile Gly Tyr
465             470             475             480

Asn Ala Tyr Asn Gly Asn Arg Val Tyr Cys Pro Val Arg Thr Cys Gln
            485             490             495

Gly Val Pro Pro Asn Gln Ile Pro Gly Val Ala Trp Gly Val Phe Lys
            500             505             510

<210> SEQ ID NO 86
<211> LENGTH: 259
<212> TYPE: PRT
<213> ORGANISM: Unknown
<220> FEATURE:
<223> OTHER INFORMATION: PK-Lss

<400> SEQUENCE: 86

Lys Arg Lys Lys Arg Lys Lys Arg Lys Ala His Glu His Ser Ala Gln
1               5                   10                  15

Trp Leu Asn Asn Tyr Lys Lys Gly Tyr Gly Tyr Gly Pro Tyr Pro Leu
            20              25                  30

Gly Ile Asn Gly Gly Met His Tyr Gly Val Asp Phe Phe Met Asn Ile
```

```
            35                  40                  45
Gly Thr Pro Val Lys Ala Ile Ser Ser Gly Lys Ile Val Glu Ala Gly
 50                  55                  60

Trp Ser Asn Tyr Gly Gly Asn Gln Ile Gly Leu Ile Glu Asn Asp
 65                  70                  75                  80

Gly Val His Arg Gln Trp Tyr Met His Leu Ser Lys Tyr Asn Val Lys
                 85                  90                  95

Val Gly Asp Tyr Val Lys Ala Gly Gln Ile Ile Gly Trp Ser Gly Ser
                100                 105                 110

Thr Gly Tyr Ser Thr Ala Pro His Leu His Phe Gln Arg Met Val Asn
            115                 120                 125

Ser Phe Ser Asn Ser Thr Ala Gln Asp Pro Met Pro Phe Leu Lys Ser
130                 135                 140

Ala Gly Tyr Gly Lys Ala Gly Gly Thr Val Thr Pro Thr Pro Asn Thr
145                 150                 155                 160

Gly Trp Lys Thr Asn Lys Tyr Gly Thr Leu Tyr Lys Ser Glu Ser Ala
                165                 170                 175

Ser Phe Thr Pro Asn Thr Asp Ile Ile Thr Arg Thr Thr Gly Pro Phe
            180                 185                 190

Arg Ser Met Pro Gln Ser Gly Val Leu Lys Ala Gly Gln Thr Ile His
        195                 200                 205

Tyr Asp Glu Val Met Lys Gln Asp Gly His Val Trp Val Gly Tyr Thr
210                 215                 220

Gly Asn Ser Gly Gln Arg Ile Tyr Leu Pro Val Arg Thr Trp Asn Lys
225                 230                 235                 240

Ser Thr Asn Thr Leu Gly Val Leu Trp Gly Thr Ile Lys Leu Val Pro
                245                 250                 255

Arg Gly Ser

<210> SEQ ID NO 87
<211> LENGTH: 268
<212> TYPE: PRT
<213> ORGANISM: Unknown
<220> FEATURE:
<223> OTHER INFORMATION: PK2-Lss

<400> SEQUENCE: 87

Lys Arg Lys Lys Arg Lys Lys Arg Lys Lys Arg Lys Lys Arg Lys Lys
  1               5                  10                  15

Arg Lys Ala His Glu His Ser Ala Gln Trp Leu Asn Asn Tyr Lys Lys
                 20                  25                  30

Gly Tyr Gly Tyr Gly Pro Tyr Pro Leu Gly Ile Asn Gly Gly Met His
            35                  40                  45

Tyr Gly Val Asp Phe Phe Met Asn Ile Gly Thr Pro Val Lys Ala Ile
 50                  55                  60

Ser Ser Gly Lys Ile Val Glu Ala Gly Trp Ser Asn Tyr Gly Gly
 65                  70                  75                  80

Asn Gln Ile Gly Leu Ile Glu Asn Asp Gly Val His Arg Gln Trp Tyr
                 85                  90                  95

Met His Leu Ser Lys Tyr Asn Val Lys Val Gly Asp Tyr Val Lys Ala
                100                 105                 110

Gly Gln Ile Ile Gly Trp Ser Gly Ser Thr Gly Tyr Ser Thr Ala Pro
            115                 120                 125

His Leu His Phe Gln Arg Met Val Asn Ser Phe Ser Asn Ser Thr Ala
130                 135                 140
```

```
Gln Asp Pro Met Pro Phe Leu Lys Ser Ala Gly Tyr Gly Lys Ala Gly
145                 150                 155                 160

Gly Thr Val Thr Pro Thr Pro Asn Thr Gly Trp Lys Thr Asn Lys Tyr
                165                 170                 175

Gly Thr Leu Tyr Lys Ser Glu Ser Ala Ser Phe Thr Pro Asn Thr Asp
            180                 185                 190

Ile Ile Thr Arg Thr Thr Gly Pro Phe Arg Ser Met Pro Gln Ser Gly
            195                 200                 205

Val Leu Lys Ala Gly Gln Thr Ile His Tyr Asp Glu Val Met Lys Gln
210                 215                 220

Asp Gly His Val Trp Val Gly Tyr Thr Gly Asn Ser Gly Gln Arg Ile
225                 230                 235                 240

Tyr Leu Pro Val Arg Thr Trp Asn Lys Ser Thr Asn Thr Leu Gly Val
                245                 250                 255

Leu Trp Gly Thr Ile Lys Leu Val Pro Arg Gly Ser
            260                 265

<210> SEQ ID NO 88
<211> LENGTH: 303
<212> TYPE: PRT
<213> ORGANISM: Unknown
<220> FEATURE:
<223> OTHER INFORMATION: Walmagh1-PA6gp20

<400> SEQUENCE: 88

Gly Phe Phe Ile Pro Ala Val Ile Leu Pro Ser Ile Ala Phe Leu Ile
1               5                   10                  15

Val Pro Val Arg Tyr Ile Pro Ala Ala His Ser Ala Gly Ser Asn
                20                  25                  30

Asn Pro Val Asn Arg Val Val Ile His Ala Thr Cys Pro Asp Val Gly
            35                  40                  45

Phe Pro Ser Ala Ser Arg Lys Gly Arg Ala Val Ser Thr Ala Asn Tyr
50                  55                  60

Phe Ala Ser Pro Ser Ser Gly Gly Ser Ala His Tyr Val Cys Asp Ile
65                  70                  75                  80

Gly Glu Thr Val Gln Cys Leu Ser Glu Ser Thr Ile Gly Trp His Ala
                85                  90                  95

Pro Pro Asn Pro His Ser Leu Gly Ile Glu Ile Cys Ala Asp Gly Gly
            100                 105                 110

Ser His Ala Ser Phe Arg Val Pro Gly His Ala Tyr Thr Arg Glu Gln
        115                 120                 125

Trp Leu Asp Pro Gln Val Trp Pro Ala Val Glu Arg Ala Ala Val Leu
130                 135                 140

Cys Arg Arg Leu Cys Asp Lys Tyr Asn Val Pro Lys Arg Lys Leu Ser
145                 150                 155                 160

Ala Ala Asp Leu Lys Ala Gly Arg Arg Gly Val Cys Gly His Val Asp
                165                 170                 175

Val Thr Asp Ala Trp His Gln Ser Asp His Asp Pro Gly Pro Trp
            180                 185                 190

Phe Pro Trp Asp Lys Phe Met Ala Val Val Asn Gly Ser Gly Asp
        195                 200                 205

Ser Gly Glu Leu Thr Val Ala Asp Val Lys Ala Leu His Asp Gln Ile
    210                 215                 220

Lys Gln Leu Ser Ala Gln Leu Thr Gly Ser Val Asn Lys Leu His His
225                 230                 235                 240
```

```
Asp Val Gly Val Val Gln Val Gln Asn Gly Asp Leu Gly Lys Arg Val
                245                 250                 255

Asp Ala Leu Ser Trp Val Lys Asn Pro Val Thr Gly Lys Leu Trp Arg
            260                 265                 270

Thr Lys Asp Ala Leu Trp Ser Val Trp Tyr Tyr Val Leu Glu Cys Arg
        275                 280                 285

Ser Arg Leu Asp Arg Leu Glu Ser Ala Val Asn Asp Leu Lys Lys
    290                 295                 300

<210> SEQ ID NO 89
<211> LENGTH: 503
<212> TYPE: PRT
<213> ORGANISM: Unknown
<220> FEATURE:
<223> OTHER INFORMATION: LysK-PK (PK C-terminal)

<400> SEQUENCE: 89

Ala Lys Thr Gln Ala Glu Ile Asn Lys Arg Leu Asp Ala Tyr Ala Lys
1               5                   10                  15

Gly Thr Val Asp Ser Pro Tyr Arg Val Lys Lys Ala Thr Ser Tyr Asp
            20                  25                  30

Pro Ser Phe Gly Val Met Glu Ala Gly Ala Ile Asp Ala Asp Gly Tyr
        35                  40                  45

Tyr His Ala Gln Cys Gln Asp Leu Ile Thr Asp Tyr Val Leu Trp Leu
    50                  55                  60

Thr Asp Asn Lys Val Arg Thr Trp Gly Asn Ala Lys Asp Gln Ile Lys
65                  70                  75                  80

Gln Ser Tyr Gly Thr Gly Phe Lys Ile His Glu Asn Lys Pro Ser Thr
                85                  90                  95

Val Pro Lys Lys Gly Trp Ile Ala Val Phe Thr Ser Gly Ser Tyr Glu
            100                 105                 110

Gln Trp Gly His Ile Gly Ile Val Tyr Asp Gly Gly Asn Thr Ser Thr
        115                 120                 125

Phe Thr Ile Leu Glu Gln Asn Trp Asn Gly Tyr Ala Asn Lys Lys Pro
    130                 135                 140

Thr Lys Arg Val Asp Asn Tyr Tyr Gly Leu Thr His Phe Ile Glu Ile
145                 150                 155                 160

Pro Val Lys Ala Gly Thr Thr Val Lys Lys Glu Thr Ala Lys Lys Ser
                165                 170                 175

Ala Ser Lys Thr Pro Ala Pro Lys Lys Ala Thr Leu Lys Val Ser
            180                 185                 190

Lys Asn His Ile Asn Tyr Thr Met Asp Lys Arg Gly Lys Lys Pro Glu
    195                 200                 205

Gly Met Val Ile His Asn Asp Ala Gly Arg Ser Ser Gly Gln Gln Tyr
    210                 215                 220

Glu Asn Ser Leu Ala Asn Ala Gly Tyr Ala Arg Tyr Ala Asn Gly Ile
225                 230                 235                 240

Ala His Tyr Tyr Gly Ser Glu Gly Tyr Val Trp Glu Ala Ile Asp Ala
                245                 250                 255

Lys Asn Gln Ile Ala Trp His Thr Gly Asp Gly Thr Gly Ala Asn Ser
            260                 265                 270

Gly Asn Phe Arg Phe Ala Gly Ile Glu Val Cys Gln Ser Met Ser Ala
        275                 280                 285

Ser Asp Ala Gln Phe Leu Lys Asn Glu Gln Ala Val Phe Gln Phe Thr
    290                 295                 300
```

```
Ala Glu Lys Phe Lys Glu Trp Gly Leu Thr Pro Asn Arg Lys Thr Val
305                 310                 315                 320

Arg Leu His Met Glu Phe Val Pro Thr Ala Cys Pro His Arg Ser Met
                325                 330                 335

Val Leu His Thr Gly Phe Asn Pro Val Thr Gln Gly Arg Pro Ser Gln
            340                 345                 350

Ala Ile Met Asn Lys Leu Lys Asp Tyr Phe Ile Lys Gln Ile Lys Asn
        355                 360                 365

Tyr Met Asp Lys Gly Thr Ser Ser Thr Val Val Lys Asp Gly Lys
    370                 375                 380

Thr Ser Ser Ala Ser Thr Pro Ala Thr Arg Pro Val Thr Gly Ser Trp
385                 390                 395                 400

Lys Lys Asn Gln Tyr Gly Thr Trp Tyr Lys Pro Glu Asn Ala Thr Phe
                405                 410                 415

Val Asn Gly Asn Gln Pro Ile Val Thr Arg Ile Gly Ser Pro Phe Leu
            420                 425                 430

Asn Ala Pro Val Gly Gly Asn Leu Pro Ala Gly Ala Thr Ile Val Tyr
        435                 440                 445

Asp Glu Val Cys Ile Gln Ala Gly His Ile Trp Ile Gly Tyr Asn Ala
    450                 455                 460

Tyr Asn Gly Asn Arg Val Tyr Cys Pro Val Arg Thr Cys Gln Gly Val
465                 470                 475                 480

Pro Pro Asn Gln Ile Pro Gly Val Ala Trp Gly Val Phe Lys Lys Arg
                485                 490                 495

Lys Lys Arg Lys Lys Arg Lys
            500

<210> SEQ ID NO 90
<211> LENGTH: 252
<212> TYPE: PRT
<213> ORGANISM: Unknown
<220> FEATURE:
<223> OTHER INFORMATION: Lss-PK (PK C-terminal)

<400> SEQUENCE: 90

His Glu His Ser Ala Gln Trp Leu Asn Asn Tyr Lys Lys Gly Tyr Gly
1               5                   10                  15

Tyr Gly Pro Tyr Pro Leu Gly Ile Asn Gly Gly Met His Tyr Gly Val
            20                  25                  30

Asp Phe Phe Met Asn Ile Gly Thr Pro Val Lys Ala Ile Ser Ser Gly
        35                  40                  45

Lys Ile Val Glu Ala Gly Trp Ser Asn Tyr Gly Gly Asn Gln Ile
    50                  55                  60

Gly Leu Ile Glu Asn Asp Gly Val His Arg Gln Trp Tyr Met His Leu
65                  70                  75                  80

Ser Lys Tyr Asn Val Lys Val Gly Asp Tyr Val Lys Ala Gly Gln Ile
                85                  90                  95

Ile Gly Trp Ser Gly Ser Thr Gly Tyr Ser Thr Ala Pro His Leu His
            100                 105                 110

Phe Gln Arg Met Val Asn Ser Phe Ser Asn Ser Thr Ala Gln Asp Pro
        115                 120                 125

Met Pro Phe Leu Lys Ser Ala Gly Tyr Gly Lys Ala Gly Gly Thr Val
    130                 135                 140

Thr Pro Thr Pro Asn Thr Gly Trp Lys Thr Asn Lys Tyr Gly Thr Leu
145                 150                 155                 160
```

Tyr Lys Ser Glu Ser Ala Ser Phe Thr Pro Asn Thr Asp Ile Ile Thr
                165                 170                 175

Arg Thr Thr Gly Pro Phe Arg Ser Met Pro Gln Ser Gly Val Leu Lys
            180                 185                 190

Ala Gly Gln Thr Ile His Tyr Asp Glu Val Met Lys Gln Asp Gly His
        195                 200                 205

Val Trp Val Gly Tyr Thr Gly Asn Ser Gly Gln Arg Ile Tyr Leu Pro
    210                 215                 220

Val Arg Thr Trp Asn Lys Ser Thr Asn Thr Leu Gly Val Leu Trp Gly
225                 230                 235                 240

Thr Ile Lys Lys Arg Lys Arg Lys Lys Arg Lys
                245                 250

<210> SEQ ID NO 91
<211> LENGTH: 1017
<212> TYPE: DNA
<213> ORGANISM: Unknown
<220> FEATURE:
<223> OTHER INFORMATION: Cpl-1

<400> SEQUENCE: 91
atggtgaaaa aaaacgatct gttcgttgac gtgtcttccc acaacggtta cgatatcact      60
ggcattctgg aacagatggg caccaccaac accattatca aaatctccga aagcacgacc     120
tatctgaacc cgtgtctgtc tgcccaggta gaacagtcta acccaattgg cttctaccat     180
ttcgcacgtt tcggtggtga tgtagccgaa gcggaacgtg aagcgcagtt ctttctggat     240
aacgtgccga tgcaggttaa atacctggtt ctggactatg aagacgatcc gtctggtgac     300
gcacaggcaa acaccaacgc gtgcctgcgt ttcatgcaga tgattgcaga cgctggctac     360
aaaccgatct attactctta caaccgttc acccacgata cgtcgatta ccagcagatt      420 ctggcgcagt tccgaactc tctgtggatc gcaggttatg gcctgaacga cggtactgcg     480
aactttgagt atttcccaag catggacggc atccgctggt ggcagtattc ctccaacccg     540
ttcgacaaaa acatcgtact gctggacgac gaagaggacg acaaaccgaa aactgctggt     600
acctggaaac aggatagcaa aggctggtgg tttcgtcgta caacggttc tttccgtac      660 aacaaatggg aaaaaatcgg tggtgtttgg tattacttcg actccaaagg ctactgcctg     720
acgagcgaat ggctgaaaga taacgagaaa tggtactatc tcaaagacaa cggtgccatg     780
gctactggtt gggttctggt tggttctgag tggtactaca tggacgattc tggtgctatg     840
gttaccggct gggtgaaata caaaacaac tggtattaca tgacgaacga acgcggtaac     900
atggtgagca cgaattcat caaatccggc aaaggctggt acttcatgaa cactaacggt     960
gaactggcgg ataacccgtc tttcaccaaa gaaccggatg cctgatcac cgtcgct       1017

<210> SEQ ID NO 92
<211> LENGTH: 1023
<212> TYPE: DNA
<213> ORGANISM: Unknown
<220> FEATURE:
<223> OTHER INFORMATION: Ply511

<400> SEQUENCE: 92
atggtgaaat acaccgtgga aaacaaaatc atcgcaggcc tgccgaaagg caaactgaaa      60
ggcgcgaact tcgttattgc tcatgaaacc gcaaactcca atccaccat cgacaacgaa     120 gtcagctata tgactcgcaa ctggaaaaac gcgtttgtga ctcactttgt aggtggcggt     180

```
ggccgtgtcg tacaggtagc gaacgttaac tacgtaagct ggggtgcagg tcagtatgct    240
aacagctatt cctacgcgca ggtagaactg tgtcgtacgt ctaacgcgac cacgttcaaa    300
aaagactacg aggtttattg ccagctgctg gttgacctgg ccaaaaaagc tggtatccca    360
atcaccctgg attctggctc caaaacctct gacaaaggca tcaaatccca caaatgggtt    420
gctgacaaac tggcggtac cactcaccag gacccgtatg cttacctgtc ttcttggggc    480
atttctaaag cccagttcgc ctctgatctg gctaaagttt ctggcggtgg taacaccggt    540
actgctccag caaaaccgtc tactccggca ccaaaaccgt ctactccgtc tactaacctg    600
gacaaactgg gcctggtgga ttacatgaac gcgaaaaaaa tggatagcag ctactccaac    660
cgtgacaaac tggcgaaaca gtacggtatc gcaaactata gcggtaccgc ctctcagaac    720
accaccctgc tctctaaaat caaaggcggt gcaccaaaac caagcactcc agcgccaaaa    780
ccgtctacct ccacggctaa aaaaatctac ttcccgccga caaaggtaa ctggtccgta    840 tacccgacca caaagctcc ggtgaaagcc aacgcaattg tgctatcaa cccgaccaaa    900 ttcggtggcc tgacctatac gattcagaaa gatcgcggca acgtgtgta cgaaattcag    960 accgatcagt tcggtcgtgt tcaggtttac ggtgctccgt ctaccggtgc ggttatcaaa   1020
aaa                                                                 1023

<210> SEQ ID NO 93
<211> LENGTH: 1485
<212> TYPE: DNA
<213> ORGANISM: Unknown
<220> FEATURE:
<223> OTHER INFORMATION: LysK

<400> SEQUENCE: 93
atggccaaaa cccaggctga atcaacaaa cgtctggacg cgtacgctaa aggcactgtt     60
gattctccgt accgtgtgaa aaaagccacc tcctatgatc cgtcttttgg tgtaatggaa    120
gcgggcgcta ttgacgctga cggctattac catgcccagt gccaggatct gatcacggac    180
tatgttctgt ggctgaccga caacaaagtt cgtacctggg gtaacgcgaa agatcagatc    240
aaacagtcct acggcaccgg tttcaaaatc cacgagaaca aaccgtccac cgttccgaaa    300
aaaggttgga tcgctgtctt caccctctgg tcctatgaac agtggggtca tcggtatc     360 gtgtacgatg gtggtaacac cagcacgttc accatcctgg aacagaactg gaacggttac    420
gcgaacaaaa aaccgaccaa acgtgtggat aactactacg gcctgacgca cttcattgaa    480
atcccggtga agctggtac taccgtgaaa aaagagacgg cgaaaaaatc tgcctctaaa    540
actccggcac cgaaaaaaaa agccacccctg aaagtctcta aaaccacat caactacacg    600 atggacaaac gcggtaaaaa accggaaggc atggtcattc acaacgatgc tggtcgctct    660
tccggccagc agtatgaaaa cagcctggct aacgcaggtt acgcacgtta cgcaaacggt    720
attgcgcact actacggttc tgaaggctat gtgtgggaag ctatcgacgc gaaaaaccag    780
attgcgtggc acaccggcga cggtaccggc gctaactctg caacttccg ctttgcaggc    840 attgaggtat gtcagtctat gtccgcgtct gatgcgcagt cctgaaaaaa cgaacaggct    900
gtcttccagt tcactgcgga gaaattcaaa gaatggggtc tgactccgaa ccgcaaaact    960
gtacgcctgc acatggaatt tgttccgact gcatgtccgc atcgtagcat ggttctgcac   1020
actggcttta acccggttac tcagggtcgt ccgagccagg cgatcatgaa caaactgaaa   1080
gactacttta tcaaacagat caaaaactac atggataaag caccagctc cagcaccgta   1140 gttaaagatg gcaaaacttc tagcgcgtcc actccggcaa cccgtccggt tactggttct   1200
```

```
tggaaaaaaa accagtatgg tacctggtac aaaccggaaa acgccacctt cgtaaacggc    1260
aaccagccga ttgtaactcg tatcggttct ccgtttctga acgcgccggt tggcggcaac    1320
ctgccggcag gtgctacgat tgtgtacgac gaagtttgca ttcaggcagg ccacatttgg    1380
atcggctaca acgcgtataa cggtaaccgc gtttactgcc cggtacgtac ctgtcagggt    1440
gttccgccga accagattcc gggcgtggca tggggtgttt tcaaa                    1485
```

<210> SEQ ID NO 94
<211> LENGTH: 735
<212> TYPE: DNA
<213> ORGANISM: Unknown
<220> FEATURE:
<223> OTHER INFORMATION: Lss

<400> SEQUENCE: 94

```
atggcccatg agcattcagc ccaatggctc aataattata aaaaggata tgggtatggt    60 ccttatccct tggggattaa tggtggtatg cattatgggg tcgacttttt tatgaacatt    120
ggtacccccg ttaaagcaat ctcatctggg aaaatagttg aagctggatg gtcaaactac   180
ggtggcggca atcagattgg cctgatagaa atgacggag ttcaccgtca gtggtacatg    240
cacctttcga agtataacgt caaggtaggc gactatgtaa aggctggtca aattatcggt    300
tggtcaggaa gtacaggata tagtaccgcg ccccacctcc atttccagcg gatggtgaac    360

tcattctcga actctaccgc acaggatccg atgccgttcc tgaaaagtgc aggctatggc    420
aaagctgggg gcacagtaac tcccaccccg aacaccggat ggaagacaaa taagtacggt   480

acactttaca aaagcgagtc agcatcatt acaccgaata cggacatcat cacacgtact    540
acaggaccgt tcaggtcgat gcctcaatct ggggtcctca aggctggaca gacgatacac    600

tacgacgagg tcatgaagca ggacgggcat gtctgggtcg gtacactgg aaactctgga    660 caacgaattt atcttccggt tcgaacatgg aacaaatcaa cgaatacatt gggcgtgcta    720

tggggacca taaag                                                     735
```

<210> SEQ ID NO 95
<211> LENGTH: 528
<212> TYPE: DNA
<213> ORGANISM: Unknown
<220> FEATURE:
<223> OTHER INFORMATION: Pseudin 1

<400> SEQUENCE: 95

```
aacccgatta tcgatggcat tatcgcgctg gaaggaggtt acgtctttaa tccgaaagat    60
aagggtggag caacacattg gggtattaca gaagcgacgg cacgagcaca tggttatgca    120
ggagacatgc gtgatctaac tcatgccgaa gcctacgcaa tacttgagga ggattactgg    180

atcaaaccgg gttttgatgt tatctcaacg ctgtcgtggc ctgtgagctt tgaattgtgt    240
gatgcagcgg ttaacatagg tgcataccac cctagtgcct ggttacagag atggcttaac    300
gtgttcaatc acgaaggcaa acgctatcca gacattcatg tagacggcaa cattggtccc    360
aggactttag cagccttaga acattacttg gcttggagag ggcaagaagg tgaagctgta    420

ctggtgaaag ctctgaattg cagccaaggg acctactatc taaacgtcgc tgagaagaac    480
cacaacaacg aacagttcat ctacggttgg atcaagaatc gtgtgacc                528
```

<210> SEQ ID NO 96
<211> LENGTH: 81
<212> TYPE: DNA
```

```
<213> ORGANISM: Unknown
<220> FEATURE:
<223> OTHER INFORMATION: WLBU2-Variant

<400> SEQUENCE: 96
aaacgctggg ttaaacgcgt gaaacgtgtc aaacgttggg tcaaacgtgt tgtccgtgta    60
gtgaaacgtt gggtgaaacg c                                              81

<210> SEQ ID NO 97
<211> LENGTH: 111
<212> TYPE: DNA
<213> ORGANISM: Unknown
<220> FEATURE:
<223> OTHER INFORMATION: LL-37

<400> SEQUENCE: 97
ctcctgggtg acttctttcg caaatccaaa gagaaaatcg gcaaagagtt caaacgtatc    60
gtgcagcgca ttaaagactt tctgcgtaac ctggttccgc gtaccgaatc t            111

<210> SEQ ID NO 98
<211> LENGTH: 39
<212> TYPE: DNA
<213> ORGANISM: Unknown
<220> FEATURE:
<223> OTHER INFORMATION: Indolicidin

<400> SEQUENCE: 98
atcctgccgt ggaaatggcc gtggtggcca tggcgtcgc                           39

<210> SEQ ID NO 99
<211> LENGTH: 69
<212> TYPE: DNA
<213> ORGANISM: Unknown
<220> FEATURE:
<223> OTHER INFORMATION: Magainin

<400> SEQUENCE: 99
ggtatcggca aattcctgca ctccgcaaaa aaattcggca agctttcgt gggcgaaatt     60 atgaactct                                                            69

<210> SEQ ID NO 100
<211> LENGTH: 75
<212> TYPE: DNA
<213> ORGANISM: Unknown
<220> FEATURE:
<223> OTHER INFORMATION: Pleurocidin

<400> SEQUENCE: 100
ggctggggtt ctttctttaa aaaagcggct cacgttggca acatgtagg taaagcagct     60 ctgacccact atctg                                                     75

<210> SEQ ID NO 101
<211> LENGTH: 108
<212> TYPE: DNA
<213> ORGANISM: Unknown
<220> FEATURE:
<223> OTHER INFORMATION: Cecropin A (A. aegypti)

<400> SEQUENCE: 101
ggcggcctga aaaactggg caaaaaactg gaaggtgccg gcaaacgtgt gttcaacgct     60
gcagaaaaag cactgccggt tgtagctggt gctaaagctc tccgtaaa               108
```

```
<210> SEQ ID NO 102
<211> LENGTH: 120
<212> TYPE: DNA
<213> ORGANISM: Unknown
<220> FEATURE:
<223> OTHER INFORMATION: Cecropin A (D. melanogaster)

<400> SEQUENCE: 102
ggctggctga aaaaaattgg caaaaaaatc gaacgcgtgg gccagcacac gcgtgatgca      60
accatccagg gtctgggtat cccacagcag gcagctaacg tagccgcgac tgctcgtggt     120

<210> SEQ ID NO 103
<211> LENGTH: 117
<212> TYPE: DNA
<213> ORGANISM: Unknown
<220> FEATURE:
<223> OTHER INFORMATION: Sarcotoxin IA

<400> SEQUENCE: 103
ggatggctca aaagattgg caagaaaatc gagcgagtcg gtcagcatac gcgtgatgca      60
actatccagg gtttaggtat cgcacagcaa gcagctaatg tagcagctac tgctcgg      117

<210> SEQ ID NO 104
<211> LENGTH: 27
<212> TYPE: DNA
<213> ORGANISM: Unknown
<220> FEATURE:
<223> OTHER INFORMATION: PK

<400> SEQUENCE: 104
aagcgtaaga aacgcaaaaa acgcaaa                                          27

<210> SEQ ID NO 105
<211> LENGTH: 15
<212> TYPE: DNA
<213> ORGANISM: Unknown
<220> FEATURE:
<223> OTHER INFORMATION: Synthetic peptide

<400> SEQUENCE: 105
ttctttgtgg cgccg                                                      15

<210> SEQ ID NO 106
<211> LENGTH: 54
<212> TYPE: DNA
<213> ORGANISM: Unknown
<220> FEATURE:
<223> OTHER INFORMATION: PK2

<400> SEQUENCE: 106
aagcgtaaga aacgcaaaaa acgcaaaaaa cgcaaaaaac gcaagaaaag aaaa           54

<210> SEQ ID NO 107
<211> LENGTH: 373
<212> TYPE: PRT
<213> ORGANISM: Unknown
<220> FEATURE:
<223> OTHER INFORMATION: Pseudin1-Cpl1

<400> SEQUENCE: 107
```

Met Gly Leu Asn Thr Leu Lys Lys Val Phe Gln Gly Leu His Glu Ala
1               5                   10                  15

Ile Lys Leu Ile Asn Asn His Val Gln Gly Ser Val Lys Lys Asn Asp
            20                  25                  30

```
Leu Phe Val Asp Val Ser Ser His Asn Gly Tyr Asp Ile Thr Gly Ile
             35                  40                  45

Leu Glu Gln Met Gly Thr Thr Asn Thr Ile Ile Lys Ile Ser Glu Ser
 50                  55                  60

Thr Thr Tyr Leu Asn Pro Cys Leu Ser Ala Gln Val Glu Gln Ser Asn
 65                  70                  75                  80

Pro Ile Gly Phe Tyr His Phe Ala Arg Phe Gly Asp Val Ala Glu
                 85                  90                  95

Ala Glu Arg Glu Ala Gln Phe Phe Leu Asp Asn Val Pro Met Gln Val
                100                 105                 110

Lys Tyr Leu Val Leu Asp Tyr Glu Asp Pro Ser Gly Asp Ala Gln
                115                 120                 125

Ala Asn Thr Asn Ala Cys Leu Arg Phe Met Gln Met Ile Ala Asp Ala
        130                 135                 140

Gly Tyr Lys Pro Ile Tyr Tyr Ser Tyr Lys Pro Phe Thr His Asp Asn
145                 150                 155                 160

Val Asp Tyr Gln Gln Ile Leu Ala Gln Phe Pro Asn Ser Leu Trp Ile
                165                 170                 175

Ala Gly Tyr Gly Leu Asn Asp Gly Thr Ala Asn Phe Glu Tyr Phe Pro
                180                 185                 190

Ser Met Asp Gly Ile Arg Trp Trp Gln Tyr Ser Ser Asn Pro Phe Asp
            195                 200                 205

Lys Asn Ile Val Leu Leu Asp Asp Glu Glu Asp Lys Pro Lys Thr
            210                 215                 220

Ala Gly Thr Trp Lys Gln Asp Ser Lys Gly Trp Trp Phe Arg Arg Asn
225                 230                 235                 240

Asn Gly Ser Phe Pro Tyr Asn Lys Trp Glu Lys Ile Gly Gly Val Trp
                245                 250                 255

Tyr Tyr Phe Asp Ser Lys Gly Tyr Cys Leu Thr Ser Glu Trp Leu Lys
            260                 265                 270

Asp Asn Glu Lys Trp Tyr Tyr Leu Lys Asp Asn Gly Ala Met Ala Thr
            275                 280                 285

Gly Trp Val Leu Val Gly Ser Glu Trp Tyr Tyr Met Asp Asp Ser Gly
290                 295                 300

Ala Met Val Thr Gly Trp Val Lys Tyr Lys Asn Asn Trp Tyr Tyr Met
305                 310                 315                 320

Thr Asn Glu Arg Gly Asn Met Val Ser Asn Glu Phe Ile Lys Ser Gly
                325                 330                 335

Lys Gly Trp Tyr Phe Met Asn Thr Asn Gly Glu Leu Ala Asp Asn Pro
            340                 345                 350

Ser Phe Thr Lys Glu Pro Asp Gly Leu Ile Thr Val Ala Leu Glu His
            355                 360                 365

His His His His His
        370

<210> SEQ ID NO 108
<211> LENGTH: 376
<212> TYPE: PRT
<213> ORGANISM: Unknown
<220> FEATURE:
<223> OTHER INFORMATION: WLBU2-Variant-Cpl1

<400> SEQUENCE: 108

Met Lys Arg Trp Val Lys Arg Val Lys Arg Val Lys Arg Trp Val Lys
 1               5                  10                  15
```

```
Arg Val Val Arg Val Val Lys Arg Trp Val Lys Arg Gly Ser Val Lys
             20                  25                  30

Lys Asn Asp Leu Phe Val Asp Val Ser Ser His Asn Gly Tyr Asp Ile
         35                  40                  45

Thr Gly Ile Leu Glu Gln Met Gly Thr Thr Asn Thr Ile Ile Lys Ile
 50                  55                  60

Ser Glu Ser Thr Thr Tyr Leu Asn Pro Cys Leu Ser Ala Gln Val Glu
 65                  70                  75                  80

Gln Ser Asn Pro Ile Gly Phe Tyr His Phe Ala Arg Phe Gly Gly Asp
                 85                  90                  95

Val Ala Glu Ala Glu Arg Glu Ala Gln Phe Phe Leu Asp Asn Val Pro
             100                 105                 110

Met Gln Val Lys Tyr Leu Val Leu Asp Tyr Glu Asp Asp Pro Ser Gly
             115                 120                 125

Asp Ala Gln Ala Asn Thr Asn Ala Cys Leu Arg Phe Met Gln Met Ile
130                 135                 140

Ala Asp Ala Gly Tyr Lys Pro Ile Tyr Tyr Ser Tyr Lys Pro Phe Thr
145                 150                 155                 160

His Asp Asn Val Asp Tyr Gln Gln Ile Leu Ala Gln Phe Pro Asn Ser
                 165                 170                 175

Leu Trp Ile Ala Gly Tyr Gly Leu Asn Asp Gly Thr Ala Asn Phe Glu
             180                 185                 190

Tyr Phe Pro Ser Met Asp Gly Ile Arg Trp Trp Gln Tyr Ser Ser Asn
             195                 200                 205

Pro Phe Asp Lys Asn Ile Val Leu Leu Asp Asp Glu Glu Asp Asp Lys
210                 215                 220

Pro Lys Thr Ala Gly Thr Trp Lys Gln Asp Ser Lys Gly Trp Trp Phe
225                 230                 235                 240

Arg Arg Asn Asn Gly Ser Phe Pro Tyr Asn Lys Trp Glu Lys Ile Gly
                 245                 250                 255

Gly Val Trp Tyr Tyr Phe Asp Ser Lys Gly Tyr Cys Leu Thr Ser Glu
             260                 265                 270

Trp Leu Lys Asp Asn Glu Lys Trp Tyr Tyr Leu Lys Asp Asn Gly Ala
             275                 280                 285

Met Ala Thr Gly Trp Val Leu Val Gly Ser Glu Trp Tyr Tyr Met Asp
290                 295                 300

Asp Ser Gly Ala Met Val Thr Gly Trp Val Lys Tyr Lys Asn Asn Trp
305                 310                 315                 320

Tyr Tyr Met Thr Asn Glu Arg Gly Asn Met Val Ser Asn Glu Phe Ile
                 325                 330                 335

Lys Ser Gly Lys Gly Trp Tyr Phe Met Asn Thr Asn Gly Glu Leu Ala
             340                 345                 350

Asp Asn Pro Ser Phe Thr Lys Glu Pro Asp Gly Leu Ile Thr Val Ala
             355                 360                 365

Leu Glu His His His His His
    370                 375

<210> SEQ ID NO 109
<211> LENGTH: 386
<212> TYPE: PRT
<213> ORGANISM: Unknown
<220> FEATURE:
<223> OTHER INFORMATION: LL-37-Cpl1

<400> SEQUENCE: 109
```

```
Met Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser Gly Ser Val Lys Lys Asn Asp Leu Phe Val
            35                  40                  45

Asp Val Ser Ser His Asn Gly Tyr Asp Ile Thr Gly Ile Leu Glu Gln
        50                  55                  60

Met Gly Thr Thr Asn Thr Ile Ile Lys Ile Ser Glu Ser Thr Thr Tyr
65                  70                  75                  80

Leu Asn Pro Cys Leu Ser Ala Gln Val Glu Gln Ser Asn Pro Ile Gly
                85                  90                  95

Phe Tyr His Phe Ala Arg Phe Gly Gly Asp Val Ala Glu Ala Glu Arg
            100                 105                 110

Glu Ala Gln Phe Phe Leu Asp Asn Val Pro Met Gln Val Lys Tyr Leu
            115                 120                 125

Val Leu Asp Tyr Glu Asp Pro Ser Gly Asp Ala Gln Ala Asn Thr
130                 135                 140

Asn Ala Cys Leu Arg Phe Met Gln Met Ile Ala Asp Ala Gly Tyr Lys
145                 150                 155                 160

Pro Ile Tyr Tyr Ser Tyr Lys Pro Phe Thr His Asp Asn Val Asp Tyr
                165                 170                 175

Gln Gln Ile Leu Ala Gln Phe Pro Asn Ser Leu Trp Ile Ala Gly Tyr
            180                 185                 190

Gly Leu Asn Asp Gly Thr Ala Asn Phe Glu Tyr Phe Pro Ser Met Asp
            195                 200                 205

Gly Ile Arg Trp Trp Gln Tyr Ser Ser Asn Pro Phe Asp Lys Asn Ile
            210                 215                 220

Val Leu Leu Asp Asp Glu Glu Asp Asp Lys Pro Lys Thr Ala Gly Thr
225                 230                 235                 240

Trp Lys Gln Asp Ser Lys Gly Trp Trp Phe Arg Arg Asn Asn Gly Ser
                245                 250                 255

Phe Pro Tyr Asn Lys Trp Glu Lys Ile Gly Gly Val Trp Tyr Tyr Phe
            260                 265                 270

Asp Ser Lys Gly Tyr Cys Leu Thr Ser Glu Trp Leu Lys Asp Asn Glu
            275                 280                 285

Lys Trp Tyr Tyr Leu Lys Asp Asn Gly Ala Met Ala Thr Gly Trp Val
            290                 295                 300

Leu Val Gly Ser Glu Trp Tyr Tyr Met Asp Asp Ser Gly Ala Met Val
305                 310                 315                 320

Thr Gly Trp Val Lys Tyr Lys Asn Asn Trp Tyr Tyr Met Thr Asn Glu
                325                 330                 335

Arg Gly Asn Met Val Ser Asn Glu Phe Ile Lys Ser Gly Lys Gly Trp
            340                 345                 350

Tyr Phe Met Asn Thr Asn Gly Glu Leu Ala Asp Asn Pro Ser Phe Thr
            355                 360                 365

Lys Glu Pro Asp Gly Leu Ile Thr Val Ala Leu Glu His His His His
            370                 375                 380

His His
385

<210> SEQ ID NO 110
<211> LENGTH: 362
<212> TYPE: PRT
```

-continued

<213> ORGANISM: Unknown
<220> FEATURE:
<223> OTHER INFORMATION: Indolicidin-Cpl1

<400> SEQUENCE: 110

```
Met Ile Leu Pro Trp Lys Trp Pro Trp Trp Pro Trp Arg Arg Gly Ser
1               5                   10                  15

Val Lys Lys Asn Asp Leu Phe Val Asp Val Ser Ser His Asn Gly Tyr
            20                  25                  30

Asp Ile Thr Gly Ile Leu Glu Gln Met Gly Thr Thr Asn Thr Ile Ile
        35                  40                  45

Lys Ile Ser Glu Ser Thr Thr Tyr Leu Asn Pro Cys Leu Ser Ala Gln
    50                  55                  60

Val Glu Gln Ser Asn Pro Ile Gly Phe Tyr His Phe Ala Arg Phe Gly
65                  70                  75                  80

Gly Asp Val Ala Glu Ala Glu Arg Glu Ala Gln Phe Phe Leu Asp Asn
                85                  90                  95

Val Pro Met Gln Val Lys Tyr Leu Val Leu Asp Tyr Glu Asp Asp Pro
            100                 105                 110

Ser Gly Asp Ala Gln Ala Asn Thr Asn Ala Cys Leu Arg Phe Met Gln
        115                 120                 125

Met Ile Ala Asp Ala Gly Tyr Lys Pro Ile Tyr Tyr Ser Tyr Lys Pro
    130                 135                 140

Phe Thr His Asp Asn Val Asp Tyr Gln Gln Ile Leu Ala Gln Phe Pro
145                 150                 155                 160

Asn Ser Leu Trp Ile Ala Gly Tyr Gly Leu Asn Asp Gly Thr Ala Asn
                165                 170                 175

Phe Glu Tyr Phe Pro Ser Met Asp Gly Ile Arg Trp Trp Gln Tyr Ser
            180                 185                 190

Ser Asn Pro Phe Asp Lys Asn Ile Val Leu Leu Asp Asp Glu Glu Asp
        195                 200                 205

Asp Lys Pro Lys Thr Ala Gly Thr Trp Lys Gln Asp Ser Lys Gly Trp
    210                 215                 220

Trp Phe Arg Arg Asn Asn Gly Ser Phe Pro Tyr Asn Lys Trp Glu Lys
225                 230                 235                 240

Ile Gly Gly Val Trp Tyr Tyr Phe Asp Ser Lys Gly Tyr Cys Leu Thr
                245                 250                 255

Ser Glu Trp Leu Lys Asp Asn Glu Lys Trp Tyr Tyr Leu Lys Asp Asn
            260                 265                 270

Gly Ala Met Ala Thr Gly Trp Val Leu Val Gly Ser Glu Trp Tyr Tyr
        275                 280                 285

Met Asp Asp Ser Gly Ala Met Val Thr Gly Trp Val Lys Tyr Lys Asn
    290                 295                 300

Asn Trp Tyr Tyr Met Thr Asn Glu Arg Gly Asn Met Val Ser Asn Glu
305                 310                 315                 320

Phe Ile Lys Ser Gly Lys Gly Trp Tyr Phe Met Asn Thr Asn Gly Glu
                325                 330                 335

Leu Ala Asp Asn Pro Ser Phe Thr Lys Glu Pro Asp Gly Leu Ile Thr
            340                 345                 350

Val Ala Leu Glu His His His His His His
        355                 360
```

<210> SEQ ID NO 111
<211> LENGTH: 372
<212> TYPE: PRT

<213> ORGANISM: Unknown
<220> FEATURE:
<223> OTHER INFORMATION: Magainin-Cp11

<400> SEQUENCE: 111

```
Met Gly Ile Gly Lys Phe Leu His Ser Ala Lys Lys Phe Gly Lys Ala
1               5                   10                  15

Phe Val Gly Glu Ile Met Asn Ser Gly Ser Val Lys Lys Asn Asp Leu
            20                  25                  30

Phe Val Asp Val Ser Ser His Asn Gly Tyr Asp Ile Thr Gly Ile Leu
        35                  40                  45

Glu Gln Met Gly Thr Thr Asn Thr Ile Ile Lys Ile Ser Glu Ser Thr
    50                  55                  60

Thr Tyr Leu Asn Pro Cys Leu Ser Ala Gln Val Glu Gln Ser Asn Pro
65                  70                  75                  80

Ile Gly Phe Tyr His Phe Ala Arg Phe Gly Gly Asp Val Ala Glu Ala
            85                  90                  95

Glu Arg Glu Ala Gln Phe Phe Leu Asp Asn Val Pro Met Gln Val Lys
            100                 105                 110

Tyr Leu Val Leu Asp Tyr Glu Asp Pro Ser Gly Asp Ala Gln Ala
            115                 120                 125

Asn Thr Asn Ala Cys Leu Arg Phe Met Gln Met Ile Ala Asp Ala Gly
    130                 135                 140

Tyr Lys Pro Ile Tyr Tyr Ser Tyr Lys Pro Phe Thr His Asp Asn Val
145                 150                 155                 160

Asp Tyr Gln Gln Ile Leu Ala Gln Phe Pro Asn Ser Leu Trp Ile Ala
            165                 170                 175

Gly Tyr Gly Leu Asn Asp Gly Thr Ala Asn Phe Glu Tyr Phe Pro Ser
            180                 185                 190

Met Asp Gly Ile Arg Trp Trp Gln Tyr Ser Ser Asn Pro Phe Asp Lys
            195                 200                 205

Asn Ile Val Leu Leu Asp Asp Glu Glu Asp Lys Pro Lys Thr Ala
    210                 215                 220

Gly Thr Trp Lys Gln Asp Ser Lys Gly Trp Trp Phe Arg Arg Asn Asn
225                 230                 235                 240

Gly Ser Phe Pro Tyr Asn Lys Trp Glu Lys Ile Gly Gly Val Trp Tyr
                245                 250                 255

Tyr Phe Asp Ser Lys Gly Tyr Cys Leu Thr Ser Glu Trp Leu Lys Asp
            260                 265                 270

Asn Glu Lys Trp Tyr Tyr Leu Lys Asp Asn Gly Ala Met Ala Thr Gly
            275                 280                 285

Trp Val Leu Val Gly Ser Glu Trp Tyr Tyr Met Asp Asp Ser Gly Ala
    290                 295                 300

Met Val Thr Gly Trp Val Lys Tyr Lys Asn Asn Trp Tyr Tyr Met Thr
305                 310                 315                 320

Asn Glu Arg Gly Asn Met Val Ser Asn Glu Phe Ile Lys Ser Gly Lys
            325                 330                 335

Gly Trp Tyr Phe Met Asn Thr Asn Gly Glu Leu Ala Asp Asn Pro Ser
            340                 345                 350

Phe Thr Lys Glu Pro Asp Gly Leu Ile Thr Val Ala Leu Glu His His
            355                 360                 365

His His His His
    370
```

```
<210> SEQ ID NO 112
<211> LENGTH: 374
<212> TYPE: PRT
<213> ORGANISM: Unknown
<220> FEATURE:
<223> OTHER INFORMATION: Pleurocidin-Cpl1

<400> SEQUENCE: 112

Met Gly Trp Gly Ser Phe Phe Lys Lys Ala Ala His Val Gly Lys His
1               5                   10                  15

Val Gly Lys Ala Ala Leu Thr His Tyr Leu Gly Ser Val Lys Lys Asn
            20                  25                  30

Asp Leu Phe Val Asp Val Ser Ser His Asn Gly Tyr Asp Ile Thr Gly
        35                  40                  45

Ile Leu Glu Gln Met Gly Thr Thr Asn Thr Ile Ile Lys Ile Ser Glu
    50                  55                  60

Ser Thr Thr Tyr Leu Asn Pro Cys Leu Ser Ala Gln Val Glu Gln Ser
65                  70                  75                  80

Asn Pro Ile Gly Phe Tyr His Phe Ala Arg Phe Gly Gly Asp Val Ala
                85                  90                  95

Glu Ala Glu Arg Glu Ala Gln Phe Phe Leu Asp Asn Val Pro Met Gln
            100                 105                 110

Val Lys Tyr Leu Val Leu Asp Tyr Glu Asp Asp Pro Ser Gly Asp Ala
        115                 120                 125

Gln Ala Asn Thr Asn Ala Cys Leu Arg Phe Met Gln Met Ile Ala Asp
    130                 135                 140

Ala Gly Tyr Lys Pro Ile Tyr Tyr Ser Tyr Lys Pro Phe Thr His Asp
145                 150                 155                 160

Asn Val Asp Tyr Gln Gln Ile Leu Ala Gln Phe Pro Asn Ser Leu Trp
                165                 170                 175

Ile Ala Gly Tyr Gly Leu Asn Asp Gly Thr Ala Asn Phe Glu Tyr Phe
            180                 185                 190

Pro Ser Met Asp Gly Ile Arg Trp Trp Gln Tyr Ser Ser Asn Pro Phe
        195                 200                 205

Asp Lys Asn Ile Val Leu Leu Asp Asp Glu Glu Asp Lys Pro Lys
210                 215                 220

Thr Ala Gly Thr Trp Lys Gln Asp Ser Lys Gly Trp Trp Phe Arg Arg
225                 230                 235                 240

Asn Asn Gly Ser Phe Pro Tyr Asn Lys Trp Glu Lys Ile Gly Gly Val
                245                 250                 255

Trp Tyr Tyr Phe Asp Ser Lys Gly Tyr Cys Leu Thr Ser Glu Trp Leu
            260                 265                 270

Lys Asp Asn Glu Lys Trp Tyr Tyr Leu Lys Asp Asn Gly Ala Met Ala
        275                 280                 285

Thr Gly Trp Val Leu Val Gly Ser Glu Trp Tyr Tyr Met Asp Asp Ser
    290                 295                 300

Gly Ala Met Val Thr Gly Trp Val Lys Tyr Lys Asn Asn Trp Tyr Tyr
305                 310                 315                 320

Met Thr Asn Glu Arg Gly Asn Met Val Ser Asn Glu Phe Ile Lys Ser
                325                 330                 335

Gly Lys Gly Trp Tyr Phe Met Asn Thr Asn Gly Glu Leu Ala Asp Asn
            340                 345                 350

Pro Ser Phe Thr Lys Glu Pro Asp Gly Leu Ile Thr Val Ala Leu Glu
        355                 360                 365

His His His His His His
```

370

<210> SEQ ID NO 113
<211> LENGTH: 385
<212> TYPE: PRT
<213> ORGANISM: Unknown
<220> FEATURE:
<223> OTHER INFORMATION: Cecropin A (A.aegypti)-Cp11

<400> SEQUENCE: 113

```
Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ser Val Lys Lys Asn Asp Leu Phe Val Asp
        35                  40                  45

Val Ser Ser His Asn Gly Tyr Asp Ile Thr Gly Ile Leu Glu Gln Met
    50                  55                  60

Gly Thr Thr Asn Thr Ile Ile Lys Ile Ser Glu Ser Thr Thr Tyr Leu
65                  70                  75                  80

Asn Pro Cys Leu Ser Ala Gln Val Glu Gln Ser Asn Pro Ile Gly Phe
                85                  90                  95

Tyr His Phe Ala Arg Phe Gly Gly Asp Val Ala Glu Ala Glu Arg Glu
            100                 105                 110

Ala Gln Phe Phe Leu Asp Asn Val Pro Met Gln Val Lys Tyr Leu Val
        115                 120                 125

Leu Asp Tyr Glu Asp Asp Pro Ser Gly Asp Ala Gln Ala Asn Thr Asn
    130                 135                 140

Ala Cys Leu Arg Phe Met Gln Met Ile Ala Asp Ala Gly Tyr Lys Pro
145                 150                 155                 160

Ile Tyr Tyr Ser Tyr Lys Pro Phe Thr His Asp Asn Val Asp Tyr Gln
                165                 170                 175

Gln Ile Leu Ala Gln Phe Pro Asn Ser Leu Trp Ile Ala Gly Tyr Gly
            180                 185                 190

Leu Asn Asp Gly Thr Ala Asn Phe Glu Tyr Phe Pro Ser Met Asp Gly
        195                 200                 205

Ile Arg Trp Trp Gln Tyr Ser Ser Asn Pro Phe Asp Lys Asn Ile Val
    210                 215                 220

Leu Leu Asp Asp Glu Glu Asp Asp Lys Pro Lys Thr Ala Gly Thr Trp
225                 230                 235                 240

Lys Gln Asp Ser Lys Gly Trp Trp Phe Arg Arg Asn Asn Gly Ser Phe
                245                 250                 255

Pro Tyr Asn Lys Trp Glu Lys Ile Gly Gly Val Trp Tyr Tyr Phe Asp
            260                 265                 270

Ser Lys Gly Tyr Cys Leu Thr Ser Glu Trp Leu Lys Asp Asn Glu Lys
        275                 280                 285

Trp Tyr Tyr Leu Lys Asp Asn Gly Ala Met Ala Thr Gly Trp Val Leu
    290                 295                 300

Val Gly Ser Glu Trp Tyr Tyr Met Asp Asp Ser Gly Ala Met Val Thr
305                 310                 315                 320

Gly Trp Val Lys Tyr Lys Asn Asn Trp Tyr Tyr Met Thr Asn Glu Arg
                325                 330                 335

Gly Asn Met Val Ser Asn Glu Phe Ile Lys Ser Gly Lys Gly Trp Tyr
            340                 345                 350

Phe Met Asn Thr Asn Gly Glu Leu Ala Asp Asn Pro Ser Phe Thr Lys
```

```
                    355                 360                 365
Glu Pro Asp Gly Leu Ile Thr Val Ala Leu Glu His His His His
    370                 375                 380

His
385

<210> SEQ ID NO 114
<211> LENGTH: 370
<212> TYPE: PRT
<213> ORGANISM: Unknown
<220> FEATURE:
<223> OTHER INFORMATION: BuforinII-Cpl1

<400> SEQUENCE: 114

Met Thr Arg Ser Ser Arg Ala Gly Leu Gln Phe Pro Val Gly Arg Val
1               5                   10                  15

His Arg Leu Leu Arg Lys Gly Ser Val Lys Lys Asn Asp Leu Phe Val
            20                  25                  30

Asp Val Ser Ser His Asn Gly Tyr Asp Ile Thr Gly Ile Leu Glu Gln
        35                  40                  45

Met Gly Thr Thr Asn Thr Ile Ile Lys Ile Ser Glu Ser Thr Thr Tyr
    50                  55                  60

Leu Asn Pro Cys Leu Ser Ala Gln Val Glu Gln Ser Asn Pro Ile Gly
65                  70                  75                  80

Phe Tyr His Phe Ala Arg Phe Gly Gly Asp Val Ala Glu Ala Glu Arg
                85                  90                  95

Glu Ala Gln Phe Phe Leu Asp Asn Val Pro Met Gln Val Lys Tyr Leu
            100                 105                 110

Val Leu Asp Tyr Glu Asp Asp Pro Ser Gly Asp Ala Gln Ala Asn Thr
        115                 120                 125

Asn Ala Cys Leu Arg Phe Met Gln Met Ile Ala Asp Ala Gly Tyr Lys
130                 135                 140

Pro Ile Tyr Tyr Ser Tyr Lys Pro Phe Thr His Asp Asn Val Asp Tyr
145                 150                 155                 160

Gln Gln Ile Leu Ala Gln Phe Pro Asn Ser Leu Trp Ile Ala Gly Tyr
                165                 170                 175

Gly Leu Asn Asp Gly Thr Ala Asn Phe Glu Tyr Phe Pro Ser Met Asp
            180                 185                 190

Gly Ile Arg Trp Trp Gln Tyr Ser Ser Asn Pro Phe Asp Lys Asn Ile
        195                 200                 205

Val Leu Leu Asp Asp Glu Glu Asp Lys Pro Lys Thr Ala Gly Thr
    210                 215                 220

Trp Lys Gln Asp Ser Lys Gly Trp Trp Phe Arg Arg Asn Asn Gly Ser
225                 230                 235                 240

Phe Pro Tyr Asn Lys Trp Glu Lys Ile Gly Gly Val Trp Tyr Tyr Phe
                245                 250                 255

Asp Ser Lys Gly Tyr Cys Leu Thr Ser Glu Trp Leu Lys Asp Asn Glu
            260                 265                 270

Lys Trp Tyr Tyr Leu Lys Asp Asn Gly Ala Met Ala Thr Gly Trp Val
        275                 280                 285

Leu Val Gly Ser Glu Trp Tyr Tyr Met Asp Asp Ser Gly Ala Met Val
    290                 295                 300

Thr Gly Trp Val Lys Tyr Lys Asn Asn Trp Tyr Tyr Met Thr Asn Glu
305                 310                 315                 320

Arg Gly Asn Met Val Ser Asn Glu Phe Ile Lys Ser Gly Lys Gly Trp
```

```
              325                 330                 335
Tyr Phe Met Asn Thr Asn Gly Glu Leu Ala Asp Asn Pro Ser Phe Thr
          340                 345                 350

Lys Glu Pro Asp Gly Leu Ile Thr Val Ala Leu Glu His His His His
          355                 360                 365

His His
    370

<210> SEQ ID NO 115
<211> LENGTH: 388
<212> TYPE: PRT
<213> ORGANISM: Unknown
<220> FEATURE:
<223> OTHER INFORMATION: Sarcotoxin IA-Cpl1

<400> SEQUENCE: 115

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Val Lys Lys Asn Asp Leu
        35                  40                  45

Phe Val Asp Val Ser Ser His Asn Gly Tyr Asp Ile Thr Gly Ile Leu
    50                  55                  60

Glu Gln Met Gly Thr Thr Asn Thr Ile Ile Lys Ile Ser Glu Ser Thr
65                  70                  75                  80

Thr Tyr Leu Asn Pro Cys Leu Ser Ala Gln Val Glu Gln Ser Asn Pro
                85                  90                  95

Ile Gly Phe Tyr His Phe Ala Arg Phe Gly Gly Asp Val Ala Glu Ala
            100                 105                 110

Glu Arg Glu Ala Gln Phe Phe Leu Asp Asn Val Pro Met Gln Val Lys
        115                 120                 125

Tyr Leu Val Leu Asp Tyr Glu Asp Asp Pro Ser Gly Asp Ala Gln Ala
    130                 135                 140

Asn Thr Asn Ala Cys Leu Arg Phe Met Gln Met Ile Ala Asp Ala Gly
145                 150                 155                 160

Tyr Lys Pro Ile Tyr Tyr Ser Tyr Lys Pro Phe Thr His Asp Asn Val
                165                 170                 175

Asp Tyr Gln Gln Ile Leu Ala Gln Phe Pro Asn Ser Leu Trp Ile Ala
            180                 185                 190

Gly Tyr Gly Leu Asn Asp Gly Thr Ala Asn Phe Glu Tyr Phe Pro Ser
        195                 200                 205

Met Asp Gly Ile Arg Trp Trp Gln Tyr Ser Ser Asn Pro Phe Asp Lys
    210                 215                 220

Asn Ile Val Leu Leu Asp Asp Glu Asp Asp Lys Pro Lys Thr Ala
225                 230                 235                 240

Gly Thr Trp Lys Gln Asp Ser Lys Gly Trp Phe Arg Arg Asn Asn
                245                 250                 255

Gly Ser Phe Pro Tyr Asn Lys Trp Glu Lys Ile Gly Gly Val Trp Tyr
            260                 265                 270

Tyr Phe Asp Ser Lys Gly Tyr Cys Leu Thr Ser Glu Trp Leu Lys Asp
        275                 280                 285

Asn Glu Lys Trp Tyr Tyr Leu Lys Asp Asn Gly Ala Met Ala Thr Gly
    290                 295                 300

Trp Val Leu Val Gly Ser Glu Trp Tyr Tyr Met Asp Asp Ser Gly Ala
```

```
                305                 310                 315                 320
Met Val Thr Gly Trp Val Lys Tyr Lys Asn Asn Trp Tyr Tyr Met Thr
                    325                 330                 335
Asn Glu Arg Gly Asn Met Val Ser Asn Glu Phe Ile Lys Ser Gly Lys
                    340                 345                 350
Gly Trp Tyr Phe Met Asn Thr Asn Gly Glu Leu Ala Asp Asn Pro Ser
                    355                 360                 365
Phe Thr Lys Glu Pro Asp Gly Leu Ile Thr Val Ala Leu Glu His His
                    370                 375                 380
His His His His
385

<210> SEQ ID NO 116
<211> LENGTH: 358
<212> TYPE: PRT
<213> ORGANISM: Unknown
<220> FEATURE:
<223> OTHER INFORMATION: PK-Cpl1

<400> SEQUENCE: 116

Met Lys Arg Lys Lys Arg Lys Lys Arg Lys Gly Ser Val Lys Lys Asn
1               5                   10                  15
Asp Leu Phe Val Asp Val Ser Ser His Asn Gly Tyr Asp Ile Thr Gly
                20                  25                  30
Ile Leu Glu Gln Met Gly Thr Thr Asn Thr Ile Ile Lys Ile Ser Glu
                35                  40                  45
Ser Thr Thr Tyr Leu Asn Pro Cys Leu Ser Ala Gln Val Glu Gln Ser
50                  55                  60
Asn Pro Ile Gly Phe Tyr His Phe Ala Arg Phe Gly Gly Asp Val Ala
65                  70                  75                  80
Glu Ala Glu Arg Glu Ala Gln Phe Phe Leu Asp Asn Val Pro Met Gln
                85                  90                  95
Val Lys Tyr Leu Val Leu Asp Tyr Glu Asp Asp Pro Ser Gly Asp Ala
                100                 105                 110
Gln Ala Asn Thr Asn Ala Cys Leu Arg Phe Met Gln Met Ile Ala Asp
                115                 120                 125
Ala Gly Tyr Lys Pro Ile Tyr Tyr Ser Tyr Lys Pro Phe Thr His Asp
130                 135                 140
Asn Val Asp Tyr Gln Gln Ile Leu Ala Gln Phe Pro Asn Ser Leu Trp
145                 150                 155                 160
Ile Ala Gly Tyr Gly Leu Asn Asp Gly Thr Ala Asn Phe Glu Tyr Phe
                165                 170                 175
Pro Ser Met Asp Gly Ile Arg Trp Trp Gln Tyr Ser Ser Asn Pro Phe
                180                 185                 190
Asp Lys Asn Ile Val Leu Leu Asp Asp Glu Asp Asp Lys Pro Lys
                195                 200                 205
Thr Ala Gly Thr Trp Lys Gln Asp Ser Lys Gly Trp Trp Phe Arg Arg
                210                 215                 220
Asn Asn Gly Ser Phe Pro Tyr Asn Lys Trp Glu Lys Ile Gly Gly Val
225                 230                 235                 240
Trp Tyr Tyr Phe Asp Ser Lys Gly Tyr Cys Leu Thr Ser Glu Trp Leu
                245                 250                 255
Lys Asp Asn Glu Lys Trp Tyr Tyr Leu Lys Asp Asn Gly Ala Met Ala
                260                 265                 270
Thr Gly Trp Val Leu Val Gly Ser Glu Trp Tyr Tyr Met Asp Asp Ser
```

```
            275                 280                 285
Gly Ala Met Val Thr Gly Trp Val Lys Tyr Lys Asn Asn Trp Tyr Tyr
290                 295                 300
Met Thr Asn Glu Arg Gly Asn Met Val Ser Asn Glu Phe Ile Lys Ser
305                 310                 315                 320
Gly Lys Gly Trp Tyr Phe Met Asn Thr Asn Gly Glu Leu Ala Asp Asn
                325                 330                 335
Pro Ser Phe Thr Lys Glu Pro Asp Gly Leu Ile Thr Val Ala Leu Glu
            340                 345                 350
His His His His His His
            355

<210> SEQ ID NO 117
<211> LENGTH: 356
<212> TYPE: PRT
<213> ORGANISM: Unknown
<220> FEATURE:
<223> OTHER INFORMATION: Synthetic peptide-Ply511

<400> SEQUENCE: 117

Met Phe Phe Val Ala Pro Gly Ser Val Lys Tyr Thr Val Glu Asn Lys
1               5                   10                  15
Ile Ile Ala Gly Leu Pro Lys Gly Lys Leu Lys Gly Ala Asn Phe Val
            20                  25                  30
Ile Ala His Glu Thr Ala Asn Ser Lys Ser Thr Ile Asp Asn Glu Val
        35                  40                  45
Ser Tyr Met Thr Arg Asn Trp Lys Asn Ala Phe Val Thr His Phe Val
50                  55                  60
Gly Gly Gly Gly Arg Val Val Gln Val Ala Asn Val Asn Tyr Val Ser
65                  70                  75                  80
Trp Gly Ala Gly Gln Tyr Ala Asn Ser Tyr Ser Tyr Ala Gln Val Glu
                85                  90                  95
Leu Cys Arg Thr Ser Asn Ala Thr Thr Phe Lys Lys Asp Tyr Glu Val
            100                 105                 110
Tyr Cys Gln Leu Leu Val Asp Leu Ala Lys Lys Ala Gly Ile Pro Ile
        115                 120                 125
Thr Leu Asp Ser Gly Ser Lys Thr Ser Asp Lys Gly Ile Lys Ser His
130                 135                 140
Lys Trp Val Ala Asp Lys Leu Gly Gly Thr Thr His Gln Asp Pro Tyr
145                 150                 155                 160
Ala Tyr Leu Ser Ser Trp Gly Ile Ser Lys Ala Gln Phe Ala Ser Asp
                165                 170                 175
Leu Ala Lys Val Ser Gly Gly Asn Thr Gly Thr Ala Pro Ala Lys
            180                 185                 190
Pro Ser Thr Pro Ala Pro Lys Pro Ser Thr Pro Ser Thr Asn Leu Asp
        195                 200                 205
Lys Leu Gly Leu Val Asp Tyr Met Asn Ala Lys Met Asp Ser Ser
210                 215                 220
Tyr Ser Asn Arg Asp Lys Leu Ala Lys Gln Tyr Gly Ile Ala Asn Tyr
225                 230                 235                 240
Ser Gly Thr Ala Ser Gln Asn Thr Thr Leu Leu Ser Lys Ile Lys Gly
                245                 250                 255
Gly Ala Pro Lys Pro Ser Thr Pro Ala Pro Lys Pro Ser Thr Ser Thr
            260                 265                 270
Ala Lys Lys Ile Tyr Phe Pro Pro Asn Lys Gly Asn Trp Ser Val Tyr
```

```
                    275                 280                 285
Pro Thr Asn Lys Ala Pro Val Lys Ala Asn Ala Ile Gly Ala Ile Asn
    290                 295                 300

Pro Thr Lys Phe Gly Gly Leu Thr Tyr Thr Ile Gln Lys Asp Arg Gly
305                 310                 315                 320

Asn Gly Val Tyr Glu Ile Gln Thr Asp Gln Phe Gly Arg Val Gln Val
                325                 330                 335

Tyr Gly Ala Pro Ser Thr Gly Ala Val Ile Lys Lys Leu Glu His His
            340                 345                 350

His His His His
            355

<210> SEQ ID NO 118
<211> LENGTH: 514
<212> TYPE: PRT
<213> ORGANISM: Unknown
<220> FEATURE:
<223> OTHER INFORMATION: PK-LysK

<400> SEQUENCE: 118

Met Lys Arg Lys Lys Arg Lys Lys Arg Lys Gly Ser Ala Lys Thr Gln
1               5                   10                  15

Ala Glu Ile Asn Lys Arg Leu Asp Ala Tyr Ala Lys Gly Thr Val Asp
                20                  25                  30

Ser Pro Tyr Arg Val Lys Lys Ala Thr Ser Tyr Asp Pro Ser Phe Gly
            35                  40                  45

Val Met Glu Ala Gly Ala Ile Asp Ala Asp Gly Tyr Tyr His Ala Gln
    50                  55                  60

Cys Gln Asp Leu Ile Thr Asp Tyr Val Leu Trp Leu Thr Asp Asn Lys
65                  70                  75                  80

Val Arg Thr Trp Gly Asn Ala Lys Asp Gln Ile Lys Gln Ser Tyr Gly
                85                  90                  95

Thr Gly Phe Lys Ile His Glu Asn Lys Pro Ser Thr Val Pro Lys Lys
            100                 105                 110

Gly Trp Ile Ala Val Phe Thr Ser Gly Ser Tyr Glu Gln Trp Gly His
        115                 120                 125

Ile Gly Ile Val Tyr Asp Gly Gly Asn Thr Ser Thr Phe Thr Ile Leu
    130                 135                 140

Glu Gln Asn Trp Asn Gly Tyr Ala Asn Lys Lys Pro Thr Lys Arg Val
145                 150                 155                 160

Asp Asn Tyr Tyr Gly Leu Thr His Phe Ile Glu Ile Pro Val Lys Ala
                165                 170                 175

Gly Thr Thr Val Lys Lys Glu Thr Ala Lys Lys Ser Ala Ser Lys Thr
            180                 185                 190

Pro Ala Pro Lys Lys Lys Ala Thr Leu Lys Val Ser Lys Asn His Ile
        195                 200                 205

Asn Tyr Thr Met Asp Lys Arg Gly Lys Lys Pro Glu Gly Met Val Ile
    210                 215                 220

His Asn Asp Ala Gly Arg Ser Ser Gly Gln Gln Tyr Glu Asn Ser Leu
225                 230                 235                 240

Ala Asn Ala Gly Tyr Ala Arg Tyr Ala Asn Gly Ile Ala His Tyr Tyr
                245                 250                 255

Gly Ser Glu Gly Tyr Val Trp Glu Ala Ile Asp Ala Lys Asn Gln Ile
            260                 265                 270

Ala Trp His Thr Gly Asp Gly Thr Gly Ala Asn Ser Gly Asn Phe Arg
```

```
                275                 280                 285
Phe Ala Gly Ile Glu Val Cys Gln Ser Met Ser Ala Ser Asp Ala Gln
290                 295                 300
Phe Leu Lys Asn Glu Gln Ala Val Phe Gln Phe Thr Ala Glu Lys Phe
305                 310                 315                 320
Lys Glu Trp Gly Leu Thr Pro Asn Arg Lys Thr Val Arg Leu His Met
                325                 330                 335
Glu Phe Val Pro Thr Ala Cys Pro His Arg Ser Met Val Leu His Thr
                340                 345                 350
Gly Phe Asn Pro Val Thr Gln Gly Arg Pro Ser Gln Ala Ile Met Asn
                355                 360                 365
Lys Leu Lys Asp Tyr Phe Ile Lys Gln Ile Lys Asn Tyr Met Asp Lys
370                 375                 380
Gly Thr Ser Ser Thr Val Val Lys Asp Gly Lys Thr Ser Ser Ala
385                 390                 395                 400
Ser Thr Pro Ala Thr Arg Pro Val Thr Gly Ser Trp Lys Lys Asn Gln
                405                 410                 415
Tyr Gly Thr Trp Tyr Lys Pro Glu Asn Ala Thr Phe Val Asn Gly Asn
                420                 425                 430
Gln Pro Ile Val Thr Arg Ile Gly Ser Pro Phe Leu Asn Ala Pro Val
                435                 440                 445
Gly Gly Asn Leu Pro Ala Gly Ala Thr Ile Val Tyr Asp Glu Val Cys
450                 455                 460
Ile Gln Ala Gly His Ile Trp Ile Gly Tyr Asn Ala Tyr Asn Gly Asn
465                 470                 475                 480
Arg Val Tyr Cys Pro Val Arg Thr Cys Gln Gly Val Pro Pro Asn Gln
                485                 490                 495
Ile Pro Gly Val Ala Trp Gly Val Phe Lys Leu Glu His His His
                500                 505                 510
His His

<210> SEQ ID NO 119
<211> LENGTH: 272
<212> TYPE: PRT
<213> ORGANISM: Unknown
<220> FEATURE:
<223> OTHER INFORMATION: PK-Lss

<400> SEQUENCE: 119

Ala Met Gly Lys Arg Lys Lys Arg Lys Lys Gly Ser Ala His
1               5                   10                  15
Glu His Ser Ala Gln Trp Leu Asn Asn Tyr Lys Lys Gly Tyr Gly Tyr
                20                  25                  30
Gly Pro Tyr Pro Leu Gly Ile Asn Gly Gly Met His Tyr Gly Val Asp
                35                  40                  45
Phe Phe Met Asn Ile Gly Thr Pro Val Lys Ala Ile Ser Ser Gly Lys
                50                  55                  60
Ile Val Glu Ala Gly Trp Ser Asn Tyr Gly Gly Asn Gln Ile Gly
65                  70                  75                  80
Leu Ile Glu Asn Asp Gly Val His Arg Gln Trp Tyr Met His Leu Ser
                85                  90                  95
Lys Tyr Asn Val Lys Val Gly Asp Tyr Val Lys Ala Gly Gln Ile Ile
                100                 105                 110
Gly Trp Ser Gly Ser Thr Gly Tyr Ser Thr Ala Pro His Leu His Phe
                115                 120                 125
```

-continued

Gln Arg Met Val Asn Ser Phe Ser Asn Ser Thr Ala Gln Asp Pro Met
        130                 135                 140

Pro Phe Leu Lys Ser Ala Gly Tyr Gly Lys Ala Gly Gly Thr Val Thr
145                 150                 155                 160

Pro Thr Pro Asn Thr Gly Trp Lys Thr Asn Lys Tyr Gly Thr Leu Tyr
                165                 170                 175

Lys Ser Glu Ser Ala Ser Phe Thr Pro Asn Thr Asp Ile Ile Thr Arg
            180                 185                 190

Thr Thr Gly Pro Phe Arg Ser Met Pro Gln Ser Gly Val Leu Lys Ala
        195                 200                 205

Gly Gln Thr Ile His Tyr Asp Glu Val Met Lys Gln Asp Gly His Val
    210                 215                 220

Trp Val Gly Tyr Thr Gly Asn Ser Gly Gln Arg Ile Tyr Leu Pro Val
225                 230                 235                 240

Arg Thr Trp Asn Lys Ser Thr Asn Thr Leu Gly Val Leu Trp Gly Thr
                245                 250                 255

Ile Lys Leu Val Pro Arg Gly Ser Leu Glu His His His His His His
            260                 265                 270

<210> SEQ ID NO 120
<211> LENGTH: 281
<212> TYPE: PRT
<213> ORGANISM: Unknown
<220> FEATURE:
<223> OTHER INFORMATION: PK2-Lss

<400> SEQUENCE: 120

Ala Met Gly Lys Arg Lys Lys Arg Lys Lys Arg Lys Lys Arg Lys Lys
1               5                   10                  15

Arg Lys Lys Arg Lys Gly Ser Ala His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Trp
                165                 170                 175

Lys Thr Asn Lys Tyr Gly Thr Leu Tyr Lys Ser Glu Ser Ala Ser Phe
            180                 185                 190

Thr Pro Asn Thr Asp Ile Ile Thr Arg Thr Thr Gly Pro Phe Arg Ser
        195                 200                 205

Met Pro Gln Ser Gly Val Leu Lys Ala Gly Gln Thr Ile His Tyr Asp
    210                 215                 220

```
Glu Val Met Lys Gln Asp Gly His Val Trp Val Gly Tyr Thr Gly Asn
225                 230                 235                 240

Ser Gly Gln Arg Ile Tyr Leu Pro Val Arg Thr Trp Asn Lys Ser Thr
                245                 250                 255

Asn Thr Leu Gly Val Leu Trp Gly Thr Ile Lys Leu Val Pro Arg Gly
            260                 265                 270

Ser Leu Glu His His His His His
        275                 280

<210> SEQ ID NO 121
<211> LENGTH: 525
<212> TYPE: PRT
<213> ORGANISM: Unknown
<220> FEATURE:
<223> OTHER INFORMATION: LysK-PK (PK C-terminal)

<400> SEQUENCE: 121

Met Gly Ser Ser His His His His His His Ser Ser Gly Leu Val Pro
1               5                   10                  15

Arg Gly Ser His Met Ala Lys Thr Gln Ala Glu Ile Asn Lys Arg Leu
            20                  25                  30

Asp Ala Tyr Ala Lys Gly Thr Val Asp Ser Pro Tyr Arg Val Lys Lys
        35                  40                  45

Ala Thr Ser Tyr Asp Pro Ser Phe Gly Val Met Glu Ala Gly Ala Ile
    50                  55                  60

Asp Ala Asp Gly Tyr Tyr His Ala Gln Cys Gln Asp Leu Ile Thr Asp
65                  70                  75                  80

Tyr Val Leu Trp Leu Thr Asp Asn Lys Val Arg Thr Trp Gly Asn Ala
                85                  90                  95

Lys Asp Gln Ile Lys Gln Ser Tyr Gly Thr Gly Phe Lys Ile His Glu
            100                 105                 110

Asn Lys Pro Ser Thr Val Pro Lys Lys Gly Trp Ile Ala Val Phe Thr
        115                 120                 125

Ser Gly Ser Tyr Glu Gln Trp Gly His Ile Gly Ile Val Tyr Asp Gly
130                 135                 140

Gly Asn Thr Ser Thr Phe Thr Ile Leu Glu Gln Asn Trp Asn Gly Tyr
145                 150                 155                 160

Ala Asn Lys Lys Pro Thr Lys Arg Val Asp Asn Tyr Tyr Gly Leu Thr
                165                 170                 175

His Phe Ile Glu Ile Pro Val Lys Ala Gly Thr Thr Val Lys Lys Glu
            180                 185                 190

Thr Ala Lys Lys Ser Ala Ser Lys Thr Pro Ala Pro Lys Lys Lys Ala
        195                 200                 205

Thr Leu Lys Val Ser Lys Asn His Ile Asn Tyr Thr Met Asp Lys Arg
210                 215                 220

Gly Lys Lys Pro Glu Gly Met Val Ile His Asn Asp Ala Gly Arg Ser
225                 230                 235                 240

Ser Gly Gln Gln Tyr Glu Asn Ser Leu Ala Asn Ala Gly Tyr Ala Arg
                245                 250                 255

Tyr Ala Asn Gly Ile Ala His Tyr Tyr Gly Ser Glu Gly Tyr Val Trp
            260                 265                 270

Glu Ala Ile Asp Ala Lys Asn Gln Ile Ala Trp His Thr Gly Asp Gly
        275                 280                 285

Thr Gly Ala Asn Ser Gly Asn Phe Arg Phe Ala Gly Ile Glu Val Cys
290                 295                 300
```

```
Gln Ser Met Ser Ala Ser Asp Ala Gln Phe Leu Lys Asn Glu Gln Ala
305                 310                 315                 320

Val Phe Gln Phe Thr Ala Glu Lys Phe Lys Glu Trp Gly Leu Thr Pro
            325                 330                 335

Asn Arg Lys Thr Val Arg Leu His Met Glu Phe Val Pro Thr Ala Cys
            340                 345                 350

Pro His Arg Ser Met Val Leu His Thr Gly Phe Asn Pro Val Thr Gln
            355                 360                 365

Gly Arg Pro Ser Gln Ala Ile Met Asn Lys Leu Lys Asp Tyr Phe Ile
            370                 375                 380

Lys Gln Ile Lys Asn Tyr Met Asp Lys Gly Thr Ser Ser Ser Thr Val
385                 390                 395                 400

Val Lys Asp Gly Lys Thr Ser Ser Ala Ser Thr Pro Ala Thr Arg Pro
                405                 410                 415

Val Thr Gly Ser Trp Lys Lys Asn Gln Tyr Gly Thr Trp Tyr Lys Pro
            420                 425                 430

Glu Asn Ala Thr Phe Val Asn Gly Asn Gln Pro Ile Val Thr Arg Ile
            435                 440                 445

Gly Ser Pro Phe Leu Asn Ala Pro Val Gly Gly Asn Leu Pro Ala Gly
450                 455                 460

Ala Thr Ile Val Tyr Asp Glu Val Cys Ile Gln Ala Gly His Ile Trp
465                 470                 475                 480

Ile Gly Tyr Asn Ala Tyr Asn Gly Asn Arg Val Tyr Cys Pro Val Arg
                485                 490                 495

Thr Cys Gln Gly Val Pro Pro Asn Gln Ile Pro Gly Val Ala Trp Gly
            500                 505                 510

Val Phe Lys Ser Lys Arg Lys Lys Arg Lys Lys Arg Lys
            515                 520                 525

<210> SEQ ID NO 122
<211> LENGTH: 274
<212> TYPE: PRT
<213> ORGANISM: Unknown
<220> FEATURE:
<223> OTHER INFORMATION: Lss-PK (PK C-terminal)

<400> SEQUENCE: 122

Met Gly Ser Ser His His His His His His Ser Ser Gly Leu Val Pro
1               5                   10                  15

Arg Gly Ser His Met His Glu His Ser Ala Gln Trp Leu Asn Asn Tyr
            20                  25                  30

Lys Lys Gly Tyr Gly Tyr Gly Pro Tyr Pro Leu Gly Ile Asn Gly Gly
            35                  40                  45

Met His Tyr Gly Val Asp Phe Phe Met Asn Ile Gly Thr Pro Val Lys
        50                  55                  60

Ala Ile Ser Ser Gly Lys Ile Val Glu Ala Gly Trp Ser Asn Tyr Gly
65                  70                  75                  80

Gly Gly Asn Gln Ile Gly Leu Ile Glu Asn Asp Gly Val His Arg Gln
                85                  90                  95

Trp Tyr Met His Leu Ser Lys Tyr Asn Val Lys Val Gly Asp Tyr Val
            100                 105                 110

Lys Ala Gly Gln Ile Ile Gly Trp Ser Gly Ser Thr Gly Tyr Ser Thr
            115                 120                 125

Ala Pro His Leu His Phe Gln Arg Met Val Asn Ser Phe Ser Asn Ser
        130                 135                 140
```

-continued

```
Thr Ala Gln Asp Pro Met Pro Phe Leu Lys Ser Ala Gly Tyr Gly Lys
145                 150                 155                 160

Ala Gly Gly Thr Val Thr Pro Thr Pro Asn Thr Gly Trp Lys Thr Asn
                165                 170                 175

Lys Tyr Gly Thr Leu Tyr Lys Ser Glu Ser Ala Ser Phe Thr Pro Asn
            180                 185                 190

Thr Asp Ile Ile Thr Arg Thr Thr Gly Pro Phe Arg Ser Met Pro Gln
        195                 200                 205

Ser Gly Val Leu Lys Ala Gly Gln Thr Ile His Tyr Asp Glu Val Met
    210                 215                 220

Lys Gln Asp Gly His Val Trp Val Gly Tyr Thr Gly Asn Ser Gly Gln
225                 230                 235                 240

Arg Ile Tyr Leu Pro Val Arg Thr Trp Asn Lys Ser Thr Asn Thr Leu
                245                 250                 255

Gly Val Leu Trp Gly Thr Ile Lys Ser Lys Arg Lys Lys Arg Lys Lys
            260                 265                 270

Arg Lys

<210> SEQ ID NO 123
<211> LENGTH: 858
<212> TYPE: DNA
<213> ORGANISM: unknown
<220> FEATURE:
<223> OTHER INFORMATION: PA6gp20

<400> SEQUENCE: 123
atggtacgct acatcccagc agcgcatcac tctgcaggct ctaacaaccc ggtgaaccgt      60
gtagtgatcc acgcgacctg tccggatgta ggcttcccgt ctgcttcccg taaaggtcgt     120
gcggtttcca ctgcgaacta cttcgcgtct ccgtcctctg gcggttctgc acactacgtg     180
tgcgatatcg gtgagaccgt gcagtgcctg tccgaaagca ctattggttg gcacgctccg     240
ccgaacccac atagcctggg tatcgaaatc tgtgctgacg tggctcccca cgcttctttc     300
cgtgtcccag gtcacgctta cactcgcgaa cagtggctgg atccacaggt ttggccagcc     360
gtagaacgtg ctgcagttct gtgtcgtcgc ctgtgcgaca aatataacgt cccgaaacgc     420
aaactgtctg cagcggacct gaaagcaggt cgtcgtggtg tttgcggtca cgttgacgta     480
accgacgcct ggcaccagtc tgatcacgac gatccgggtc cgtggtttcc gtgggacaaa     540
ttcatggcag tggttaacgg tggcagcggt gattctggcg aactgaccgt tgccgacgtc     600
aaagcgctgc acgaccagat taaacagctc tctgctcagc tgaccggtag cgtgaacaaa     660
ctgcaccatg acgtaggcgt tgtccaggtt cagaacggtg atctgggcaa acgcgttgat     720
gctctgagct gggtgaaaaa cccggtgacg gtaaactgt ggcgtaccaa agatgcgctg     780
tggtccgttt ggtactatgt tctggaatgc cgtagccgtc tggaccgtct ggaatctgcc     840
gtgaacgacc tgaaaaaa                                                   858

<210> SEQ ID NO 124
<211> LENGTH: 314
<212> TYPE: PRT
<213> ORGANISM: unknown
<220> FEATURE:
<223> OTHER INFORMATION: Walmagh1-PA6gp20

<400> SEQUENCE: 124

Met Gly Phe Phe Ile Pro Ala Val Ile Leu Pro Ser Ile Ala Phe Leu
1               5                   10                  15
```

```
Ile Val Pro Gly Ser Val Arg Tyr Ile Pro Ala Ala His His Ser Ala
             20              25              30

Gly Ser Asn Asn Pro Val Asn Arg Val Val Ile His Ala Thr Cys Pro
             35              40              45

Asp Val Gly Phe Pro Ser Ala Ser Arg Lys Gly Arg Ala Val Ser Thr
     50              55              60

Ala Asn Tyr Phe Ala Ser Pro Ser Ser Gly Gly Ser Ala His Tyr Val
65              70              75              80

Cys Asp Ile Gly Glu Thr Val Gln Cys Leu Ser Glu Ser Thr Ile Gly
             85              90              95

Trp His Ala Pro Pro Asn Pro His Ser Leu Gly Ile Glu Ile Cys Ala
             100             105             110

Asp Gly Gly Ser His Ala Ser Phe Arg Val Pro Gly His Ala Tyr Thr
             115             120             125

Arg Glu Gln Trp Leu Asp Pro Gln Val Trp Pro Ala Val Glu Arg Ala
     130             135             140

Ala Val Leu Cys Arg Arg Leu Cys Asp Lys Tyr Asn Val Pro Lys Arg
145             150             155             160

Lys Leu Ser Ala Ala Asp Leu Lys Ala Gly Arg Arg Gly Val Cys Gly
             165             170             175

His Val Asp Val Thr Asp Ala Trp His Gln Ser Asp His Asp Asp Pro
             180             185             190

Gly Pro Trp Phe Pro Trp Asp Lys Phe Met Ala Val Val Asn Gly Gly
             195             200             205

Ser Gly Asp Ser Gly Glu Leu Thr Val Ala Asp Val Lys Ala Leu His
     210             215             220

Asp Gln Ile Lys Gln Leu Ser Ala Gln Leu Thr Gly Ser Val Asn Lys
225             230             235             240

Leu His His Asp Val Gly Val Val Gln Val Gln Asn Gly Asp Leu Gly
             245             250             255

Lys Arg Val Asp Ala Leu Ser Trp Val Lys Asn Pro Val Thr Gly Lys
             260             265             270

Leu Trp Arg Thr Lys Asp Ala Leu Trp Ser Val Trp Tyr Tyr Val Leu
     275             280             285

Glu Cys Arg Ser Arg Leu Asp Arg Leu Glu Ser Ala Val Asn Asp Leu
     290             295             300

Lys Lys Leu Glu His His His His His His
305             310
```

ANTIMICROBIAL FUSION PROTEINS COMPRISING AN ENDOLYSIN AND AN AMPHIPATHIC PEPTIDE SEGMENT

This application is a continuation of U.S. application Ser. No. 13/380,329, filed Dec. 22, 2011, as a national phase application under 35 U.S.C. § 371 of International Application No. PCT/EP2010/059152 filed 28 Jun. 2010, which claims priority to European Application No. 09 163 955.9 filed on 26 Jun. 2009. The entire text of each of the above-referenced disclosures is specifically incorporated herein by reference without disclaimer.

REFERENCE TO AN ELECTRONIC SEQUENCE LISTING

The contents of the electronic sequence listing, named "DEBEP0111USC1_ST25.txt", which is 207 KB (as measured in Microsoft Windows®) and was created on Jan. 28, 2019, is herein incorporated by reference in its entirety.

The present invention relates to antimicrobial agents against Gram-positive bacteria, in particular to fusion proteins composed of an enzyme having the activity of degrading the cell wall of Gram-positive bacteria and an additional peptide stretch fused to the enzyme at the N- or C-terminus. Moreover, the present invention relates to nucleic acid molecules encoding said fusion protein, vectors comprising said nucleic acid molecules and host cells comprising either said nucleic acid molecules or said vectors. In addition, the present invention relates to said fusion protein for use as a medicament, in particular for the treatment or prevention of Gram-positive bacterial infections, as diagnostic means or as cosmetic substance. The present invention also relates to the treatment or prevention of Gram-positive bacterial contamination of foodstuff, of food processing equipment, of food processing plants, of surfaces coming into contact with foodstuff, of medical devices, of surfaces in hospitals and surgeries. Further, the present invention relates to a pharmaceutical composition comprising said fusion protein.

In contrast to Gram-negative bacteria, Gram-positive bacteria do not possess an outer membrane. The cytoplasmic membrane is surrounded by an up to 25 nm thick layer of peptidoglycan (which is only up to 5 nm for Gram-negative bacteria) which forms the cell wall. Main purpose of the cell wall of Gram-positives is to maintain bacterial shape and to counteract the internal bacterial cell pressure. Peptidoglycan, or murein, is a polymer consisting of sugars and amino acids. The sugar component consists of alternating residues of β-(1,4) linked N-acetylglucosamine and N-acetylmuramic acid residues compose the sugar components. A peptide chain of three to five amino acids is attached to the N-acetylmuramic acid. The peptide chain can be cross-linked to the peptide chain of another strand forming a 3D mesh-like layer. The peptide chain may contain D- and L-amino acid residues and the composition may vary for different bacteria.

A special situation is found in case of Mycobacteria which are usually considered Gram-positive. Mycobacteria were recently shown to posses an outer cell membrane. All Mycobacteria share a characteristic thick cell wall, which is hydrophobic, waxy, and rich in mycolic acids/mycolates. The cell wall consists of the hydrophobic mycolate layer and a peptidoglycan layer held together by arabinogalactan, a polysaccharide. To overcome the thick cell wall of Mycobacteria a combined action of the new antimicrobial agents with a chitinase or a similar protein to disrupt the polysaccharide layer may be necessary.

Various types of agents having bactericidal or bacteriostatic activity are known, e.g. antibiotics, endolysins, antimicrobial peptides and defensins. Increasing microbial resistance to antibiotics, however, is creating difficulties in treating more and more infections caused by bacteria. Particular difficulties arise with infections caused by Gram-positive bacteria like *Staphylococcus aureus*, Enterococci, Streptococci, *Listeria monocytogenes* and *Clostridium difficile*, especially with e.g. Methicillin-resistant *Staphylococcus aureus* and Vancomycin-resistant Enterococci.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram-positive bacteria. Subsequently different endolysins against other Gram-positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. However, it is also known that endolysins can, under some conditions (e.g. high ionic strength), create stable protoplast, where the internal bacterial cell pressure is not sufficient to lead to a cell burst. Under these conditions the bacterial cell wall can regenerate and the bacteria will survive.

Antimicrobial peptides (AMPs) represent a wide range of short, cationic or amphipatic gene-encoded peptide antibiotics that can be found in virtually every organism. Different AMPs display different properties, and many peptides in this class are being intensively researched not only as antibiotics, but also as templates for cell-penetrating peptides. Despite sharing a few common features (e.g., cationicity, amphipathicity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs is typically in the low micromolar range, scepticism has understandably arisen regarding the relevance of these thresholds and their importance in vivo (Melo et al., Nature reviews, Microbiology, 2009, 245).

Defensins are a large family of small, cationic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and nonenveloped viruses. However, the concentrations needed for efficient killing of bacteria are mostly high, i.e. in the µ-molar range. Activity of many peptides may be limited in presence of physiological salt conditions, divalent cations and serum. Depending on the content of hydrophobic amino acid residues Defensins also show haemolytic activity.

Thus, there is a need for new antimicrobial agents against Gram-positive bacteria.

This object is solved by the subject matter defined in the claims.

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the polypeptide chains, such as heme or lipid, giving rise to the conjugated proteins which are also comprised by the term "protein" as used herein. The various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta. Moreover, the term "protein" refers to a complex, wherein the complex refers to a homomer.

The term "fusion protein" as used herein refers to an expression product resulting from the fusion of two nucleic acid sequences. Such a protein may be produced, e.g., in recombinant DNA expression systems. Moreover, the term "fusion protein" as used herein refers to a fusion of a first amino acid sequence as e.g. an enzyme, with a second or further amino acid sequence. The second or further amino acid sequence may define a domain or any kind of peptide stretch. Preferably, said second and/or further amino acid sequence is foreign to and not substantially homologous with any domain of the first amino acid sequence.

The term "peptide stretch" as used herein refers to any kind of peptide linked to a protein such as an enzyme.

The term "peptide" as used herein refers to short polypeptides consisting of from about 2 to about 100 amino acid residues, more preferably from about 4 to about 50 amino acid residues, more preferably to about 5 to 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Examples of naturally occurring peptides are antimicrobial peptides, defensins, sushi peptides. Examples of synthetically produced peptides are polycationic, amphiphatic or hydrophobic peptides. A peptide in the meaning of the present invention does not refer to His-tags, Strep-tags, thioredoxin or maltose binding proteins (MBP) or the like, which are used to purify or locate proteins.

The term "endolysin" as used herein refers to an enzyme which is suitable to hydrolyse bacterial cell walls. "Endolysins" comprise of at least one "enzymatically active domain" (EAD) having at least one of the following activities: endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase, N-acetyl-glucosaminidase (lysozyme) or transglycosylases as e.g. KZ144 and EL188. In addition, the endolysins may contain also regions which are enzymatically inactive, and bind to the cell wall of the host bacteria, the so-called CBDs (cell wall binding domains).

The term "CBD" as used herein refers to the cell wall binding domain of an endolysin. In endolysins being specific for Gram-positive bacteria the CBD is often found at the C-terminus, but may also be found N-terminal or somewhere else within the protein. Often CBD domains mediate binding of the endolysin to the bacterial cell wall but have no enzymatic activity in terms of hydrolyzing the cell wall.

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module.

The term "autolysins" refers to enzymes related to endolysins but encoded by bacteria and involved in e.g. cell division. An overview of autolysins is can be found in "Bacterial peptidoglycan (murein) hydrolases. Vollmer W, Joris B, Charlier P, Foster S. FEMS Microbiol Rev. 2008 March; 32(2):259-86".

The term "bacteriocin" as used herein refers to protein-like, polypeptide-like or peptide-like substances which are able to inhibit the growth of other bacteria. Some bacteriocins are capable of degrading bacterial cell walls like Lysostaphin (degrading *Staphylococcus* cell walls), Mutanolysin (degrading *Streptococcus* cell walls) and Enterolysin (degrading *Enterococcus* cell walls). Preferably said inhibition is specifically by means of absorption of said other bacteria to specific receptors of the bacteriocin. In general, bacteriocins are produced by microorganisms. However, the term "bacteriocin" as used herein refers both to an isolated form procuded by a microorganism or to a synthetically produced form, and refers also to variants which substantially retain the activities of their parent bacteriocins, but whose sequences have been altered by insertion or deletion of one or more amino acid residues.

The term, "antimicrobial peptide" (AMP) as used herein refers to any peptide that has microbicidal and/or microbistatic activity. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties.

The term "defensin" as used herein refers to a peptide present within animals, preferably mammals, more preferably humans, wherein the defensin plays a role in the innate host defense system as the destruction of foreign substances such as infectious bacteria and/or infectious viruses and/or fungi. A defensin is non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. Examples of naturally occurring cationic peptides which can be recombinantly produced are defensins, magainins, melittin, and cecropins.

The term "polycationic peptide" as used herein refers to a synthetically produced peptide composed of mostly lysine and/or arginine residues.

The term "amphipathic peptide" as used herein refers to peptides having both hydrophilic and hydrophobic functional groups. Preferably, the term "amphipathic peptide" as used herein refers to a peptide having a defined arrangement of hydrophilic and hydrophobic groups e.g. amphipatic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acids having a hydrophobic side chain interact with one another to generate a nonaqueous environment. Examples of amino acids with hydrophobic side chains are alanine, valine, leucine, isoleucine, phenylalanine, histidine, tryptophane and tyrosine.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The present invention relates to new antibacterial agents against Gram-positive bacteria, in particular to fusion proteins composed of an enzyme having the activity of degrading the cell wall of Gram-positive bacteria and an additional peptide stretch fused to the enzyme at the N- or C-terminus or at both termini.

The fusion proteins according to the present invention have the advantage that they may prevent the regeneration of stable protoplasts and thus, preventing the survival of the bacteria which should be eliminated. The regeneration of the protoplast by the bacteria occurs under some conditions (e.g. high ionic strength), where the internal bacterial cell pressure is not sufficient to lead to a cell burst and leads to the survival of the bacteria.

In one aspect of the present invention the enzyme having the activity of degrading the cell wall of Gram-positive bacteria is an endolysine, autolysine and/or bacteriocin.

In another aspect of the present invention the enzyme may contain also regions which are enzymatically inactive, and bind to the cell wall of the host bacteria, the so-called CBDs (cell wall binding domains).

Preferred fusion proteins according to the present invention are depicted in SEQ ID NO:63 to 90. The fusion proteins according to SEQ ID NO:63 to 90 may comprise one or more additional amio acid residues on the N-terminus. Preferably the additional amino acid residue is methionine.

Preferably, the endolysin is encoded by bacteriophages specific for Gram-positive bacteria such as Gram-positive bacteria of bacterial groups, families, genera or species comprising strains pathogenic for humans or animals as listed in the following table.

TABLE 1

I. Phylum Actinobacteria
    Class: Actinobacteridae
        Order Actinomycetales
            Families:
            Actinomycineae: Actinomycetaceae (*Actinomyces, Mobiluncus*)
            Corynebacterineae: Mycobacteriaceae (*Mycobacterium*), Nocardiaceae,
            Corynebacteriaceae
            Frankineae: Frankiaceae
            Micrococcineae: Brevibacteriaceae
            Propionibacteriaceae (*Propionibacterium*)
        Order: Bifidobacteriales
            Families:
            Bifidobacteriaceae (*Bifidobacterium, Falcivibrio, Gardnerella*)
        Other subclasses: Acidimicrobidae, Coriobacteridae, Rubrobacteridae, Sphaerobacteridae
II. Phylum Firmicutes
    Class: Bacilli
        Order: Bacillales:
            Families:

TABLE 1-continued

Bacillaceae (*Bacillus*), Listeriaceae (*Listeria*), Staphylococcaceae
(*Staphylococcus, Gemella, Jeotgalicoccus*)
Order: Lactobacillales:
    Families: Enterococcaceae (*Enterococcus*), Lactobacillaceae
    (*Lactobacillus, Pediococcus*), Leuconostocaceae (*Leuconostoc*),
    Streptococcaceae (*Lactococcus, Streptococcus*)
Class: Clostridia
    Order: Clostridiales (*Clostridium, Peptostreptococcus, Selenomonas*)
    Order: Halanaerobiales
    Order: Thermoanaerobacterales
Class: Tenericutes/Mollicutes
    Order: Mycoplasmatales (*Mycoplasma, Ureaplasma*)
    Order: Entomoplasmatales (*Spiroplasma*)
    Order: Anaeroplasmatales (*Erysipelothrix*)
    Order: Acholeplasmatales (*Acholeplasma*)
Order: Haloplasmatales (*Haloplasma*)

Preferably, the autolysin is encoded by Gram-positive bacteria such as Gram-positive bacteria of bacterial groups, families, genera or species comprising strains pathogenic for humans or animals as listed in table 1.

Preferably, the bacteriocin is encoded by Gram-positive bacteria such as Gram-positive bacteria of bacterial groups, families, genera or species comprising strains pathogenic for humans or animals as listed in table 1.

The enzyme according to the present invention has cell wall degrading activity against Gram-positive bacteria of bacterial groups, families, genera or species comprising strains pathogenic for humans or animals like *Listeria monocytogenes, Staphylococcus aureus, Enterococcus faecalis, Enterococcus faecium, Streptococcus pneumoniae, Streptococcus pyogenes, Streptococcus mutans, Streptococcus equi, Clostridium difficile, Clostridium botulinum, Clostridium tetani, Clostridium perfringens, Bacillus anthracis, Bacillus cereus, Propionibacterium acnes, Mycobacterium avium, Mycobacterium tuberculosis, Corynebacterium diphteriae, Mycoplasma pneumoniae, Actinomyces*.

Preferred endolysins are *Listeria* phage endolysins PlyA118, PlyA500, PlyPSA, PlyA511, PlyP35, PlyP40, Staph phage Phi 11, Phi MR11, LysK, *Clostridium perfringens* PlyS6, Ply3626, *Clostridium difficile*: CD27L endolysin, *Streptococcus*: B30 endolysin, phage Dp-1 Pal amidase, Cl endolysin, Cpl-1 endolysin, PlyGBS, Enterococccus: PlyV12, *Bacillus anthracis*: Phage gamma endolysin PlyG.

Preferred autolysins are described in: Bacterial peptidoglycan (murein) hydrolases. Vollmer W, Joris B, Charlier P, Foster S. FEMS Microbiol Rev. 2008 March; 32(2):259-86. Epub 2008 February 11. Review. An example of a preferred autolysin is the AtlA Autolysine.

Preferred bacteriocines are Lysostaphin (degrading *Staphylococcus* cell walls), Mutanolysin (degrading *Streptococcus* cell walls) and Enterolysin (degrading *Enterococcus* cell walls).

More preferably, the endolysin part is selected from the group consisting of Cpl-1 according to SEQ ID NO:57, Ply511 according to SEQ ID NO:58, LysK according to SEQ ID NO:59, Lysostaphin according to SEQ ID NO:60 and PA6-gp20 according to SEQ ID NO:61.

In another preferred embodiment of the present invention the endolysins, autolysins and bacteriocins of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Said endolysins, autolysins and bacteriocins of the fusion protein according to the present invention exhibit the lytic activity of the respective wild-type endolysin. However, said activity can be the same, higher or lower as the activity of the respective wild-type endolysin. Said activity can be about 10, 20, 30, 40, 50, 60, 70, 80, 90, 100, 110, 120, 130, 140, 150, 160, 170, 180, 190 or about 200% of the activity of the respective wild-type endolysin or even more. The activity can be measured by assays well known in the art by a person skilled in the art as e.g. the plate lysis assay or the liquid lysis assay which are e.g. described in Briers et al., *J. Biochem. Biophys Methods* 70: 531-533, (2007) or Donovan D M, Lardeo M, Foster-Frey J. *FEMS Microbiol Lett.* 2006 Dec.; 265(1) or similar publications.

Preferably, the peptide stretch of the fusion protein according to the invention is fused to the N-terminus and/or to the C-terminus of the endolysin. In a particular preferred embodiment said peptide stretch is only fused to the N-terminus of the enzyme. In another preferred embodiment the peptide stretch is only fused to the C-Terminus of the enzyme. However, also preferred are modified fusion proteins having a peptide stretch both on the N-terminus and on the C-terminus. Said peptide stretches on the N-terminus and on the C-terminus can be the same or distinct peptide stretches. The peptide stretch can be linked to the enzyme by additional amino acid residues e.g. due to cloning reasons. Preferably, said peptide stretch can be linked to the fusion protein by at least 1, 2, 3, 4, 5, 6, 7, 8, 9 or 10 additional amino acid residues. In a preferred embodiment the peptide stretch is linked to the enzyme by the additional amino acid residues glycine and/or serine (Gly-Ser). Moreover, the peptide stretch of the fusion protein according to the invention further comprises additional amino acids on its N-terminus. Preferably, the peptide stretch comprises the amino acid methionine (Met) or alanine, methionine and glycine (Ala-Met-Gly).

The peptide stretch of the fusion protein according to the present invention is preferably covalently bound to the enzyme. Preferably, said peptide stretch consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide stretch comprising about 5 to about 100 amino acid residues, about 5 to about 50 or about 5 to about 30 amino acid residues. More preferred is a peptide stretch comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

Preferably, the peptide stretch is no tag such as a His$_6$-tag, Strep-tag, Avi-tag, Myc-tag, Gst-tag, JS-tag, cystein-tag, FLAG-tag or other tags known in the art and no thioredoxin or maltose binding proteins (MBP). However, the peptide stretch and/or the endolysin, autolysin or bacteriocin according to the present invention may comprise in addition such tag or tags.

More preferably the peptide stretch has the function to facilitate the burst of the bacterial cell via interaction of the fusion protein with: first the peptidoglycan layer, degrading the peptidoglycan and second the cytoplasmic membrane, destabilizing the cytoplasmic membrane.

In one aspect of the present invention the fused peptide stretch is a cationic peptide, more preferably a polycationic peptide. Preferably the cationic peptide comprises one or more of the positively charged amino acid residues of lysine, arginine and/or histidine. Preferably, more than about 60, 65, 70, 75, 80, 85, 90, 95 or about 100%, of the amino acid residues in said peptide are positively charged amino acid residues. Advantageously, the cationic peptide is fused at the N-terminal and/or the C-terminal end of the enzyme having cell wall degrading activity, thus enhancing the cationicity of the fusion proteins and/or antimicrobial agents of the present invention. In another embodiment of the invention, the cationic peptide fused to the enzyme consists of at least 5, more preferably of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. Preferably at least about 60, 65, 70, 75, 80, 85, 90, 95 or about 100%, of the amino acid residues of the cationic peptide are either arginine or lysine. In another embodiment of the present invention the cationic peptide comprises about 3 to about 50, more preferably about 5 to about 20, for instance about 5 to about 15 amino acid residues and the said amino acid residues are either arginine or lysine residues. Preferred cationic peptides are depicted in SEQ ID NOs:13 and 14.

Especially preferred are cationic and/or polycationic peptide stretches comprising at least one motive according to SEQ ID NO: 62 (KRKKRK). In particular cationic peptide stretches comprising at least 2, 3, 4, 5, 6, 7, 8, 9, 10, 11, 12, 13, 14, 15, 16 or 17 motives according to SEQ ID NO: 62 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic peptide stretch comprises beside the positively charged amino acid residues, in particular lysine and/or arginine residues, neutrally charged amino acid residues, in particular glycine and/or serine residues. Preferred are cationic peptide stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are polypeptide stretches consisting of about 4% to about 8% serine residues, of about 33% to about 36% arginine residues and of about 56% to about 63% lysine residues. Especially preferred are polypeptide stretches comprising at least one motive according to SEQ ID NO: 45 (KRXKR), wherein X is any other amino acid than lysine, arginine and histidine. Especially preferred are polypeptide stretches comprising at least one motive according to SEQ ID NO: 46 (KRSKR). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 45 (KRXKR) or SEQ ID NO: 46 (KRSKR).

Also preferred are polypeptide stretches consisting of about 9 to about 16% glycine residues, of about 4 to about 11% serine residues, of about 26 to about 32% arginine residues and of about 47 to about 55% lysine residues. Especially preferred are polypeptide stretches comprising at least one motive according to SEQ ID NO: 47 (KRGSG). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 47 (KRGSG).

In another preferred embodiment of the present invention the cationic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues.

Especially preferred are peptide stretches selected from the group consisting of the following sequences:

TABLE 2

| peptide stretch | length | SEQ ID NO: |
|---|---|---|
| KRKKRK | 6 | SEQ ID NO: 24 |
| KRKKRKKRK | 9 | SEQ ID NO: 13 |
| RRRRRRRRR | 9 | SEQ ID NO: 25 |

TABLE 2-continued

| peptide stretch | length | SEQ ID NO: |
|---|---|---|
| KKKKKKKK | 8 | SEQ ID NO: 26 |
| KRKKRKKRKK | 10 | SEQ ID NO: 27 |
| KRKKRKKRKKRK | 12 | SEQ ID NO: 28 |
| KRKKRKKRKKRKKR | 14 | SEQ ID NO: 29 |
| KKKKKKKKKKKKKKKK | 16 | SEQ ID NO: 30 |
| KRKKRKKRKKRKKRKKRK | 18 | SEQ ID NO: 31 |
| KRKKRKKRKKRKKRKKRKK | 19 | SEQ ID NO: 32 |
| RRRRRRRRRRRRRRRRRRR | 19 | SEQ ID NO: 33 |
| KKKKKKKKKKKKKKKKKKK | 19 | SEQ ID NO: 34 |
| KRKKRKKRKRSKRKKRKKRK | 20 | SEQ ID NO: 35 |
| KRKKRKKRKRSKRKKRKKRKK | 21 | SEQ ID NO: 36 |
| KRKKRKKRKRKKRKKRKKRK | 21 | SEQ ID NO: 37 |
| KRKKRKKRKRGSGKRKKRKKRK | 22 | SEQ ID NO: 38 |
| KRKKRKKRKRGSGSGKRKKRKKRK | 24 | SEQ ID NO: 39 |
| KRKKRKKRKRKKRKKRKKRKKRKK | 25 | SEQ ID NO: 40 |
| KRKKRKKRKRSKRKKRKKRKRSKRKKRKKRK | 31 | SEQ ID NO: 41 |
| KRKKRKKRKRGSGSGKRKKRKKRKGSGSGKRKKRKKRK | 38 | SEQ ID NO: 42 |
| KRKKRKKRKRKRKKRKKRKKRKKRKKRKKRKKRKKRKKRK | 39 | SEQ ID NO: 43 |
| KRKKRKKRKRSKRKKRKKRKRSKRKKRKKRKRSKRKKRKKRK | 42 | SEQ ID NO: 44 |

In a further aspect of the present invention the fused peptide stretch is an amphipatic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, histidine, threonin, serine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphipathic peptide is fused at the N-terminal and/or the C-terminal end of the enzyme having cell wall degrading activity, thus enhancing the amphipathicity of the latter proteins.

In another embodiment of the invention, the amphipathic peptide fused to the enzyme consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues. In a preferred embodiment at least about 30, 40, 50, 60 or 70% of the said amino acid residues of the amphipatic peptide are either arginine or lysine residues and/or at least about 30, 40, 50, 60 or 70% of the said amino acid residues of the amphipathic peptide are of the hydrophobic amino acids valine, isoleucine, leucine, methionine, phenylalanine, tryptophan, cysteine, alanine, tyrosine, histidine, threonin, serine, proline and/or glycine.

Preferred amphipatic peptides are Pleurocidin according to SEQ ID NO:1, Cecropin P1 according to SEQ ID NO:2, Buforin II according to SEQ ID NO:3, Buforin I according to SEQ ID NO:23 and Magainin according to SEQ ID NO:4. Further preferred amphipatic peptides are Cathelidicine e.g. LL-37 according to SEQ ID NO:5, Nigrocine 2 according to SEQ ID NO: 48 and Ascaphine 5 according to SEQ ID NO:49.

In a further aspect of the present invention the fused peptide stretch is an antimicrobial peptide, which comprises a positive net charge and around 50% hydrophobic amino acids. The antimicrobial peptides are amphipathic, with a length of about 12 to about 50 amino acid residues.

Examples for antimicrobial peptides are listed in the following table.

TABLE 3

| Peptid | Sequenz | |
|---|---|---|
| LL-37 | LLGDFFRKSKEKIGKEFKRIVQRIKDFLRNLVPRTES | SEQ ID NO: 5 |
| SMAP-29 | RGLRRLGRKIAHGVKKYGPTVLRIIRIAG | SEQ ID NO: 6 |

TABLE 3-continued

| Peptid | Sequenz | |
|---|---|---|
| Indolicidin | ILPWKWPWWPWRR | SEQ ID NO: 7 |
| Protegrin | RGGRLCYCRRRFCVCVGR | SEQ ID NO: 8 |
| Cecropin P1 | SWLSKTAKKLENSAKKRISEGIAIAIQGGPR | SEQ ID NO: 2 |
| Magainin | GIGKFLHSAKKFGKAFVGEIMNS | SEQ ID NO: 4 |
| Pleurocidin | GWGSFFKKAAHVGKHVGKAALTHYL | SEQ ID NO: 1 |
| Cecropin A (*A. aegypti*) | GGLKKLGKKLEGAGKRVFNAAEKALPVVAGAKALRK | SEQ ID NO: 9 |
| Cecropin A (*D. melanogaster*) | GWLKKIGKKIERVGQHTRDATIQGLGIPQQAANVAATARG | SEQ ID NO: 10 |
| Buforin II | TRSSRAGLQFPVGRVHRLLRK | SEQ ID NO: 3 |
| Sarcotoxin IA | GWLKKIGKKIERVGQHTRDATIQGLGIAQQAANVAATAR | SEQ ID NO: 11 |
| Apidaecine | ANRPVYIPPPRPPHPRL | SEQ ID NO: 50 |
| Ascaphine 5 | GIKDWIKGAAKKLIKTVASHIANQ | SEQ ID NO: 49 |
| Nigrocine 2 | GLLSKVLGVGKKVLCGVSGLVC | SEQ ID NO: 48 |
| Pseudin 1 | GLNTLKKVFQGLHEAIKLINNHVQ | SEQ ID NO: 51 |
| Ranalexin | FLGGLIVPAMICAVTKKC | SEQ ID NO: 52 |
| Melittin | GIGAVLKVLTTGLPALISWIKRKRQQ | SEQ ID NO: 53 |

In a further aspect of the present invention the fused peptide stretch is a sushi peptide which is described by Ding J L, Li P, Ho B Cell Mol Life Sci. 2008 April; 65(7-8): 1202-19. The Sushi peptides: structural characterization and mode of action against Gram-negative bacteria. Especially preferred is the sushi 1 peptide according to SEQ ID NO:54.

Preferred sushi peptides are sushi peptides 51 and S3 and multiples thereof; FASEB J. 2000 Sep.; 14(12):1801-13.

In a further aspect of the present invention the fused peptide stretch is a defensin, preferably Cathelicidine, Cecropin P1, Cecropin A or Magainin II.

In a further aspect of the present invention the fused peptide stretch is a hydrophobic peptide e.g. Apidaecine having the amino acid sequence according to SEQ ID NO: 50, WLBU2-Variant having the amino acid sequence according to SEQ ID NO: 55 and Walmaghl having the amino acid sequence according to SEQ ID NO: 56. The hydrophobic peptide having the amino acid sequence Phe-Phe-Val-Ala-Pro (SEQ ID NO: 12) is not part of the present invention.

In another preferred embodiment of the present invention the peptide stretches of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, peglyation, chemical changes of the amino-, SH- or carboxyl-groups.

Especially preferred are fusion proteins according to the SEQ ID NOs: 63 to 90 and the fusion proteins selected from the group consisting of the following fusion proteins:

TABLE 4

| Fusion protein | Fusion protein | Enzyme part | Peptide stretch (N-terminal unless otherwise indicated) |
|---|---|---|---|
| P1-E1 | SEQ ID NO: 63 | Cpl-1 (SEQ ID NO: 57) | Ascaphine 5 (SEQ ID NO: 49) |
| P2-E1 | SEQ ID NO: 64 | Cpl-1 (SEQ ID NO: 57) | Apiadaecine (SEQ ID NO: 50) |
| P3-E1 | SEQ ID NO: 65 | Cpl-1 (SEQ ID NO: 57) | Nigrocine 2 (SEQ ID NO: 48) |
| P4-E1 | SEQ ID NO: 66 | Cpl-1 (SEQ ID NO: 57) | Pseudin 1 (SEQ ID NO: 51) |
| P7-E1 | SEQ ID NO: 67 | Cpl-1 (SEQ ID NO: 57) | Ranalexin (SEQ ID NO: 52) |
| P8-E1 | SEQ ID NO: 68 | Cpl-1 (SEQ ID NO: 57) | WLBU2-Variant (SEQ ID NO: 55) |
| P9-E1 | SEQ ID NO: 69 | Cpl-1 (SEQ ID NO: 57) | Sushi 1 (SEQ ID NO: 54) |
| P10-E1 | SEQ ID NO: 70 | Cpl-1 (SEQ ID NO: 57) | Melittin (SEQ ID NO: 53) |
| P11-E1 | SEQ ID NO: 71 | Cpl-1 (SEQ ID NO: 57) | LL-37 (SEQ ID NO: 5) |
| P12-E1 | SEQ ID NO: 72 | Cpl-1 (SEQ ID NO: 57) | Indolicidin (SEQ ID NO: 7) |
| P13-E1 | SEQ ID NO: 73 | Cpl-1 (SEQ ID NO: 57) | SMAP-29 (SEQ ID NO: 6) |
| P14-E1 | SEQ ID NO: 74 | Cpl-1 (SEQ ID NO: 57) | Protegrin (SEQ ID NO: 8) |
| P15-E1 | SEQ ID NO: 75 | Cpl-1 (SEQ ID NO: 57) | Cecropin P1 (SEQ ID NO: 2) |
| P16-E1 | SEQ ID NO: 76 | Cpl-1 (SEQ ID NO: 57) | Magainin (SEQ ID NO: 4) |
| P17-E1 | SEQ ID NO: 77 | Cpl-1 (SEQ ID NO: 57) | Pleurocidin (SEQ ID NO: 1) |
| P18-E1 | SEQ ID NO: 78 | Cpl-1 (SEQ ID NO: 57) | Cecropin A (*A. aegypti*) (SEQ ID NO: 9) |
| P19-E1 | SEQ ID NO: 79 | Cpl-1 (SEQ ID NO: 57) | Cecropin A (*D. melanogaster*) (SEQ ID NO: 10) |

TABLE 4-continued

| Fusion protein | Fusion protein | Enzyme part | Peptide stretch (N-terminal unless otherwise indicated) |
|---|---|---|---|
| P20-E1 | SEQ ID NO: 80 | Cpl-1 (SEQ ID NO: 57) | Buforin II (SEQ ID NO: 3) |
| P21-E1 | SEQ ID NO: 81 | Cpl-1 (SEQ ID NO: 57) | Sarcotoxin IA (SEQ ID NO: 11) |
| P5-E1 | SEQ ID NO: 82 | Cpl-1 (SEQ ID NO: 57) | PK (SEQ ID NO: 13) |
| P22-E2 | SEQ ID NO: 83 | Ply511 (SEQ ID NO: 58) | Pentapeptid (SEQ ID NO: 12) |
| P5-E7 | SEQ ID NO: 84 | LysK (SEQ ID NO: 59) | PK (N-terminal) (SEQ ID NO: 13) |
| P6-E7 | SEQ ID NO: 85 | LysK (SEQ ID NO: 59) | PK2 (SEQ ID NO: 31) |
| P5-E8 | SEQ ID NO: 86 | Lysostaphin (SEQ ID NO: 60) | PK (C-terminal) (SEQ ID NO: 13) |
| P6-E8 | SEQ ID NO: 87 | Lysostaphin (SEQ ID NO: 60) | PK2 (SEQ ID NO: 31) |
| P23-E9 | SEQ ID NO: 88 | PA6-gp20 (SEQ ID NO: 61) | Walmagh1 (SEQ ID NO: 56) |
| P5-E7 | SEQ ID NO: 89 | LysK (SEQ ID NO: 59) | PK (C-terminal) (SEQ ID NO: 13) |
| P5-E8 | SEQ ID NO: 90 | Lysostaphin (SEQ ID NO: 60) | PK (N-terminal) (SEQ ID NO: 13) |

The fusion protein according to the present invention, and thus in particular the especially preferred fusion proteins according to SEQ ID NO:63 to 90, may additional comprise a methionine on the N-terminus.

The fusion protein according to the present invention, and thus in particular the especially preferred fusion proteins according to SEQ ID NO:63 to 90, may additional comprise a tag e.g. for purification. Preferred is a His$_6$-tag, preferably at the C-terminus of the fusion protein. Said tag can be linked to the fusion protein by additional amino acid residues e.g. due to cloning reasons. Preferably said tag can be linked to the fusion protein by at least 1, 2, 3, 4, 5, 6, 7, 8, 9 or 10 additional amino acid residues. In a preferred embodiment the fusion protein comprises a His$_6$-tag at its C-terminus linked to the fusion protein by the additional amino acid residues lysine and glycine (Lys-Gly) or leucine and glutamic acid (Leu-Glu). In another preferred embodiment the fusion protein comprises a His$_6$-tag at its N-terminus linked to the fusion protein by the additional amino acid residues lysine and glycine (Lys-Gly) or leucine and glutamic acid (Leu-Glu). In a more preferred embodiment the fusion protein comprises a His$_6$-tag at its N-terminus linked to the fusion protein by the additional amino acid residues leucine and glutamic acid (Leu-Glu). In another preferred embodiment the fusion protein comprises a His$_6$-tag at its C-terminus linked to the fusion protein by the additional amino acid residues leucine and glutamic acid (Leu-Glu).

In a more preferred embodiment the fusion protein comprises a His$_6$-tag at its C-terminus linked to the fusion protein by the additional amino acid residues leucine and glutamic acid (Leu-Glu) and the peptide stretch of the fusion protein according to the invention is linked to the N-terminus of the enzyme by the additional amino acid residues glycine and serine (Gly-Ser). In another preferred embodiment the fusion protein comprises a His$_6$-tag at its C-terminus linked to the fusion protein by the additional amino acid residues leucine and glutamic acid (Leu-Glu) and the peptide stretch of the fusion protein according to the invention is linked to the N-terminus of the enzyme by the additional amino acid residues glycine and serine (Gly-Ser) and the fusion protein comprises on the N-terminus the additional amino acid residues methionine (Met) or methionine and glycine (Met-Gly) or alanine, methionine and glycine (Ala-Met-Gly). Preferably the fusion proteins are according to SEQ ID NO: 108 to 123.

In another preferred embodiment the fusion protein comprises a His$_6$-tag at its N-terminus, wherein the His$_6$-tag further comprises on its N-terminus the additional amino acids serine and serine (Ser-Ser) or methionine and glycine (Met-Gly) or methionine, glycine, serine and serine (Met-Gly-Ser-Ser; SEQ ID NO: 125).

In another preferred embodiment the fusion protein comprises a His$_6$-tag at its N-terminus linked to the fusion protein by the additional amino acid residues serine, serine, glycine, leucine, valine, proline, arginine, glycine, serine and histidine (Ser-Ser-Gly-Leu-Val-Pro-Arg-Gly-Ser-His; SEQ ID NO: 126). In another preferred embodiment the fusion protein comprises a His$_6$-tag at its N-terminus linked to the fusion protein by the additional amino acid residues serine, serine, glycine, leucine, valine, proline, arginine, glycine, serine, histidine and methionine (Ser-Ser-Gly-Leu-Val-Pro-Arg-Gly-Ser-His-Met; SEQ ID NO: 127). In another preferred embodiment the fusion protein comprises a His$_6$-tag at its N-terminus linked to the fusion protein by the additional amino acid residues serine, serine, glycine, leucine, valine, proline, arginine, glycine, serine and histidine (Ser-Ser-Gly-Leu-Val-Pro-Arg-Gly-Ser-His; SEQ ID NO: 126) or serine, serine, glycine, leucine, valine, proline, arginine, glycine, serine, histidine and methionine (Ser-Ser-Gly-Leu-Val-Pro-Arg-Gly-Ser-His-Met; SEQ ID NO: 127) and the peptide stretch of the fusion protein according to the invention is linked to the C-terminus of the enzyme by the additional amino acid residue serine. In another preferred embodiment the fusion protein comprises a His$_6$-tag at its N-terminus linked to the fusion protein by the additional amino acid residues serine, serine, glycine, leucine, valine, proline, arginine, glycine, serine and histidine (Ser-Ser-Gly-Leu-Val-Pro-Arg-Gly-Ser-His; SEQ ID NO: 126) or serine, serine, glycine, leucine, valine, proline, arginine, glycine, serine, histidine and methionine (Ser-Ser-Gly-Leu-Val-Pro-Arg-Gly-Ser-His-Met; SEQ ID NO: 127) and the peptide stretch of the fusion protein according to the invention is linked to the C-terminus of the enzyme by the additional amino acid residue serine and the His$_6$-tag comprises on the N-terminus the additional amino acid residues serine and serine (Ser-Ser) or methionine, glycine, serine and serine (Met-Gly-Ser-Ser; SEQ ID NO: 125) or methionine and serine (Met-Ser). Preferably the fusion proteins are according to SEQ ID NO: 122 and 123.

Fusion proteins are constructed by linking at least two nucleic acid sequences using standard cloning techniques as described e.g. by Sambrook et al. 2001, Molecular Cloning: A Laboratory Manual. Such a protein may be produced, e.g., in recombinant DNA expression systems. Such fusion proteins according to the present invention can be obtained by fusing the nucleic acids for endolysin and the respective peptide stretch.

The fusion proteins according to the present invention may be fused or linked to other additional proteins. Example for this other additional protein is thioredoxin.

The present invention further relates to an isolated nucleic acid molecule encoding the fusion protein according to the present invention. The present invention further relates to a vector comprising the nucleic acid molecule according to the present invention. Said vector may provide for the constitutive or inducible expression of said fusion protein according to the present invention.

The invention also relates to a method for obtaining said fusion proteins from a micro-organism, such as a genetically modified suitable host cell which expresses said fusion proteins. Said host cell may be a micro-organism such as bacteria or yeast or an animal cell as e.g. a mammalian cell, in particular a human cell. In one embodiment of the present invention the host cell is a *Pichia pastoris* cell. The host may be selected due to mere biotechnological reasons, e.g. yield, solubility, costs, etc. but may be also selected from a medical point of view, e.g. a non-pathological bacteria or yeast, human cells. Another aspect of the present invention is related to a method for genetically transforming a suitable host cell in order to obtain the expression of the fusion proteins according to the invention wherein the host cell is genetically modified by the introduction of a genetic material encoding said fusion proteins into the host cell and obtain their translation and expression by genetic engineering methods well known by the man skilled in the art.

In a further aspect the present invention relates to a composition, preferably a pharmaceutical composition, comprising a fusion protein according to the present invention and/or a host transformed with a nucleic acid molecule or a vector comprising a nucleotide sequence encoding a fusion protein according to the present invention.

The present invention also relates to a fusion protein according to the present invention and/or a host transformed with a nucleic acid comprising a nucleotide sequence encoding a fusion protein according to the present invention for use as a medicament. In a further aspect the present invention relates to the use of a fusion protein according to the present invention and/or a host transformed with a vector comprising a nucleic acid molecule comprising a nucleotide sequence encoding a modified, fusion protein according to the present invention in the manufacture of a medicament for the treatment and/or prevention of a disorder, disease or condition associated with Gram-positive bacteria. In particular the treatment and/or prevention of the disorder, disease or condition may be caused by Gram-positive bacteria of bacterial groups, families, genera or species comprising strains pathogenic for humans or animals like *Listeria monocytogenes, Staphylococcus aureus, Enterococcus faecalis, Enterococcus faecium, Streptococcus pneumoniae, Streptococcus pyogenes, Streptococcus mutans, Streptococcus equi, Clostridium difficile, Clostridium botulinum, Clostridium tetani, Clostridium perfringens, Bacillus anthracis, Bacillus cereus, Propionibacterium acnes, Mycobacterium avium, Mycobacterium tuberculosis, Corynebacterium diphteriae, Mycoplasma pneumoniae, Actinomyces*.

The present invention further relates to a medicament comprising a fusion protein according to the present invention and/or a host transformed with a nucleic acid comprising a nucleotide sequence encoding a fusion protein according to the present invention.

In a further aspect the present invention relates to a method of treating a disorder, disease or condition in a subject in need of treatment and/or prevention, which method comprises administering to said subject an effective amount of a fusion protein according to the present invention and/or an effective amount of a host transformed with a nucleic acid comprising a nucleotide sequence encoding a fusion protein according to the present invention or a composition according to the present invention. The subject may be a human or an animal.

In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-positive bacteria, in particular by the Gram-positive bacteria as listed above.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of a fusion protein according to the present invention and/or an effective amount of a host transformed with a nucleic acid comprising a nucleotide sequence encoding a fusion protein according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, powder, suppository, emulsion, suspension, gel, lotion, cream, salve, injectable solution, syrup, spray, inhalant or any other medical reasonable galenic formulation. Preferably, the galenic formulation may comprise suitable carriers, stabilizers, flavourings, buffers or other suitable reagents. For example, for topical application the formulation may be a lotion, cream, gel, salve or plaster, for nasopharyngeal application the formulation may be saline solution to be applied via a spray to the nose. For oral administration in case of the treatment and/or prevention of a specific infection site e.g. in the intestine, it can be necessary to protect a fusion protein according to the present invention from the harsh digestive environment of the gastrointestinal tract until the site of infection is reached. Thus, bacteria as carrier, which survive the initial steps of digestion in the stomach and which secret later on a fusion protein according to the present invention into the intestinal environment can be used.

In a specific embodiment of the present invention the use of a fusion protein according to the present invention and/or a host transformed with a vector comprising a nucleic acid molecule comprising a nucleotide sequence encoding a fusion protein according to the present invention in the manufacture of a medicament for the treatment and/or prevention of a disorder, disease or condition caused by *Listeria monocytogenes*, in particular Granulomatosis infantiseptica (listeriosis of newborns), mononucleosis, conjunctivitis, meningitis, granulomatosis septica and the listeriosis of pregnant women.

In another specific embodiment of the present invention the disorder, disease or condition is caused by *Staphylococcus aureus*, in particular infections of the skin like pyoderma, particularly folliculitis, furuncle, carbuncle, abscesses of the sweat glands and pemphigus, and like scaled skin syndrome. The scaled skin syndrome can appear in three clinical pictures: dermatitis exfoliativa, impetigo bullosa and scarlatiniform erythroderma. Moreover the disorder, disease or condition caused by *Staphylococcus aureus* is *Staphylococcus* pneumonia, hospitalism, in particular surgical wound infections, mastitis puerperalis and enterokolitis, and food poisonings.

In another specific embodiment of the present invention the disorder, disease or condition is caused by *Streptococcus pyogenes*, in particular tonsillitis, pharyngitis, scarlet, erysipelas, rheumatic fever and acute glomerulonephritis.

In another specific embodiment of the present invention the disorder, disease or condition is caused by *Streptococcus*

*pneumoniae*, in particular pneumonia, ulcus serpens corneae, otitis media, meningitis, peritonitis, mastoiditis and osteomyelitis.

In another specific embodiment of the present invention the disorder, disease or condition is caused by *Clostridium perfringens*, in particular gas gangrene, enteritis necroticans ulcerosa and food poisonings.

In another specific embodiment of the present invention the disorder, disease or condition is caused by *Clostridium botulinum*, in particular botulism.

In another specific embodiment of the present invention the disorder, disease or condition is caused by *Clostridium difficile*, in particular pseudomembranoes enterokolitis.

In another specific embodiment of the present invention the disorder, disease or condition is caused by *Bacillus anthracis*, in particular cutaneous anthrax, inhalation anthrax, and gastrointestinal anthrax.

In another specific embodiment of the present invention the disorder, disease or condition is caused by *Enterococcus faecalis* or *E. faecium*, like nosokomial infections, and endokarditis.

In another specific embodiment of the present invention the disorder, disease or condition is caused by *Bacillus cereus*, in particular food poisonings, bronchial pneumonia, septicaemia and meningitis.

In another specific embodiment of the present invention the disorder, disease or condition is caused by *Mycobacterium avium, Mycobacterium* paratuberculosis and *Mycobacterium tuberculosis*, in particular tuberculosis.

In another specific embodiment of the present invention the disorder, disease or condition is caused by *Mycoplasma pneumoniae*, in particular pneumonia, diseases of the upper respiratory tract and inflammations of the ear drum.

In another specific embodiment of the present invention the disorder, disease or condition is caused by *Actinomyces*, in particular actinomycosis in human, cattle, cat and dog.

In another specific embodiment of the present invention the disorder, disease or condition is caused by *Corynebacterium* diphteriae, in particular localized diphtheria of the tonsils, the nose, the nasopharynx or the middle ear, progressive diphtheria of the larynx, the trachea and the bronchi, toxic or maligne diphtheria, skin and wound diphtheria.

Preferably, a fusion protein according to the present invention is used for medical treatment, if the infection to be treated (or prevented) is caused by multiresistant bacterial strains, in particular by strains resistant against one or more of the following antibiotics: streptomycin, tetracycline, cephalothin, penicillin, gentamicin, cefotaxime, cephalosporin, ceftazidime or imipenem. Furthermore, a fusion protein according to the present invention can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises one or more fusion protein according to the present invention and/or one or more hosts transformed with a nucleic acid comprising a nucleotide sequence encoding a fusion protein according to the present invention or a composition according to the present invention, In another aspect the present invention relates to a process of preparation of a pharmaceutical composition, said process comprising admixing one or more fusion protein according to the present invention and/or one or more hosts transformed with a nucleic acid comprising a nucleotide sequence encoding a fusion protein according to the present invention with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the fusion protein according to the present invention in order to degrade already existing or freshly settling pathogenic Gram-positive bacteria.

In a further aspect the present invention relates to the fusion protein according to the present invention for use as diagnostic means in medicinal, food or feed or environmental diagnostics, in particular as a diagnostic means for the diagnostic of bacteria infection caused in particular by Gram-positive bacteria. In this respect the fusion protein according to the present invention may be used as a tool to specifically degrade pathogenic bacteria, in particular Gram-positive pathogenic bacteria. The degradation of the bacterial cells by the fusion protein according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. $\beta$-galactosidase for enterobacteria, coagulase for coagulase positive strains).

In a further aspect the present invention relates to the use of the fusion protein according to the present invention for the treatment or prevention of Gram-positive bacterial contamination of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a fusion protein of the present invention may be used prophylactically as sanitizing agent. Said sanitizing agent may be used before or after surgery, or for example during hemodialysis. Moreover, premature infants and immunocompromised persons, or those subjects with need for prosthetic devices may be treated with a fusion protein according to the present invention. Said treatment may be either prophylactically or during acute infection. In the same context, nosocomial infections, especially by antibiotic resistant strains like Methicillin-resistant *Staphylococcus aureus*, Vancomycin-resistant *Enterococcus faecalis*, Vancomycin-resistant *Enterococcus faecium, Streptococcus pneumoniae, Propionibacterium acnes*, multidrug-resistant *Mycobacterium tuberculosis*, may be treated prophylactically or during acute phase with a fusion protein of the present invention. Therefore, a fusion protein according to the present invention may be used as a disinfectant also in combination with other ingredients useful in a disinfecting solution like detergents, tensids, solvents, antibiotics, lanthibiotics, or bacteriocins.

For the use of the fusion protein according to the present invention as a disinfectant e.g. in hospital, dental surgery, veterinary, kitchen or bathroom, the fusion protein can be prepared in a composition in form of e.g. a fluid, a powder, a gel, or an ingredient of a wet wipe or a disinfection sheet product. Said composition may additionally comprise suitable carrier, additives, diluting agents and/or excipients for its respective use and form, respectively,—but also agents that support the antimicrobial activity like EDTA or agents enhance the antimicrobial activity of the fusion proteins. The fusion protein may also be used with common disinfectant agents like, Alcohols, Aldehydes, Oxidizing agents, Phenolics, Quaternary ammonium compounds or UV-light. For disinfecting for example surfaces, objects and/or devices the fusion protein can be applied on said surfaces, objects and/or devices. The application may occur for instance by wetting the disinfecting composition with any means such as a cloth or rag, by spraying, pouring. The fusion proteins may be used in varying concentration depending on the respective application and the "reaction time" intended to obtain full antimicrobial activity.

Further scope of applicability of the present invention will become apparent from the detailed description given hereinafter, however, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1: CLONING, EXPRESSION AND PURIFICATION OF CPL-1, PLY511, LYSK, LYSOSTAPHIN (LSS) AND PA6-GP20 ENZYMES MODIFIED WITH VARIOUS PEPTIDE STRETCHES ON THE N-TERMINUS OR THE C-TERMINUS

Enzymes

Cpl-1 according to SEQ ID NO: 57 is an endolysin originating from *Streptococcus pneumoniae* phage Cpl-1. The endolysin Cpl-1 is encoded by the nucleic acid molecule according to SEQ ID NO: 91. The nucleic acid molecule according to SEQ ID NO: 91 was synthetically produced with a BamH I (5'-GGA TCC-3') restriction site at the 5'-end of the nucleic acid molecule and an Xho I (5"-CTC GAG-3') restriction site at the 3'-end of the nucleic acid molecule.

Ply511 according to SEQ ID NO: 58 is an endolysin originating from *Listeria monocytogenes* phage A511. The endolysin Ply511 is encoded by the nucleic acid molecule according to SEQ ID NO: 92. The nucleic acid molecule according to SEQ ID NO: 92 was synthetically produced with a BamH I (5'-GGA TCC-3') restriction site at the 5'-end of the nucleic acid molecule and an Xho I (5"-CTC GAG-3') restriction site at the 3'-end of the nucleic acid molecule.

LysK according to SEQ ID NO: 59 is an endolysin originating from *Staphylococcus aureus* phage K. The endolysin LysK is encoded by the nucleic acid molecule according to SEQ ID NO: 93. The nucleic acid molecule according to SEQ ID NO: 93 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

Lysostaphin (Lss) according to SEQ ID NO: 60 is a bacteriocin originating from *Staphylococcus simulans*. The bacteriocin Lss is encoded by the nucleic acid molecule according to SEQ ID NO: 94. The nucleic acid molecule according to SEQ ID NO: 94 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

PA6-gp20 according to SEQ ID NO: 61 is an endolysin originating from *Propionibacterium acnes* phage. The endolysin PA6-gp20 is encoded by the nucleic acid molecule according to SEQ ID NO: 123. The nucleic acid molecule according to SEQ ID NO: 123 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

The following peptide stretches in table 5 were used for production of fusion proteins with the enzymes Cpl-1, Ply511, LysK, Lysostaphin (Lss) and PA6-gp20:

TABLE 5

| Peptide stretch | Nucleic acid molecule encoding the peptide stretch |
| --- | --- |
| Pseudin 1 (SEQ ID NO: 51) | SEQ ID NO: 95 |
| WLBU2-Variant (SEQ ID NO: 55) | SEQ ID NO: 96 |
| LL-37 (SEQ ID NO: 5) | SEQ ID NO: 97 |
| Indolicidin (SEQ ID NO: 7) | SEQ ID NO: 98 |
| Magainin (SEQ ID NO: 4) | SEQ ID NO: 99 |
| Pleurocidin (SEQ ID NO: 1) | SEQ ID NO: 100 |
| Cecropin A (*A. aegypti*) (SEQ ID NO: 9) | SEQ ID NO: 101 |
| Buforin II (SEQ ID NO: 3) | SEQ ID NO: 102 |
| Sarcotoxin IA (SEQ ID NO: 11) | SEQ ID NO: 103 |
| PK (SEQ ID NO: 13) | SEQ ID NO: 104 |
| Pentapeptide (SEQ ID NO: 12) | SEQ ID NO: 105 |
| PK2 (SEQ ID NO: 31) | SEQ ID NO: 106 |

The nucleic acid molecules encoding the respective peptide stretches were synthetically produced with a Nde I (5'-CAT ATG-3') restriction site at the 5'-end of the nucleic acid molecule and a BamH I (5'-GGA TCC-3') restriction site at the 3'-end of the nucleic acid molecule, except the nucleic acid molecule encoding the PK and PK2 for ligation with the bacteriocin Lss, which was produced with a Nco I restriction site plus two additional nucleotides (5'-CCA TGG GC-3') at the 5'-end of the nucleic acid molecule.

Fusion proteins are constructed by linking at least two nucleic acid sequences using standard cloning techniques as described e.g. by Sambrook et al. 2001, Molecular Cloning: A Laboratory Manual. Therefore the nucleic acid molecules encoding the peptide stretches were cleaved in a digest with the respective restriction enzymes Nde I and BamH I and in case of the nucleic acid molecule encoding the peptide stretch PK and PK2 for ligation with the Lss the digest was performed with the restriction enzymes Nco I and BamH I. Subsequently the cleaved nucleic acids encoding the peptide stretches were ligated into the pET21 b expression vector (Novagen, Darmstadt, Germany), which was also cleaved in a digest with the respective restriction enzymes Nde I and BamH I before. The cleaved nucleic acid molecule encoding the peptide stretch PK and PK2 for ligation with Lss was ligated into a modified pET32 b expression vector (unmodified vector obtainable from Novagen, Darmstadt, Germany), which was also cleaved in a digest with the respective restriction enzymes Nco I and BamH I before. The modification of the pET32b expression vector refers to the deletion of the sequence encoding a S-tag and the central $His_6$-tag.

Afterwards, the nucleic acid molecules encoding the enzymes Cpl-1, Ply511, PA6-gp20, LysK and Lss were cleaved in a digest with the restriction enzyme BamH I and Xho I, so that the endolysin could be ligated into the pET21b expression vector (Novagen, Darmstadt, Germany) and the modified pET32 b expression vector, respectively, which were also cleaved in a digest with the respective restriction enzymes BamH I and Xho I before.

In the case of the peptide stretch PK, which was ligated to the C-terminus of the Lysostaphin and the LysK, the resulting fusion protein has a $His_6$-tag on the N-terminus, wherein the $His_6$-tag is linked to the N-terminus by a linker. For the cloning of the respective nucleic acid molecules the pET32 b expression vector (Novagen, Darmstadt, Germany) was used.

Thus, the nucleic acid molecule encoding the peptide stretch is ligated into the respective vector at the 5'-end of the nucleic acid molecule encoding the respective enzyme. Moreover, the nucleic acid molecule encoding the respective enzyme is ligated into the respective plasmid, so that a nucleic acid molecule encoding a $His_6$-tag consisting of six histidine residues is associated at the 3"-end of the nucleic acid molecule encoding the endolysin.

As some fusion proteins may either be toxic upon expression in bacteria, or not homogenous due to protein degradation, the strategy might be to express these fusion proteins fused or linked to other additional proteins. Example for these other additional protein is thioredoxin, which was shown to mediate expression of toxic antimicrobial peptides in *E. coli* (TrxA mediating fusion expression of antimicrobial peptide CM4 from multiple joined genes in *Escherichia coli*. Zhou L, Zhao Z, Li B, Cai Y, Zhang S. Protein Expr Purif. 2009 April; 64(2):225-230). In the case of the fusion protein consisting of the N-terminal PK or PK2 peptide and the bacteriocin Lss, the peptide was ligated into the modified pET32 b expression vector, so that an additional thioredoxin is associated at the 5'-end of the peptide. The thioredoxin could be removed from the expressed fusion protein by the use of enterokinase, therefore between the nucleic acid molecule encoding the peptide and the one encoding the thioredoxin is an enterokinase restriction site introduced.

The sequence of the endolysin-peptide-fusions was controlled via DNA-sequencing and correct clones were transformed into *E. coli* BL21(DE3) and in *E. coli* BL21 (DE3) pLysS cells (Novagen, Darmstadt, Germany) for protein expression.

Recombinant expression of the fusion proteins according to SEQ ID NO: 107 to 122 and 124 is performed in *E. coli* BL21 (DE3) and *E. coli* BL21 (DE3) pLysS cells (Novagen, Darmstadt, Germany). The cells were growing until an optical density of OD600 nm of 0.5-0.8 was reached. Then the expression of the fusion protein was induced with 1 mM IPTG (isopropylthiogalactoside) and the expression was performed at 37° C. for a period of 4 hours.

*E. coli* BL21 cells were harvested by centrifugation for 20 min at 6000 g and disrupted via sonication on ice. Soluble and insoluble fraction of the *E. coli* crude extract were separated by centrifugation (Sorvall, SS34, 30 min, 15 000 rpm). All proteins were purified by $Ni^{2+}$ affinity chromatography (Akta FPLC, GE Healthcare) using the C-terminal $His_6$-tag, encoded by the pET21b or pET32b vectors.

Some proteins were expressed using a modified pET32b vector (S-tag and central $His_6$-tag deleted) as described above, which fuses thioredoxin on the N-terminus of the proteins of interest. The vector also contains an enterokinase cleavage site right before the protein of interest. This site allows the proteolytic cleavage between thioredoxin and the protein of interest, which can purified via the remaining C-terminal $His_6$-tag. For antimicrobial function of the fusion protein it may be necessary to remove the thioredoxin by proteolytic cleavage. Therefore the fusion protein was cleaved with 2-4 units/mg recombinant enterokinase (Novagen, Darmstadt, Germany) to remove the thioredoxin following the protocol provided by the manufacturer. After enterokinase cleavage the fusion protein was purified via $His_6$-tag purification as described below.

The Ni' affinity chromatography is performed in 4 subsequent steps, all at room temperature:
1. Equilibration of the Histrap FF 5 ml column (GE Healthcare) with up to 10 column volumes of Washing Buffer (20 mM imidazole, 1 M NaCl and 20 mM Hepes on pH 7.4) at a flow rate of 3-5 ml/min.
2. Loading of the total lysate (with wanted fusion protein) on the Histrap FF 5 ml column at a flow rate of 3-5 ml/min.
3. Washing of the column with up to 10 column volumes of Washing Buffer to remove unbound sample followed by a second washing step with 10% Elution buffer (500 mM imidazole, 0.5 M NaCl and 20 mM Hepes on pH 7.4) at a flow rate of 3-5 ml/min.
4. Elution of bounded fusion proteins from the column with a linear gradient of 4 column volumes of Elution Buffer (500 mM imidazole, 0.5 M NaCl and 20 mM Hepes on pH 7.4) to 100% at a flow rate of 3-5 ml/min.

Purified stock solutions of fusion proteins in Elution Buffer (20 mM Hepes pH 7.4; 0.5 M NaCl; 500 mM imidazole) were at least 90% pure as determined visually on SDS-PAGE gels (data not shown).

EXAMPLE 2: ANTIMICROBIAL ACTIVITY OF CPL-1 ENZYMES MODIFIED WITH VARIOUS PEPTIDE STRETCHES ON THE N-TERMINUS

The fusion proteins Cpl 1 with the N-terminal peptide stretches Pseudin 1, WLBU2-Variant, LL-37, Indolicidin, Magainin, Pleurocidin, Cecropin A (*A. aegypti*), Buforin II, Sarcotoxin IA and PK were produced as described in example 1. The antimicrobial activity of said fusion protein against *Streptococcus pneumoniae* DSMZ 11967 and *Streptococcus pneumoniae* DSMZ 14378 were tested by using the plating test described below. The measured activity of the fusion protein is shown in Table 6.

The results presented in Table 6 show high antimicrobial activity of all fusion proteins against *Streptococcus pneumoniae* DSMZ 11967 and *Streptococcus pneumoniae* DSMZ 14378.

Plating Assay:

Exponentially growing cells of e.g. Streptococci, *Listeria*, Propionibacteria or Staphylococci were taken (1 ml) cooled on ice and washed with distilled water. The bacteria were resuspended in 20 mM Tris pH 7.0, 1 mM $MgCl_2$, 0.5 M Saccharose. Fusion proteins were diluted in resuspension buffer, adding sucrose to a final concentration of 0.5 M and incubated (final concentration of the fusion protein about 10 μg/ml) with the respective bacteria for 60 minutes at room temperature. After that bacteria were plated on appropriated agar plates (e.g. Streptococci: Columbia blood agar) containing 0.5 M sucrose and the resulting colonies were counted after incubation.

The residual colonies were counted after an overnight incubation at 37° C. Based on the counted cell numbers the antibacterial activity as logarithmic units (=$\log_{10} N_0/N_i$ with $N_0$=number of untreated cells and $N_i$=number of treated cells) was calculated. All samples were replicated at least in four fold.

TABLE 6

| Fusion protein | Enzyme part | Peptide stretch (N-terminal unless otherwise indicated) | Activity against *Streptococcus pneumoniae* DSMZ 11967 | Activity against *Streptococcus pneumoniae* DSMZ 14378 |
|---|---|---|---|---|
| SEQ ID NO: 107 | Cpl-1 (SEQ ID NO: 57) | Pseudin 1 (SEQ ID NO: 51) | +++ | +++ |
| SEQ ID NO: 108 | Cpl-1 (SEQ ID NO: 57) | WLBU2-Variant (SEQ ID NO: 55) | ++ | ++ |
| SEQ ID NO: 109 | Cpl-1 (SEQ ID NO: 57) | LL-37 (SEQ ID NO: 5) | +++ | +++ |
| SEQ ID NO: 110 | Cpl-1 (SEQ ID NO: 57) | Indolicidin (SEQ ID NO: 7) | +++ | +++ |
| SEQ ID NO: 111 | Cpl-1 (SEQ ID NO: 57) | Magainin (SEQ ID NO: 4) | +++ | +++ |
| SEQ ID NO: 112 | Cpl-1 (SEQ ID NO: 57) | Pleurocidin (SEQ ID NO: 1) | +++ | +++ |
| SEQ ID NO: 113 | Cpl-1 (SEQ ID NO: 57) | Cecropin A (*A. aegypti*) (SEQ ID NO: 9) | +++ | +++ |
| SEQ ID NO: 114 | Cpl-1 (SEQ ID NO: 57) | Buforin II (SEQ ID NO: 3) | +++ | +++ |
| SEQ ID NO: 115 | Cpl-1 (SEQ ID NO: 57) | Sarcotoxin IA (SEQ ID NO: 11) | +++ | +++ |
| SEQ ID NO: 116 | Cpl-1 (SEQ ID NO: 57) | PK (SEQ ID NO: 13) | +++ | +++ |

Abbreviations:
+: 1 log;
++: 2-3 log;
+++: 4 or more logs.

EXAMPLE 3: ANTIMICROBIAL ACTIVITY OF PLY511 ENZYME MODIFIED WITH THE PENTAPEPTIDE ON THE N-TERMINUS

The fusion protein Ply511 with the N-terminal peptide stretch pentapeptide according to SEQ ID NO: 12 was produced as described in example 1. The antimicrobial activity of said fusion protein against *Listeria monocytogenes* DSMZ 15675 and *Listeria monocytogenes* DSMZ 20600 was tested by using the plating test described in example 2. The measured activity of the fusion protein is shown in Table 7.

The results presented in Table 7 show high antimicrobial activity of the fusion protein pentapeptide: Ply511 against *Listeria monocytogenes* DSMZ 15675 and *Listeria monocytogenes* DSMZ 20600.

TABLE 7

| Fusion protein | Enzyme part | Peptide stretch (N-terminal unless otherwise indicated) | Activity against *Listeria monocytogenes* DSMZ 15675 | Activity against *Listeria monocytogenes* DSMZ 20600 |
|---|---|---|---|---|
| SEQ ID NO: 117 | Ply511 (SEQ ID NO: 58) | Pentapeptid (SEQ ID NO: 12) | +++ | +++ |

Abbreviations:
+: 1 log;
++: 2-3 log;
+++: 4 or more logs.

EXAMPLE 4: ANTIMICROBIAL ACTIVITY OF LSS AND LYSK ENZYME MODIFIED WITH POLYCATIONIC PEPTIDES ON THE N-TERMINUS OR C-TERMINUS

The fusion proteins Lss and LysK, respectively, with the N-terminal peptide stretch PK according to SEQ ID NO: 13, the fusion protein Lss with the N-terminal peptide stretch PK2 according to SEQ ID NO:31, as well as the fusion proteins Lss and LysK, respectively, with the C-terminal peptide stretch PK were produced as described in example 1. The antimicrobial activity of said fusion proteins against *Staphylococcus aureus* DSMZ 346 and *Staphylococcus epidermidis* DSMZ 20041 was tested by using the plating test described in example 2, as well as by using the lysis test as described in the following.

Lysis Test

The Lysis test was used for the modified LysK and Lysostaphins to examine the antimicrobial effect of these fusion proteins.

Staphylococcal cells of were grown in BHI medium until and optical density at 600 nm of 0.7-1 was reached indicating exponential growth. Cells were harvested by centrifugation and resuspended in lysis buffer (20 mM Tris-HCl (pH 7.4), 60 mM NaCl, 2 mM CaCl2. Cells were resuspended at an optical density at 600 nm of 1.0 and incubated with fusion proteins. Activity was measured spectrophotometrically at 600 nm.

The measured activity of the fusion protein is shown in Table 8.

The results presented in Table 8 show high antimicrobial activity of the fusion proteins Lss with the N-terminal peptide PK or PK2 against *Staphylococcus aureus* DSMZ 346 andStaphylococcus *epidermidis* DSMZ 20041. But also the other fusion proteins show antimicrobial activity against the two tested bacterial strains.

TABLE 8

| Fusion protein | Enzyme part | Peptide stretch (N-terminal unless otherwise indicated) | Activity against *Staphylococcus aureus* DSMZ 346 | Activity against *Staphylococcus epidermidis* DSMZ 20041 |
|---|---|---|---|---|
| SEQ ID NO: 118 | LysK (SEQ ID NO: 59) | PK (SEQ ID NO: 13) | + | + |
| SEQ ID NO: 119 | Lysostaphin (SEQ ID NO: 60) | PK (SEQ ID NO: 13) | +++ | +++ |
| SEQ ID NO: 120 | Lysostaphin (SEQ ID NO: 60) | PK2 (SEQ ID NO: 31) | +++ | +++ |
| SEQ ID NO: 121 | LysK (SEQ ID NO: 59) | PK (C-terminal) (SEQ ID NO: 13) | + | + |
| SEQ ID NO: 122 | Lysostaphin (SEQ ID NO: 60) | PK (C-terminal) (SEQ ID NO: 13) | + | + |

Abbreviations:
+: 1 log;
++: 2-3 log;
+++: 4 or more logs.

EXAMPLE 5: ANTIMICROBIAL ACTIVITY OF PA6-GP20 ENZYME MODIFIED WITH THE HYDROPHOBIC PEPTIDE STRETCH WALMAGH 1

The fusion protein PA6-gp20 with the N-terminal peptide stretch Walmagh 1 according to SEQ ID NO: 56 was produced as described in example 1. The antimicrobial activity of said fusion protein against *Propionibacterium acnes* DSMZ 1897 and *Propionibacterium acnes* DSMZ 16379 was tested by using the plating test described in example 2. The measured activity of the fusion protein is shown in Table 9.

The results presented in Table 9 show antimicrobial activity of the fusion protein against both bacterial strains of *Propionibacterium acnes*.

TABLE 9

| Fusion protein | Enzyme part | Peptide stretch (N-terminal unless otherwise indicated) | Activity against *Propionibacterium acnes* DSMZ 1897 | Activity against *Propionibacterium acnes* DSMZ 16379 |
|---|---|---|---|---|
| SEQ ID NO: 124 | PA6-gp20 (SEQ ID NO: 61) | Walmagh 1 (SEQ ID NO: 56) | ++ | ++ |

Abbreviations:
++: 2-3 log;

The fusion proteins in Table 6 to 9 without any tag and linker were also tested with the activity assays described above. They all showed antimicrobial activity against the used bacterial strains in Table 6 to 9.

The invention claimed is:

1. A fusion protein comprising an amino acid sequence selected from the group consisting of SEQ ID NO: 15, SEQ ID NO: 16, SEQ ID NO: 17, and SEQ ID NO: 18.

2. An isolated nucleic acid molecule comprising a nucleotide sequence encoding the fusion protein according to claim 1.

3. A vector comprising the nucleic acid molecule according to claim 2.

4. An isolated host cell comprising the nucleic acid molecule according to claim 2.

5. An isolated host cell comprising the vector according to claim 3.

6. A method of treating a Gram-positive bacterial infection or contamination comprising contacting a subject, surface or sample having said infection or contamination with the fusion protein according to claim 1.

7. The method of claim 6, wherein the subject, surface or sample is foodstuff, food processing equipment, food processing plants, surfaces coming into contact with foodstuff, medical devices, or surfaces in hospitals and surgeries.

8. A pharmaceutical composition comprising the fusion protein according to claim 1.

* * * * *